(12) United States Patent
Schaper et al.

(10) Patent No.: US 6,596,727 B1
(45) Date of Patent: Jul. 22, 2003

(54) SUBSTITUTED PYRIMIDINES, PROCESSES FOR THEIR PREPARATION, AND THEIR USE AS PESTICIDES AND FUNGICIDES

(75) Inventors: Wolfgang Schaper, Diedorf (DE); Rainer Preuss, Hofheim am Taunus (DE); Gerhard Salbeck, deceased, late of Kriftel/Taunus (DE), by Gisela Salbeck, heiress; Peter Braun, Mainz (DE); Werner Knauf, Eppstein/Taunus (DE); Burkhard Sachse, Kelkheim (DE); Anna Waltersdorfer, Frankfurt am Main (DE); Manfred Kern, Lörzweiler (DE); Peter Lümmen, Niedernhausen (DE); Werner Bonin, Kelkheim (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 1312 days.

(21) Appl. No.: 08/616,667

(22) Filed: Mar. 15, 1996

Related U.S. Application Data

(62) Division of application No. 08/029,889, filed on Mar. 11, 1993, now Pat. No. 5,571,815.

(30) Foreign Application Priority Data

Mar. 14, 1992 (DE) .......................................... 42 08 254

(51) Int. Cl.⁷ .................... C07D 239/32; C07D 239/42; A01N 43/54
(52) U.S. Cl. .......................... 514/269; 514/256; 514/63; 514/259; 514/249; 544/298; 544/319; 544/326; 544/327; 544/229; 544/296; 544/276; 544/283; 544/284; 544/287; 544/289; 544/295; 544/293; 544/328
(58) Field of Search ................................ 544/298, 319, 544/326, 327, 229, 296, 278, 283, 284, 287, 289; 514/256, 269, 263, 259, 249

(56) References Cited

U.S. PATENT DOCUMENTS 3,470,182 A 9/1969 Hardtman et al. ....... 260/251.4
4,196,207 A 4/1980 Webber ...................... 544/278

FOREIGN PATENT DOCUMENTS

| EP | A-0 323 757 | 7/1989 |
| EP | 0326328 | 8/1989 |
| EP | A-0 447 891 | 9/1991 |
| EP | A-0 452 002 | 10/1991 |
| EP | A-0 519 211 | 12/1992 |
| WO | WO 92/08704 | 5/1992 |

OTHER PUBLICATIONS

Grant and Hackh's Chemical Dictionary Fifth Edition (1987) p. 282, re Leters.*
Thomae, Chemical Abstracts, vol. 67: 100149 (1967).*
Cronin et al, Chemical Abstracts, vol. 70: 68419 (1969).*
Robba et al, Chemical Abstracts, vol. 75: 151829 (1971).*
Eck et al, Chemical Abstracts, vol. 81 entry 120676 (1974).*
Keir et al, Chemical Abstracts, vol. 86, entry 436 45 (1977).*
Cox et al, Chemical Abstracts, vol 87, (1977).*
Sunley et al, Chemical Abstracts, vol. 89: 124572 (1978).*
Miki et al, Chemical Abstracts, vol., 90: 87501 (1979).*

* cited by examiner

*Primary Examiner*—John M. Ford
(74) *Attorney, Agent, or Firm*—Frommer Lawrence & Haug LLP

(57) ABSTRACT

Substituted 4-amino- and 4-alkoxy-cycloalkylpyrimidines, processes for their preparation, and their use as pesticides and fungicides The invention relates to compounds of the formula

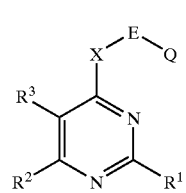

(I)

in which $R^1$, $R^2$, $R^3$ and Q are as defined in the description, X is NH or oxygen and E is a bond or a 1- to 4-membered carbon chain, to a process for their preparation, to agents containing them, and to their use in the control of pests and as fungicides.

9 Claims, No Drawings

SUBSTITUTED PYRIMIDINES, PROCESSES FOR THEIR PREPARATION, AND THEIR USE AS PESTICIDES AND FUNGICIDES

This application is a division of application Ser. No. 08/029,889, filed Mar. 11, 1993 now U.S. Pat. No. 5,571,815.

The invention relates to novel substituted 4-amino- and 4-alkoxypyrimidines, to processes for their preparation and to their use as pesticides, in particular as insecticides, acaricides and fungicides.

It has already been disclosed that certain substituted 4-aminopyrimidines have a good fungicidal, acaricidal and insecticidal activity (cf. EP-A-57,440, EP-A-196,524, EP-A-264,217, EP-A-276,406, EP-A-323,757, EP-A-326,328, EP-A-326,329, EP-A-326,330, EP-A-356,158, EP-A-370,704, EP-A-411,634, EP-A-424,125, EP-A-452,002, EP-A-459,611, EP-A-447,891). However, the biological activity of these compounds is not satisfactory in all fields of application, in particular when low dosage rates and concentrations are used.

Novel substituted 4-amino- and 4-alkoxypyrimidines of the formula I have been found,

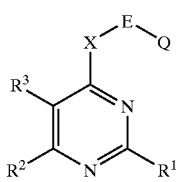

(I)

in which $R^1$ is hydrogen, halogen, $(C_1-C_4)$-alkyl or $(C_3-C_6)$-cycloalkyl, $R^2$ is hydrogen, $(C_1-C_4)$-alkyl, halogen $(C_1-C_4)$-halo-alkyl, $(C_1-C_4)$-alkoxy, $(C_1-C_4)$-haloalkoxy, $(C_1-C_4)$-alkoxy-$(C_1-C_4)$-alkyl, $(C_1-C_4)$-alkylthio, $(C_1-C_4)$-alkylthio-$(C_1-C_4)$-alkyl, $(C_1-C_4)$-alkylamino or di-$(C_1-C_4)$-alkylamino, $R^3$ is hydrogen, $(C_1-C_4)$-alkyl, $(C_1-C_4)$-alkoxy, $(C_1-C_4)$-haloalkoxy, halogen, $(C_1-C_4)$-alkylthio, amino, $(C_1-C_4)$-alkylamino or di-$(C_1-C_4)$-alkylamino or $R^2$ and $R^3$ together with the carbon atoms to which they are bonded form an unsaturated 5- or 6-membered isocyclic ring which, if it is a 5-membered ring, can contain an oxygen or sulfur atom in place of $CH_2$ and which is optionally substituted by 1, 2 or 3 identical or different radicals, these radicals being $(C_1-C_4)$-alkyl, $(C_1-C_4)$-alkoxy, $(C_1-C_4)$-halo-alkyl, preferably trifluoromethyl, $(C_1-C_4)$-halo-alkoxy and/or halogen, or $R^2$ and $R^3$ together with the carbon atoms to which they are bonded form a saturated 5-, 6- or 7-membered isocyclic ring which can contain an oxygen or sulfur atom in place of $CH_2$ and which is optionally substituted by 1, 2 or 3 $(C_1-C_4)$-alkyl groups, X is NH or oxygen, E is a direct bond or a straight-chain or branched $(C_1-C_4)$-alkanediyl group, preferably a direct bond, Q has the meaning $Q^1$ and
$Q^1$ is a cycloalkyl group of the formula II

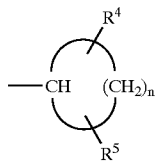

(II)

in which n is an integer from 2 to 7, $R^4$ and $R^5$ are identical or different and are in each case hydrogen, $(C_1-C_{12})$-alkyl, $(C_3-C_8)$-cycloalkyl, $(C_3-C_8)$-cyclo alkyl-$(C_1-C_4)$-alkyl, $(C_1-C_8)$-alkoxy, $(C_3-C_8)$-cyclo-alkoxy, $(C_1-C_4)$-alkoxy-$(C_1-C_4)$-alkyl, $(C_3-C_8)$-cyclo-alkyl-$(C_1-C_4)$-alkoxy, tri-$(C_1-C_8)$-alkylsilyl, preferably dimethyl-$(C_1-C_8)$-alkylsilyl or tri-ehtylsilyl, di-$(C_1-C_8)$-alkyl-$(C_3-C_8)$-cycloalkyl-silyl, preferably dimethylcyclohexylsilyl, di-$(C_1-C_8)$-alkyl (phenyl-$(C_1-C_4)$-alkyl)-silyl, preferably dimethyl-(phenyl-$(C_1-C_4)$-alkyl)silyl, di-$(C_1-C_8)$-alkyl-$(C_1-C_4)$-haloalkylsilyl, preferably dimethyl-$(C_1-C_4)$-haloalkylsilyl, dimethylphenyl-silyl, $(C_1-C_4)$-haloalkyl, halogen, $(C_1-C_4)$-haloalkoxy, heteroaryl, phenyl, phenyl-$(C_1-C_4)$-alkyl, benzyloxy, benxzyloxy-$(C_1-C_4)$-alkyl, benzylthio, phenylthio or phenoxy, it being possible for the phenyl rings in the seven last-mentioned radicals to be unsubstituted or provided with one or two substituents and these substituents are identical or different and can be in each case $(C_1-C_8)$-alkyl, $(C_3-C_8)$-cycloalkyl, $(C_1-C_4)$-haloalkyl, preferably trifluoromethyl, halogen, $(C_1-C_4)$-dialkylamino, $(C_1-C_4)$-alkylthio, $(C_1-C_8)$-alkoxy, $(C_1-C_4)$-haloalkoxy, $(C_1-C_4)$-alkoxy-$(C_1-C_4)$-alkoxy, $H_5C_2$-O-$[CH_2-CH_2$-O-$]_x$, 2-(tetrahydro-2H-pyran-2-yloxy)-ethoxy, $(C_2-C_8)$-alkenyl, $(C_2-C_8)$-alkynyl, benzyloxy which in the phenyl radical optionally carries one or two identical or different substituents selected from the group comprising $(C_1-C_4)$-alkyl, $(C_1-C_4)$-haloalkyl, $(C_1-C_4)$-alkoxy, $(C_1-C_4)$-haloalkoxy and halogen, or tri-$(C_1-C_4)$-alkylsilylmethoxy, preferably dimethyl-$(C_1-C_4)$-alkylsilylmethoxy, $(C_3-C_8)$-cycloalkyl-$(C_1-C_4)$-alkoxy, 1,3-dioxolan-2-ylmethoxy, tetrahydro-furan-2-ylmethoxy or tetrahydro-2H-pyran-2-ylmethoxy, where, both, $R^4$ and $R^5$ do not coincidentally denote hydrogen, and where, in two adjacent substituents which are identical or different and are selected from the group comprising $(C_1-C_8)$-alkyl and $(C_1-C_8)$-alkoxy, in each case one hydrogen atom can be replaced by a joint carbon-carbon bond which links these two substituents, or $R^4$ and $R^5$ together with the cycloalkyl group form a 3-8-membered spirocyclic, preferably saturated spirocyclic, ring system which can contain oxygen or sulfur in place of one or two $CH_2$ groups or $R^4$ and $R^5$ together with the carbon atoms carrying them form a fused 5- or 6-membered, preferably saturated isocycle, in particular a cyclopentane or cyclohexane system, X is 2, 3 or 4, preferably 2, or Q has the meaning $Q^2$ and $Q^2$ is a group of the formula III

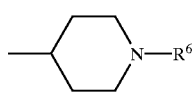

(III)

in which $R^6$ is a group of the formula Z-W and Z is a direct bond or carbonyl or sulfonyl and W is an aryl or heteroaryl group which can be unsubstituted or provided with one or two substituents and these substituents are identical or different and are in each case $(C_1-C_8)$-alkyl, $(C_3-C_8)$-cycloalkyl, trifluoromethyl, halogen $(C_1-C_4)$-alkoxy, $(C_1-C_4)$-dialkylamino or $(C_1-C_4)$-alkylthio.

If Q has the meaning $Q^1$, $R^2$ and $R^3$ together with the carbon atoms carrying them form an unsaturated 6-membered isocyclic ring and $R^4$ and $R^5$ form a fused 5- or 6-membered ring, then the meaning 5-membered ring is preferred for the two last-mentioned radicals.

If Q has meaning $Q^1$, and $R^2$ and $R^3$ together with the carbon atoms carrying them form a furan or thiophene system, then $Q^1$ is preferably not $(C_3-C_8)$-cycloalkyl which is optionally substituted and the substituents are in particular alkyl such as $(C_1-C_4)$-alkyl, alkoxy such as $(C_1-C_4)$-alkoxy, haloalkyl such as $(C_1-C_4)$-haloalkyl, haloalkoxy such as $(C_1-C_4)$-haloalkoxy or halogen.

Preferred compounds of the formula I are those in which
$R^1$ is hydrogen, methyl or cyclopropyl,
$R^2$ is $(C_1-C_4)$-alkyl, chlorine, methoxy, ethoxy or methoxymethyl,
$R^3$ is hydrogen, $(C_1-C_3)$-alkyl, methoxy, ethoxy or halogen or
$R^2$ and $R^3$ together with the carbon atoms to which they are bonded form an unsaturated 5- or 6-membered ring which can contain an oxygen or sulfur atom, or $R^2$ and $R^3$ together with the carbon atoms to which they are bonded form a saturated 5- or 6-membered ring which can contain a sulfur atom,
Q has the meaning $Q^1$ or $Q^2$, in particular those compounds of the formula I in which
$R^1$ is hydrogen or methyl,
$R^2$ is methyl, ethyl, methoxy, ethoxy or methoxy-methyl,
$R^3$ is methyl, ethyl, methoxy, chlorine or bromine, or
$R^2$ and $R^3$ together with the carbon atoms to which they are bonded form the quinazoline system, or
$R^2$ and $R^3$ together with the carbon atoms to which they are bonded form a saturated 6-membered ring which can contain a sulfur atom and
Q has the meaning $Q^1$ or $Q^2$, preferably those compounds of the formula I in which
E is a direct bond,
$R^1$ is hydrogen,
$R^2$ is methyl, ethyl or methoxymethyl,
$R^3$ is chlorine, bromine or methoxy or
$R^2$ and $R^3$ together with the carbon atoms to which they are bonded form the quinazoline system which can be substituted by fluorine, chlorine, bromine or methyl, or
$R^2$ and $R^3$ together with the pyrimidine ring form the 5,6,7,8-tetrahydroquinazoline system or the 5,6-dihydro-7H-thiopyrano[2,3-d]pyrimidine or the 5,6-dihydro-8H-thiopyrano[3,4-d]pyrimidine system

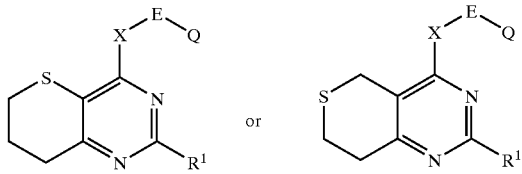

and
Q has the meaning $Q^1$ or $Q^2$.

Very particularly preferred compounds of the formula I are those in which
E is a direct bond,
$R^1$ is hydrogen,
$R^2$ is methoxymethyl and $R^3$ is methoxy or
$R^2$ is methyl or ethyl and $R^3$ is chlorine or bromine or
$R^2$ and $R^3$ together with the carbon atom to which they are bonded form a quinazoline system which is substituted by fluorine, chlorine or methyl, or form a 5,6,7,8-tetrahydroquinazoline system and
Q has the meaning $Q^1$, in particular those compounds of the formula I in which
E is a direct bond,
$R^1$ is hydrogen,
$R^2$ is methoxymethyl and $R^3$ is methoxy or
$R^2$ is ethyl and $R^3$ is chlorine or
$R^2$ and $R^3$ together with the carbon atom to which they are bonded form a quinazoline or a 5,6,7,8-tetrahydroquinazoline system and
Q is a cycloalkyl group of the formula II which is substituted in the 3- or 4-position and in which
n is 4 or 5,
$R^4$ is $(C_3-C_8)$-alkyl, cyclopentyl, cyclohexyl, phenyl or phenoxy, it being possible for the two last-mentioned radicals to be unsubstituted or provided with one or two substituents which can be identical or different and which are fluorine chlorine, bromine, $(C_1-C_4)$-alkyl, $(C_1-C_4)$-alkoxy, trifluoromethyl, $(C_1-C_2)$-haloalkoxy, cyclohexyl, 2-ethoxyethoxy, methylthio or dimethylamino, and
$R^5$ is hydrogen.

Other very particularly preferred compounds of the formula I are those in which
E is a direct bond,
$R^1$ is hydrogen,
$R^2$ is methoxymethyl and $R^3$ is methoxy or
$R^2$ is ethyl and $R^3$ is chlorine, or
$R^2$ and $R^3$ together with the carbon atoms to which they are bonded form a quinazoline or a 5,6,7,8-tetrahydroquinazoline system,
Q has the meaning $Q^1$ and
$Q^1$ is cyclohexyl which is substituted in the 4-position, and E and the substituent in the 4-position of the cyclohexyl are in the cis-position relative to each other,
$R^4$ is as defined above and
$R^5$ is preferably hydrogen.

In the above formula I, "halogen" is to be understood as meaning a fluorine, chlorine, bromine or iodine atom, preferably a fluorine, chorine or bromine atom, the term "$(C_1-C_4)$-alkyl" is to be understood as meaning an unbranched or branched hydrocarbon radical having 1–4 carbon atoms such as, for example, the methyl, ehtyl, propyl, 1-methylethyl, 1-methylpropyl, 2-methylpropyl or 1,1-dimethylethyl radical, the term "$(C_1-C_8)$-alkyl" is to be understood as meaning the abovementioned alkyl radicals and, for example, the pentyl, 2methylbutyl or 1,1-dimethylpropyl radical, the hexyl, heptyl, octyl radical, or 1,1,3,3-tetramethylbutyl; the term "$(C_1-C_{12})$-alkyl" is to be understood as meaning the abovementioned alkyl radicals as well as, for example, the nonyl, decyl, undecyl or dodecyl radical; the term "$(C_3-C_8)$-cycloalkyl" is to be understood as meaning the cyclopropyl, cyclobutyl, cyclopentyl, cyclohexyl, cycloheptyl or cyclooctyl group; the term "$(C_1-C_4)$-alkoxy" is to be understood as meaning an alkoxy group whose hydrocarbon radical has the meaning given for the term "$(C_1-C_4)$-alkyl"; the term "$(C_3-C_8)$-cycloalkoxy" is to be understood as meaning a cycloalkoxy group whose hydrocarbon radical has the meaning given under "$(C_3-C_8)$-cycloalkyl"; the term "$(C_1-C_4)$-alkylthio" is to be understood as meaning an alkylthio group whose hydrocarbon radical has the meaning given for the term "$(C_1-C_4)$-alkyl"; the term "$(C_1-C_4)$-haloalkoxy" is to be understood as meaning a haloalkoxy group whose halohydrocarbon radical has the meaning given for the term "$(C_1–C_4)$-haloalkyl", the term "$(C_1–C_4)$-alkoxy-$(C_1–C_4)$-alkyl" is to be understood as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group; the term "$(C_1–C_4)$-alkylthio-$(C_1–C_4)$-alkyl" is to be understood as meaning, for example, methylthiomethyl, ethylthiomethyl, propylthiomethyl, 2-methylthioethyl, 2-ethylthioethyl or 3-methylthiopropyl; the term "$(C_1–C_4)$-alkylamino" is to be understood as meaning an alkylamino group whose hydrocarbon radical has the meaning given under the term "$(C_1–C_4)$-alkyl", preferably the ethyl and methylamino group; the term "di-$(C_1–C_4)$-alkylamino" is to be understood as meaning a dialkylamino group whose hydrocarbon radicals have the meaning given under the term "$(C_1–C_4)$-alkyl", preferably the dimethyl and diethylamino group; the term "$(C_1–C_4)$-haloalkyl" is to be understood as meaning an alkyl group mentioned under the term "$(C_1–C_4)$-alkyl", in which one or more hydrogen atoms is replaced by the abovementioned halogen atoms, preferably chlorine or fluorine, such as, for example, the trifluoromethyl group, the 2,2,2-trifluoroethyl group, the chloromethyl or the fluoromethyl group, the difluoro-methyl group or the 1,1,2,2-tetrafluoroethyl group; the term $(C_3–C_8)$-cycloalkyl-$(C_2–C_4)$-alkyl" is to be understood as meaning one of the abovementioned $(C_1–C_4)$-alkyl groups which is substituted by one of the abovementioned $(C_3–C_8)$-cycloalkyl groups, for example cyclohexylmethyl, cyclohexylethyl, cyclohexylpropyl, cyclohexylbutyl or 1-cyclohexyl-1-methyl-ethyl; the term "phenyl-$(C_1–C_4)$-alkyl" is to be understood as meaning one of the abovementioned $(C_1–C_4)$-alkyl groups which is substituted by a phenyl group, for example the benzyl group, the 2-phenylethyl group, the 1-phenylethyl group, the 1-mehtyl-1-phenylethyl group, the 3-phenylpropyl group, the 4-phenylbutyl group or the 2-methyl-2-phenylethyl group; the term "aryl" is to be understood as meaning, for example, phenyl, naphthyl or biphenylyl, preferably phenyl; the term "heteroaryl" is to be understood as meaning an aryl radical in which at least one CH group is replaced by N and/or at least two adjacent CH groups are replaced by S, NH or O; the term "benzyloxy-$(C_1–C_4)$-alkyl" is to be understood as meaning a $(C_1–C_4)$-alkyl group which has the abovementioned meanings and which is substituted by a benzyloxy group, for example the benzyloxymethyl or the 2-(benzyloxy)-ethyl group; the term "$(C_3–C_8)$-cycloalkyl-$(C_1–C_4)$-alkoxy" is to be understood as maning a $(C_1–C_4)$-alkoxy group which has the abovementioned meanings and which is substituted by a $(C_3–C_8)$-cycloalkyl group which has the abovementioned meanings, for example the cyclopropylmethyl or the cyclohexylmethyl group; the term "tri-$(C_1–C_8)$-alkylsilyl" is to be understood as meaning a trialkylsilyl group which carries preferably two methyl groups and one $(C_1–C_8)$-alkyl group having the abovementioned meanings, for example the trimethylsilyl, the dimethylethylsilyl or the dimethyloctylsilyl group; the term "di-$(C_1–C_8)$-alkyl-$(C_1–C_4)$-haloalkylsilyl" is to be understood as meaning a silyl radical which carries preferably two methyl groups and one $(C_1–C_4)$-haloalkyl radical having the meanings given under the term $(C_1–C_4)$-haloalkyl, for example the dimethyl-3,3,3-trifluoropropylsilyl radical; the term "$(C_1–C_4)$-alkoxy-$(C_1–C_4)$-alkoxy" is to be understood as meaning, for example, the ethoxymethoxy, 2-ethoxyethoxy, 2-butoxyethoxy or 2-methoxyethoxy group; the term "$(C_2–C_8)$-alkenyl" is to be understood as meaning, for example, the allyl, 1-methylallyl, 2butenyl or 3-methyl-2-butenyl group; the term "$(C_2–C_8)$-alkynyl" is to be understood as meaning, for example, the propargyl, 2-butynyl or 2-pentynyl group; the term "tri-$(C_1–C_4)$-alkylsilylmethoxy" is to be understood as meaning a trialkylsilylmethoxy radical which has preferably 2 methyl groups and in which the $(C_1–C_4)$-alkyl group has the abovementioned meanings; and the term "di-$(C_1–C_8)$-alkyl-phenyl-$(C_1–C_4)$-alkylsilyl" is to be understood as meaning a trialkylsilyl radical which has preferably two methyl groups and in which one alkyl group has the meanings mentioned above for the term "phenyl-$(C_1–C_4)$-alkyl", preferably the dimethylbenzylsilyl group.

What has been explained above applies correspondingly to homologues or radicals derived thereof.

The present invention relates to the compounds of the formula I in the form of the free base or of an acid addition salt. Acids which can be used for salt formatoin are inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula I have one or more asymmetric carbon atoms. Racemates and diastereomers can therefore occur. The invention embraces the pure isomers as well as their mixtures. The diastereomer mixtures can be resolved into the components by customary methods, for example by selective crystallization from suitable solvents or by chromatography. Racemates can be resolved to give the enantiomers by conventional methods, for example by salt formation with an optically active acid, separation of the diastereomeric salts and liberation of the pure enantiomers by means of a base.

If $Q^1$ is a cycloalkyl group of the formula II and n is 4, 5 or 6, preferably 5, then E and a radical $R^4$ or $R^5$ which is preferably in the 4-position if n=5 are preferably in the cis-configuration relative to each other.

The invention furthermore relates to a process for the preparation of compounds of the formula I, which comprises reacting a compound of the formula IV

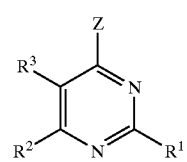

(IV)

in which $R^1$, $R^2$ are as defined in formula I and Z is a leaving group, for example halogen, alkylthio, alkanesulfonyloxy or arylsulfonyloxy, alkylsulfonyl or arylsulfonyl, with a nucleophile of the formula V

HX–E–Q    (V)

in which X, E and Q are as defined in formula I and, if $R^3$ is hydrogen, the resulting compounds of the formula I are optionally chlorinated or brominated on carbon atom 5 of the pyrimidine.

The above mentioned substitution reaction is known in principle. The leaving group Z can be varied within wide limits and can be, for example, a halogen atom such as fluorine, chlorine, bromine or iodine, or alkylthio such as methyl- or ethylthio, or alkanesulfonyloxy such as methane-, trifluoromethane- or ethanesulfonyloxy, or arylsulfonyloxy such as benxenesulfonyloxy or toluenesulfonyloxy, or alkylsulfonyl such as methyl- or ethylsulfonyl, or arylsulfonyl such as phenyl- or toluenesulfonyl.

The abovementioned reaction is carried out in a temperature range of 20–150° C., expediently in the presence of a base and if appropriate in an inert organic solvent such as N,N-dimethylformamide, N,N-diemthylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the solvents mentioned can also be used.

In the event that X is oxygen, then suitable bases are, for example, carbonates, hydrogen carbonates, amides or hydrides of alkali metals or alkaline earth metals such as sodium carbonate, sodium hydrogen carbonate, potassium carbonate, sodium amide or sodium hydride, and in the event that X is NH, they are, for example, carbonates, hydrogen carbonates, hydroxides, amides or hydrides of alkali metals or alkaline earth metals such as sodium carbonate, sodium hydrogen carbonate, potassium carbonate, sodium hydroxide, sodium amide or sodium hydride, or organic bases such as triethylamine or pyridine. A second equivalent of an amine V can also be used as auxiliary base.

The starting compounds of the formula IV can be prepared by processes which are analogous to known processes. The starting materials used are acetoacetic ester derivatives which are converted into the halopyrimidines via the corresponding hydroxypyrimidines:

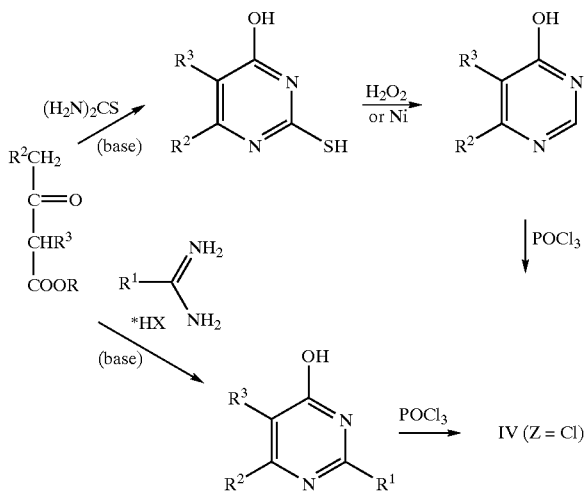

Furthermore, the starting compounds of the formula IV can be obtained from malonic ester derivatives in analogy to known processes:

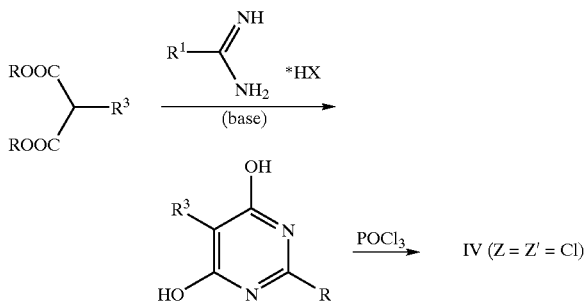

In the event that X is oxygen, the nucleophiles of the formula V, which are required as starting materials, can be prepared by known processes, for example by reducing a carbonyl group with a suitable reducing agent, for example a complex metal hydride or, in the case of an aldehyde or ketone, also using hydrogen and a hydrogenation catalyst. Other possibilities are the reaction of an organometal compound with a carbonyl group or an oxirane. To synthesize cyclohexanol derivatives, it is also possible to react suitable substituted phenols with hydrogen in the presence of a hydrogenation catalyst.

In the event that X is NH, the nucleophiles of the formula V, which are required as starting materials, can also be prepared by known methods, for example reduction of an oxime or of a nitrile with a suitable reducing agent, for example a complex metal hydride or hydrogen in the presence of a hydrogenation catalyst, reductive amination or Leuckart-Wallach reaction of an aldehyde or ketone or Gabriel reaction of an alkyl halide or alkyl tosylate. To synthesize cyclohexylamine derivatives, it is also possible to react suitable substituted anilines with hydrogen in the presence of a hydrogenation catalyst.

The compounds of the formula I in which $R^3$ is halogen can be halogenated by known processes.

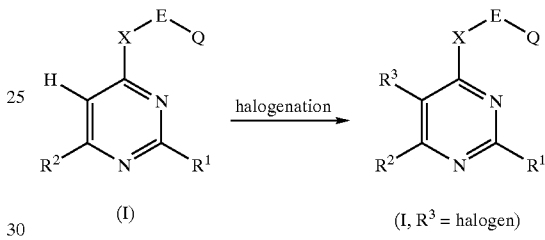

In the case of the 5-chloro derivatives, substances which can be used are, for example, elemental chlorine, sodium hypochlorite, sulfuryl chloride or N-chlorosuccinimide, and particularly suitable for the bromination are elemental bromine or N-bromosuccinimide. Examples of suitable solvents are dichloromethane, chloroform or glacial acetic acid.

The active ingredients are suitable for controlling animal pests, in particular insects, arachnids, helminths and molluscs, very particularly preferably for controlling insects and arachnids, which can be found in agriculture, in livestock breeding, in forests, in the protection of stored goods and materials as well as in the field of hygiene, and they are well tolerated by plants and have a favorable toxicity to warm-blooded species. They are active against normally-sensitive and resistant species and against all or some stages of development. The abovementioned pests include:

From the order of the Acarina, for example *Acarus siro*, Agras spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp,. Tarsonemus spp., *Bryobia praetiosa*, Panonychus spp,. Tetranychus spp., Eotetranychus spp., Oligonychus spp., Eutetranychus spp.

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpohagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloxera vastatrix,* Pemphigus spp., *Pediculus humanus corporis*Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma langerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatris thruberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoceia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp,. *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilla spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the class of the Helminthes, for example, Haemonchus, Trichostrongulus, Ostertagia, Cooperia, Chabertia, Strongyloides, Oesophagostomum, Hyostrongulus, Ancylostoma, Ascaris and Heterakis as well as Fasciola and phytopathogenic nematodes, for example those from the genera Meloidogyne, Heterodera, Ditylenchus, Aphelenchoides, Radopholus, Globodera, Pratylenchus, Longidorus and Xiphinema.

From the class of the Gastropoda, for example, Deroceras spp., Arion spp., Lymnaea spp., Galba spp., Succinea spp., Biomphalaria spp., Bulinus spp., and Oncomelania spp.

From the class of the Bivalva, for example, Dreissena spp.

The invention also relates to insecticidal and acaricidal agents which contain the compounds of the formula I, besides suitable formulation auxiliaries.

The agents according to the invention generally contain the active substances of the formula I to the extent of 1 to 95% by weight.

They can be formulated in various ways, depending on the prevailing biological and/or chemico-physical parameters. The following are therefore possible for formulation: wettable powders (WP), emulsifiable concentrates (EC), aqueous solutions (SC), emulsions, sprayable solutions, dispersions on an oil or water basis (SC), suspoemulsions (SC), dusts (DP), seed-dressing agents, granules in the form of microgranules, spray granules, coated granules and adsorption granules, water-dispersible granules (WG), ULV formulations, microcapsules, waxes or baits.

These individual formulation types are known in principle and are described, for example, in: Winnacker-Küchler, "Chemische Technologie" [Chemical Technology], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries which are required, such as inert materials, surfactants, solvents and other additives are equally known and are described, for example, in: Watkins, "Handbook of Insecticide Dust Diluents and Carriers", 2nd., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to produce combinations with other pesticidally active substances, fertilizers and/or growth regulators, for example in the form of a readymix or a tank mix. Wettable powders are preparations which are uniformly dispersible in water and which contain, besides the active substance and in addition to a diluent or inert material, wetting agents, for example polyoxethylated alkylphenols, polyoxethylated fatty alcohols, alkyl- or alkylphenolsulfonates, and dispersing agents, for example sodium ligninsulfonate, sodium 2,2'-dinaphthylmethane-6, 6'-disulfonate, sodium dibutylnaphthalenesulfonate, or sodium oleylmethyltaurate.

Emulsifiable concentrates are prepared by dissolving the active substance in an organic solvent, for example butanol, cyclohexanone, dimethylformamide, xylene or higher-boiling aromatics or hydrocarbons, with addition of one or more emulsifiers. Examples of emulsifiers which can be used are: calcium salts of alkylarylsulfonates, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxethylene sorbitol esters.

Dusts are obtained by grinding the active substance with finely divided solid substances, for example talc, natural clays such as kaolin, bentonite, pyrophyllite or diatomaceous earth. Granules can be prepared either by atomizing the active substance onto adsorptive, granulated inert material or by applying active substance concentrates onto the surface of carrier materials such as sand or faolinites, or of granulated inert material, by means of adhesives, for example polyvinyl alcohol or sodium polyacrylate, or alternatively mineral oils. Suitable active substances can also be granulated in the fashion conventional for the preparation of fertilizer granules, if desired as a mixture with fertilizers.

The active substance concentration in wettable powders is, for example, approximately 10 to 90% by weight, the remainder to 100% is composed of conventional formulation components. In the case of emulsifiable concentrates, the active substance concentration can be approximately 5 to 80% by weight. Formulations in the form of dusts usually contain 5 to 20% of active substance, sprayable solutions approximately 2 to 20% by weight. In the case of granules, the active substance content depends partly on whether the active compound is liquid or solid and on which granulation auxiliaries, fillers, etc. are used.

In addition, the active substance formulations mentioned contain, if appropriate, the adhesives, wetting agents, dispersants, emulsifiers, penetrants, solvents, fillers or carriers which are conventional in each case.

For use, the concentrates which exist in commercially available form are, if appropriate, diluted in the customary manner, for example using water in the case of wettable powders, emulsifiable concentrates, dispersions and also in the case of some microgranules. Preparations in the form of a dust and granulated preparations as well as sprayable solutions are customarily not further diluted with other inert substances before use.

The application rate required depends on the external conditions such as, inter alia, temperature and humidity. It can vary within wide limits, for example between 0.001 and 10.0 kg/ha or more of active ingredient, but it is preferably between 0.005 and 5 kg/ha.

The active substances according to the invention may be present in their commercially available formulations and in the application forms prepared from these formulations in the form of mixtures with other active substances such as insecticides, attractants, sterilants, acaricides, nematicides, fungicides, growth-regulating substances or herbicides.

The pesticides include, for example, phosphoric esters, carbamates, carboxylic esters, formamidines, tin compounds and substances produced by microorganisms. Preferred components for mixtures are 1. from the group comprising the phosphorus compounds acephate, azamethiphos, azinphos-ethyl, azinphos-methyl, bromophos, bromophos-ethyl, chlorfenvinphos, chlormephos, chlorpyrifos, chlorpyriphos-methyl, demeton, demeton-S-methyl, demeton-S-methyl-sulphone, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetraclorvinphos, thiometon, triazophos, trichlorphon, vamidothion;

2. from the group comprising the carbamates aldicarb, 2-secbutylphenyl methylcarbamate (BPMC), carbaryl, carbofuran, carbosulfan, cloethocarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylidenamino)-N-methyl-N-(morpholinothio) carbamate (UC 51717);

3. from the group comprising the carboxylic esters allethrin, alphamethrin, 5-benzyl-3-furylmethyl-(E)-(1R)-cis-2,2-dimethyl-3-(2-oxothiolan-3-ylidene-methyl)cyclopropanecarboxylate, bioallethrin, bioallethrin ((S)cyclopentyl isomer), bioresmethrin, biphenate, (RS)-1-cyano-1-(6-phenoxy-2-pyridyl) methyl-(1RS)-trans-3-(4-tert.butylphenyl)-2,2-dimethylcyclopropanecarboxylate (NCI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (natural products), resmethrin, tefluthrin, tetramethrin, tralomethrin;

4. from the group comprising the amidines amitraz, chlordimeform;

5. from the group comprising the tin compounds cyhexatin, fenbutatin oxide;

6. others abamectin, *Bacillus thuringiensis,* bensultap, binapacryl, bromopropylate, buprofezin, camphechlor, cartap, chlorobenzilate, chlorfluazuron, 2-(4-chlorophenyl)-4,5-diphenylthiophene (UBI-T 930), chlorfentezine, 2-naphthylmethyl cyclopropanecarboxylate (Ro12-0470), cyromazin, ethyl N-(3,5-dichloro-4-(1,1,2,3,3,3-hexafluoro-1-propyloxy) phenyl)carbamoyl)-2-chlorobenzcarboximidate, DDT, dicofol, N-(N(3,5-dichloro-4-(1,1,2,2-tetrafluoroethoxy)-phenylamino)carbonyl)-2,6-difluorobenzamide (XRD 473), diflubenzuron, N-(2,3-dihydro-3-methyl-1,3-thiazol-2-yliden)-2,4-xylidine, dinobuton, dinocap, endosulfan, ethofenprox, (4-ethoxyphenyl)(dimethyl)(3-(3-phenoxyphenyl) propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800) granulosis and nuclear polyhedrosis viruses, fenthiocarb, flubenzimine, flucycloxuron, flufenoxuron, gamma-HCH, hexythiazox, hydramechylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam and triflumuron.

The active substance content of the use forms prepared from the commercially available formulations can be from 0.00000001 to 95% by weight of active substance, preferably between 0.00001 and 1% by weight.

Application is effected in a conventional fashion, matched to the use forms.

The active substances according to the invention are also suitable for controlling endo- and ectoparasites in the field of veterinary medicine or in the field of animal husbandry.

The active substances according to the invention are applied in a known fashion, such as by oral administration in the form of, for example, tablets, capsules, potions or granules, by dermal administration in the form of, for example, dipping, spraying, pouring-on and spotting-on and powdering, and also by parenteral administration in the form of, for example, an injection.

The novel compounds of the formula I according to the invention can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since they are excreted effectively in the feces, the development of insects in the feces of the animals can be prevented very simply in this fashion. The dosages and formulations suitable in each case are particularly dependent on the type and stage of development of the livestock and also on the infestation pressure, and can easily be determined and laid down by conventional methods. In the case of cattle, the novel compounds can be employed, for example, at dosage rates of 0.01 to 1 mg/kg of body weight.

The compounds of the formula I according to the invention are also distinguished by an outstanding fungicidal activity. Fungal pathogens which have already entered the plant tissue can be controlled successfully in a curative manner. This is particularly important and advantageous in the case of those fungal diseases which can no longer be controlled effectively with the otherwise customary fungicides once infection has taken place. The spectrum of action of the claimed compounds embraces a large number of various economically important phyto-pathogenic fungi such as, for example, *Pyricularia oryzae, Leptosphaeria nodorum, Drechslera teres,* powdery mildew species, *Venturia inaequalis, Botrytis cinerea, Pseudocercosporella herpotrichoides,* rusts as well as representatives of the Oomycetes such as, for example, *Phytophthora infestans* and *Plasmopara viticola.*

Besides, the compounds according to the invention are also suitable for use in industrial fields, for example as wood preservatives, as preservatives in paints, in cooling lubricants for metalworking, or as preservatives in drilling and cutting oils.

The invention also relates to agents which comprise the compounds of the formula I besides suitable formulation auxiliaries. The agents according to the invention generally comprise 1 to 95% by weight of the active substances of the formula I.

They can be formulated in various ways, depending on the prevailing biological and/or chemico-physical parameters. The following possibilities are therefore suitable for formulation: wettable powders (WP), emulsifiable concentrates (EC), aqueous dispersions on oil or water basis (SC), suspoemulsions (SC), dusts (DP), seed-dressing agents, granules in the form of water-dispersible granules (WG), ULV formulations, microcapsules, waxes or baits.

These individual formulation types are known in principle and are described, for example, in: Winnacker-Küchler, "Chemische Technologie" [Chemical Technology], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries which are required, such as inert materials, surfactants, solvents and other additives are equally known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

The active substances according to the invention can be employed, in their commercially available formulations, either on their own or in the form of a combination with other fungicides known from the literature.

Fungicides which are known from the literature and which can be combined according to the invention with the compounds of the formula (I) are, for example, the following products:

anilazine, benalaxyl, benodanil, benomyl, binapacryl, bitertanol, buthiobat, captafol, captan, carbendazim, carboxin, CGD-94240 F, chlobenzthiazone, chlorthalonil, cymoxanil, cyproconazole, cyprofuram, dichlofluanid, dichlomezin, dichlobutrazol, diethofencarb, difluconazole, dimethirimol, dimethomorph, diniconazole, dinocap, dithianon, dodemorph, dodine, edifenfos, ethirimol, etridazole, fenarimol, fenfuram, fenpiclonil, fenpropidin, fenpropimorph, fentin acetate, fentin hydroxide, fluaziram, fluobenzimine, fluorimide, flusilazole, flutolanil, flutriafol, folpet, fosetyl-aluminum, fuberidazole, furalaxyl, furmecyclox, guazatine, hexaconazole, imazalil, iprobenfos, iprodione, isoprothiolane, copper compounds such as copper oxychloride, copper oxine, copper oxide, mancozeb, maneb, mepronil, metalaxyl, methasulfocarb, methfuroxam, myclobutanil, nabam, nitrothalidopropyl, nuarimol, ofurace, oxadixyl, oxycarboxin, penconazole, pencycuron, PP 696, probenazole, probinel, prochloraz, procymidon, propamocarb, propiconazole, prothiocarb, pyracarbolid, pyrifenox, pyroquilon, rabenzazole, sulfur, tebuconazole, thiabendazole, thiofanate-methyl, thiram, tolclofos-methyl, tolyl-fluanid, triadimefon, triadimenol, tricyclazole, tridemorph, triflumizol, triforine, vinchlozolin, zineb, sodium dodecylsulfonate, sodium dodecylsulfate, sodium C13/C15-alcohol ether sulfonate, sodium cetostearylphosphate, dioctyl sodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropylenamines, laurylpyrimidinium bromide, ethoxylated quaternized fatty amines, alkyldimethylbenzylammonium chloride and 1-hydroxyethyl-2-alkylimidazoline.

The abovementioned components for the combinations represent known active substances, most of which are described in GH. R Worthing, U. S. B. Walker, The Pesticide Manual, 7th Edition (1983), British Crop Protection Council.

The active substance content of the use forms prepared from the commercially available formulations can vary within wide ranges, the active substance concentration of the use forms can be between 0.0001 and 95% by weight of active substance, preferably between 0.001 and 1% by weight. They are used in a fashion matched to the use forms.

The following examples serve to illustrate the invention.

A. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium ligninsulfonate and 1 part by weight of sodium oleoylmethyltaurate as wetting and dispersing agent, and grinding the mixture in a pin-disk mill.

c) A dispersion concentrate which is readily dispersible in water is prepared by mixing 40 parts by weight of active substance with 7 parts by weight of a sulfosuccinic monoester, 2 parts by weight of a sodium ligninsulfonate and 51 parts by weight of water and grinding the mixture in a ball mill to a fineness of below 5 microns.

d) An emulsifiable concentrate can be prepared from 15 parts by weight of active substance, 75 parts by weight of cyclohexanone as solvent and 10 parts by weight of oxethylated nonylphenol (10 EO) as emulsifier.

e) Granules can be prepared from 2 to 15 parts by weight of active substance and an inert granulate carrier material such as attapulgite, granulated pumice and/or quartz sand. It is expedient to use a suspension of the wettable powder of Example b) with a solids content of 30%, which is sprayed onto the surface of attapulgite granules, and these are dried and mixed intimately. The amount of the wettable powder is approx. 5% by weight and that of the inert carrier material approx. 95% by weight of the finished granules.

B. BIOLOGICAL EXAMPLES (USE AS FUNGICIDE)

Example 1

Barley plants in the 3-leaf stage are heavily inoculated with conidia of powdery mildew of barley (*Erysiphe graminis* f. sp. *hordei*) and placed in a greenhouse at 20° C. and a relative atmospheric humidity of 90–95%. 24 hours after the inoculation, the plants are wetted uniformly with the compounds listed in Table 1 at the active substance concentrations which are indicated. After an incubation time of 10 days, the plants are examined for incidence of powdery mildew of barley. The disease indicence is expressed in % of diseased leaf area, relative to untreated, 100% infected control plants.

Applied at 500 mg of active substance/l of spray mixture, the following substances are found to suppress disease completely:

Compounds according to Example No. 9, 17, 25, 30, 55, 80, 93, 99, 100.

Example 2

Barley plants cv. "Igri" in the 2-leaf stage are treated to runoff point with an aqueous suspension of the claimed compounds.

After the spray coating has dried on, the plants are inoculated with an aqueous spore suspension of *Pyrenophora teres* and incubated for 16 hours in a controlled-environment cabinet at a relative atmospheric humidity of 100%. The infected plants are subsequently grown on in the greenhouse at 25° C. and a relative atmospheric humidity of 80%.

Approx. 1 week after the inoculation, the disease is evaluated and the disease incidence is scored as diseased leaf area compared with the untreated, 100% infected control.

Applied at 500 mg of active substance/l of spray mixture, the following substances are found to suppress disease completely:

Compounds according to Example No. 2, 9, 10, 13, 14, 17, 25, 55, 80, 93, 106.

Example 3

Wheat cv. "Jubilar" in the 2-leaf stage is treated to runoff point with aqueous suspensions of the claimed compounds.

After the spray coating has dried on, the plants are inoculated with an aqueous spore suspension of *Puccinia recondita*. The dripping-wet plants are placed for approx. 16 hours in a controlled-environment cabinet at 20° C. and a relative atmospheric humidity of approx. 100%. They are then grown on in a greenhouse at a temperature of 22–25° C. and a relative atmospheric humidity of 50–70%.

After an incubation time of approx. 2 weeks, the fungus sporulates on the entire leaf area of the untreated control plants (100% infection), so that the test plants can be evaluated for disease. The disease incidence is expressed as diseased leaf area compared with the untreated, infected control plants.

Applied at 500 mg of active substance/l of spray mixture, the following substances are found to suppress disease completely:

Compounds according to Example No. 2, 9, 12, 17, 25, 30, 80, 93, 99.

BIOLOGICAL EXAMPLES (USE AS ACARICIDE/INSECTICIDE)

Example 1

Field beans (*Vicia faba*) heavily populated with the black bean aphid (*Aphis fabae*) are sprayed with aqueous dilutions of wettable powder concentrates with an active substance content of 250 ppm until the stage of beginning of runoff point is reached. The mortality of the aphids is determined after 3 days. A destruction of 100% can be achieved using the compounds according to Example No. 2, 9, 13, 17, 19, 25, 30, 55, 80, 93, 99, 106, 1741, 1749, 1750.

Example 2

Bean plants Phaseolus v.) are heavily populated with greenhouse spider mites (*Tetranychus urticae*, full population) were sprayed with the aqueous dilution of a wettable powder concentrate containing 250 ppm of the active substance in question.

The mortality of the mites was checked after 7 days. A destruction of 100% was achieved using the following compounds:

Compounds according to Example No. 2, 9, 10, 17, 19, 25, 30, 55, 80, 93, 94, 99, 106, 1741.

Example 3

Filter papers on which eggs of the large milkweed bug (*Oncopeltus fasciatus*) have been placed are treated with 0.5 ml portions of aqueous dilution of the test formulation. After the coating has dried on, the Petri dish is sealed, and the interior is kept at maximum atmospheric humidity. The dishes are kept at room temperature, and the oricidal and larvicidal activities are determined after 7 days. At an active substance content of 250 ppm, a mortality of 100% was obtained with the following compounds:

Compounds according to Example No. 2, 9, 10, 13, 17, 19, 25, 30, 55, 80, 93, 95, 99, 106, 312, 1741, 1749, 1750.

Example 4

1 ml portions of the test formulation, emulsified in water, are applied uniformly to the inside of the lid and the bottom of a Petri dish and, when the coating has dried on, batches of 10 imagines of the common housefly (*Musca domestica*) are introduced. The dishes are sealed and then kept at room temperature, the mortality of the test animals is determined after 3 hours. At 250 ppm (based on active substance content), the following preparations show a good activity (100% mortality) against the common housefly:

Compounds according to Example No. 9, 10, 17, 18, 19, 25, 55, 80, 93, 99, 106, 1741, 1750.

Example 5

Rice seed is placed into glass culture dishes containing cotton wool and germinated under moist conditions and, after the stem has grown to a length of approx. 8 cm, it is dipped together with the leaves into the test solution. The test solution is allowed to run off from the treated rice plants, and the plants are transferred to culture containers and populated with batches of 10 larvae (L3) of the species *Nilaparvata lugens*, the individual test concentrations being kept separate from each other. After the sealed culture containers have been kept at 21° C., the mortality of the cicada larvae can be determined after 4 days.

Under these test conditions, the compounds according to Example No. 9, 25, 30, 93, 99, 432 have a 100% activity at a test concentration of 250 ppm of the active ingredient.

Example 6

Wheat seed is pregerminated for 6 hours under water and then transferred to 10 ml glass test tubes and covered with in each case 2 ml of soil. 1 ml of water is added, and the plants remain in the glass culture dishes at room temperature (21° C.) until they have grown to a height of approx. 3 cm. Diabrotica larvae of a medium stage (batches of 10 specimens) are then transferred to the dishes and placed on the soil and, after 2 hours, 1 ml of the test liquid concentration to be tested is then pipetted onto the soil surface in the dishes.

After a standing time of 5 days under laboratory conditions (21° C.), the soil, or parts of the roots, are examined for live Diabrotica larvae, and the mortality is determined.

Under the test conditions mentioned, the compounds according to Example No. 2, 17, 19, 25, 93, 99 displayed an effectiveness of up to 100% at a test concentration of 250 ppm of the active ingredient.

Example 7

In vitro test with tropical cattle ticks (*Boophilus microplus*)

The following experimental set-up allowed the activity of the claimed compounds against ticks to be demonstrated:

To prepare a suitable preparation of active substance, the active substances were dissolved at a concentration of 10% (w/v) in a mixture composed of dimethylformamide (85 g), nonylphenol polyglycol ether (3 g) and oxethylated castor oil (7 g), and the resulting emulsion concentrates were diluted with water to a test concentration of 500 ppm.

Batches of ten females of the tropical tick *Boophilus microplus* which had sucked themselves full were immersed for five minutes in these active substance dilutions. The ticks were subsequently dried on filter paper and then attached, by their backs, to an adhesive film for the purpose of oviposition. The ticks were kept in an incubator at 28° C. and an atmospheric humidity of 90%.

As a control, female ticks were merely immersed in water. The inhibition of oviposition two weeks after the treatment was used to assess the effectiveness. 100% mean that no ticks have deposited eggs, 0% means that all ticks have deposited eggs.

In this test, a 100% inhibition of oviposition was caused by each of the compounds 10, 19, 30 and 106 at an active substance concentration of 500 ppm.

PREPARATION EXAMPLES

Example A 4-(4-tert-Butylcyclohexylamino)-5-chloro-6-ethylpyrimidine

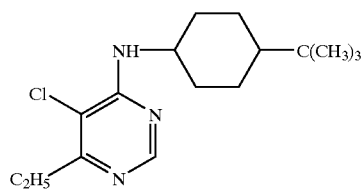

3.5 g (0.02 mol) of 4,5-dichloro-6-ethylpyrimidine and 7.8 g (0.05 mol) of 4-tert-butylcyclohexylamine were heated for two hours at 100° C., without solvent. After the mixture had cooled to room temperature, it was worked up using methylene chloride/water and the organic phase was dried and concentrated. The product was chromatographed on silica gel using petroleum ether/ethyl acetate 7:3 for further purification and for the separation of the cis/trans isomers.

The trans-cyclohexylamino derivative is eluted first (0.8 g of yellow oil solidifies, m.p. 94–96°). After a mixed fraction, which was discarded, pure cis-cyclohexylamino derivative was finally obtained (3.0 g of yellow oil).

Preparation of 4-tert-butylcyclohexylamine 312 g of 4-tert-butylcyclohexanone in 500 ml of ammonia-saturated methanol were hydrogenated at 100° C. and 100 bar in the presence of 10 g of Raney nickel. The catalyst was filtered off, the mixture was concentrated, and the crude product was purified on a thin-layer evaporator (105°/0.5 mm). 303 g of

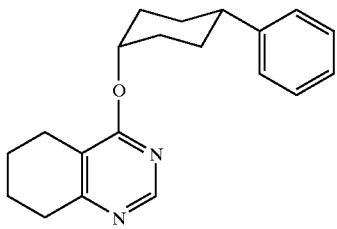

4-(cis-4-Phenyl-cyclohexyloxy)-5,6,7,8-tetrahydroquinazoline 0.5 g (16.7 mmol) of 80% NaH was added in portions to a solution of 1.85 g (105 mmol) of cis-4-phenylcyclohexanol in 30 ml of absolute THF. After this, the mixture was heated for 1 hour at 50° C., and 1.5 g (8.75 mmol) of 4-chloro-5,6,7,8-tetrahydroquinazoline, dissolved in 15 ml of absolute THF, were added dropwise. The reaction mixture was subsequently refluxed for 2 hours. After the mixture has cooled to room temperature, it was poured into saturated $NH_4Cl$ solution and this was extracted with ether, and the combined organic phase was dried over $MgSO_4$. The solvent was evaporated in vacuo, and the residue (2.7 g) was purified by flash chromatography over silica gel, using n-hexane/ethyl acetate (2:1). Concentration gave 1.5 g (50.2% of theory), colorless crystals, m.p. 109° C.

colorless liquid were obtained. The product is an isomer mixture in which the cis-cyclohexylamine derivative prevails.

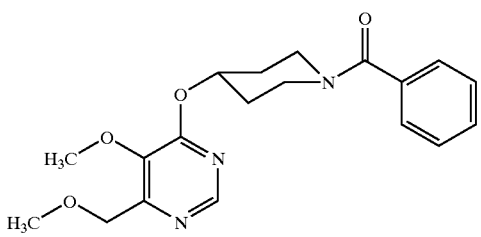

4-(N-Benzoyl-piperidyl-4-oxy)-5-methoxy-6-methoxymethyl-pyrimidine 2.9 g (14.3 mmol) of N-benzoyl-4-hydroxypiperidine (prepared by $NaBH_4$-reduction of N-benzoylpiperidine-4-one) were added to a suspension of 0.66 g (22 mmol) of 80% NaH in THF. This was then heated for 1 hour at 35–40° C., and 2.50 g (13.3 mmol) of 4-chloro-5-methoxy-6-methoxymethyl-pyrimidine were subsequently added without dilution. The reaction mixture was heated for 5 hours at 40° C., poured into a little saturated $NH_4Cl$ solution and extracted 5 times using ethyl acetate. The combined organic phases were dried over $MgSO_4$, and the residue (3.4 g) was purified by flash chromatography over silica gel using ethyl acetate. Concentration gave 0.6 g (13% of theory) of yellow oil, $n_D^{20}$=1.5815.

More examples can be found in Tables I–IV below.

| Abbreviations used | |
|---|---|
| $T^1$ | 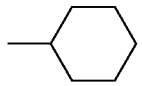 |
| $T^2$ | 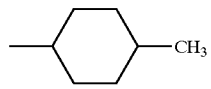 |
| $T^3$ | 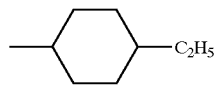 |
| $T^4$ | 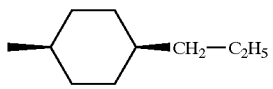 |
| $T^5$ | 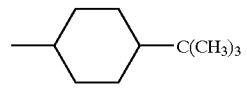 |
| $T^6$ | 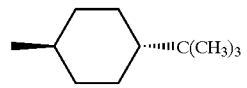 |
| $T^7$ | 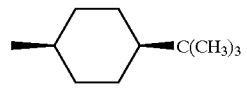 |

-continued
| Abbreviations used | |
|---|---|
| T⁸ | 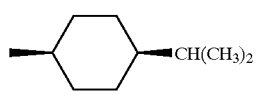 |
| T⁹ | 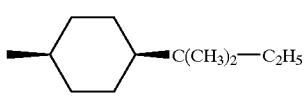 |
| T¹⁰ | 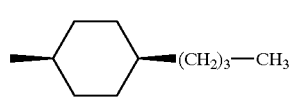 |
| T¹¹ | 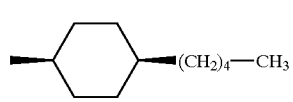 |
| T¹² | 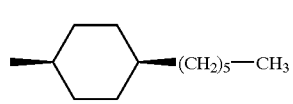 |
| T¹³ | 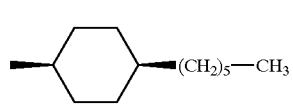 |
| T¹⁴ | 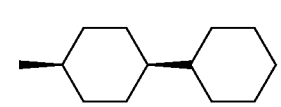 |
| T¹⁵ | 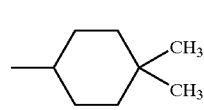 |
| T¹⁶ |  |
| T¹⁷ |  |
| T¹⁸ | 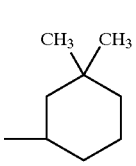 |
| T¹⁹ | 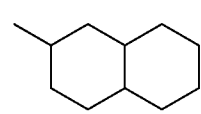 |
| T²⁰ | 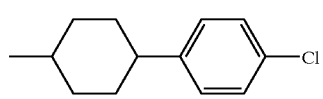 |
| T²¹ | 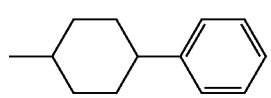 |

-continued
| Abbreviations used | |
|---|---|
| T$^{22}$ |  |
| T$^{23}$ | 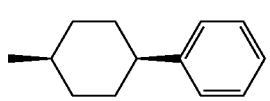 |
| T$^{24}$ | 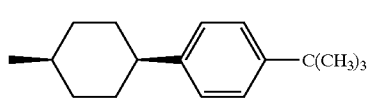 |
| T$^{25}$ | 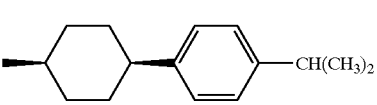 |
| T$^{26}$ | 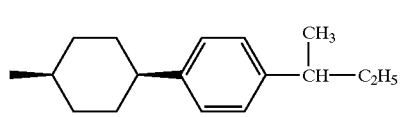 |
| T$^{27}$ | 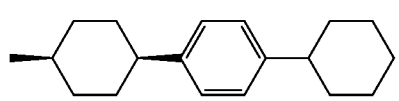 |
| T$^{28}$ | 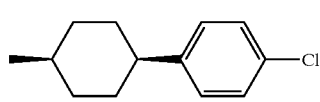 |
| T$^{29}$ | 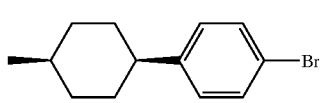 |
| T$^{30}$ | 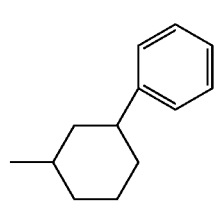 |
| T$^{31}$ | 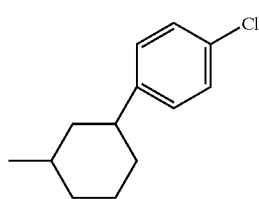 |
| T$^{32}$ | 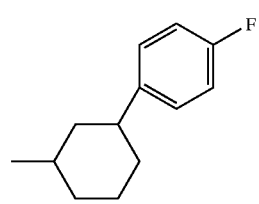 |

-continued
| Abbreviations used | |
|---|---|
| T$^{33}$ | 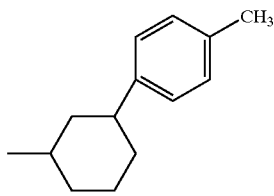 |
| T$^{34}$ | 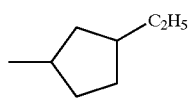 |
| T$^{35}$ | 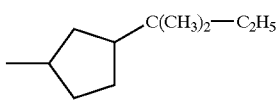 |
| T$^{36}$ | 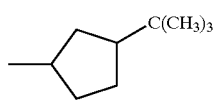 |
| T$^{37}$ | 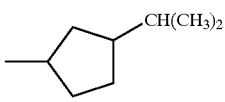 |
| T$^{38}$ | 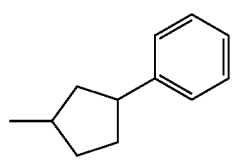 |
| T$^{39}$ | 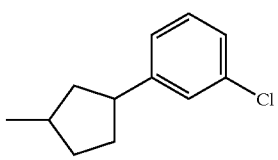 |
| T$^{40}$ | 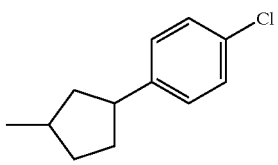 |
| T$^{41}$ | 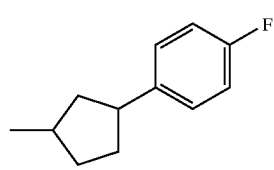 |
| T$^{42}$ | 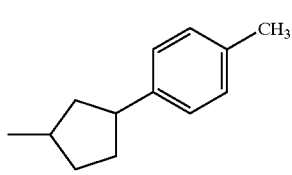 |

-continued
| Abbreviations used | |
|---|---|
| T⁴³ | 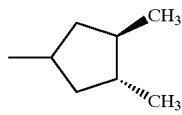 |
| T⁴⁴ | 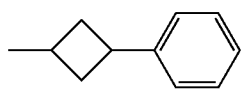 |
| T⁴⁵ | 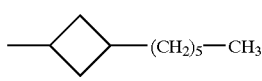 |
| T⁴⁶ | 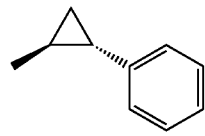 |
| T⁴⁷ | 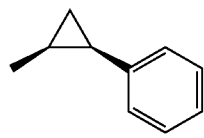 |
| T⁴⁸ | 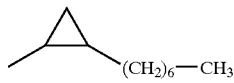 |
| T⁴⁹ | 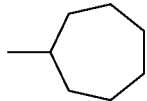 |
| T⁵⁰ | 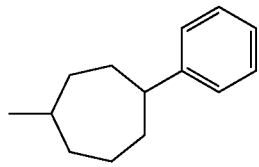 |
| T⁵¹ | 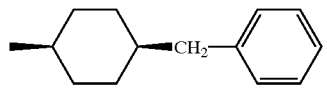 |
| T⁵² | 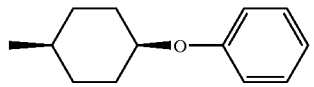 |
| T⁵³ | 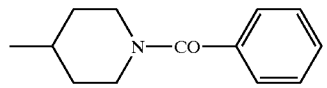 |
| T⁵⁴ |  |
| T⁵⁵ | 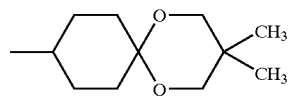 |

| Abbreviations used | |
|---|---|
| $T^{56}$ | 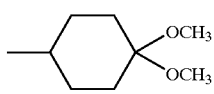 |
| $T^{57}$ | 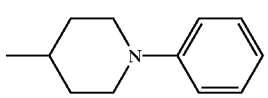 |
| $T^{58}$ | 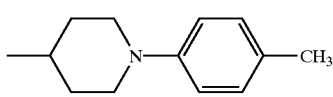 |
| $T^{59}$ | 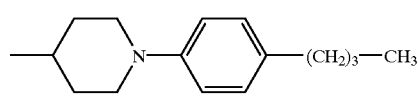 |
| $T^{60}$ | 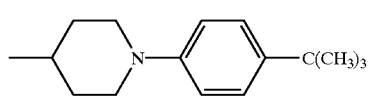 |
| $T^{61}$ | 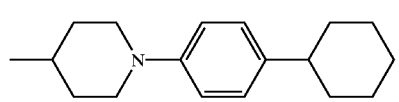 |
| $T^{62}$ | 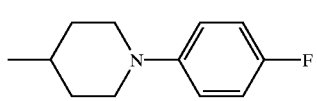 |
| $T^{63}$ | 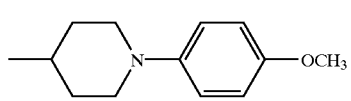 |
| $T^{64}$ | 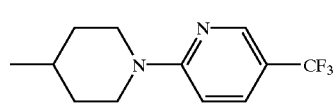 |
| $T^{65}$ | 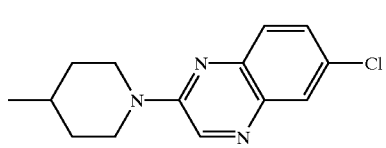 |
| $T^{66}$ | 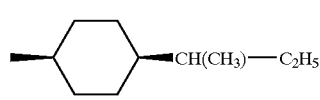 |
| $T^{67}$ | 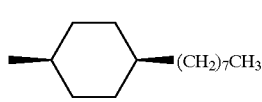 |
| $T^{68}$ | 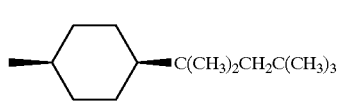 |
| $T^{69}$ | 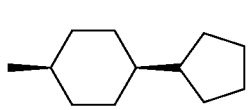 |

-continued
| Abbreviations used | |
|---|---|
| T[70] | 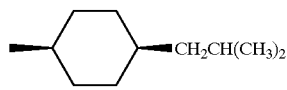 |
| T[71] | 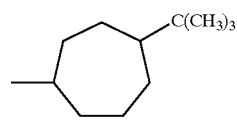 |
| T[72] | 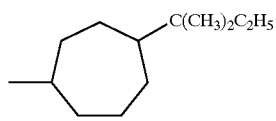 |
| T[73] | 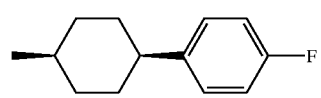 |
| T[74] | 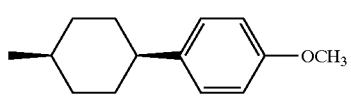 |
| T[75] | 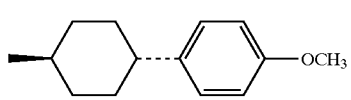 |
| T[76] | 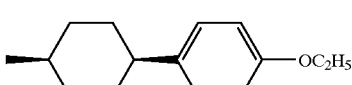 |
| T[77] | 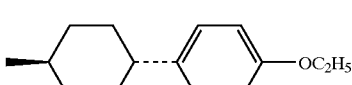 |
| T[78] | 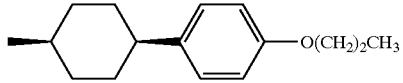 |
| T[79] | 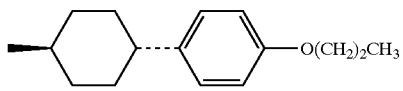 |
| T[80] | 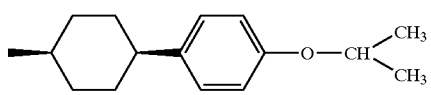 |
| T[81] | 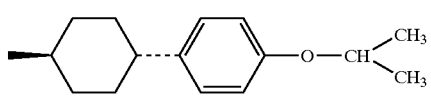 |
| T[82] | 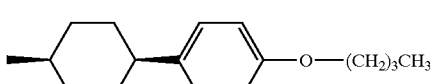 |
| T[83] | 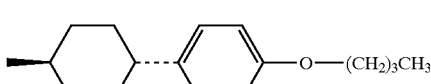 |

-continued
| Abbreviations used | |
|---|---|
| T⁸⁴ | 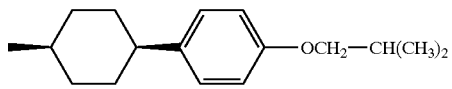 |
| T⁸⁵ | 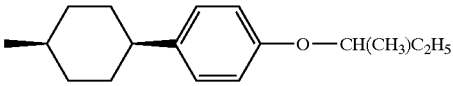 |
| T⁸⁶ | 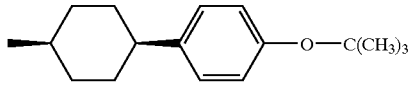 |
| T⁸⁷ | 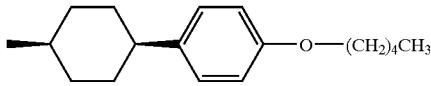 |
| T⁸⁸ | 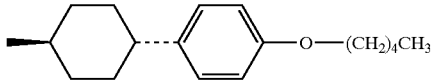 |
| T⁸⁹ | 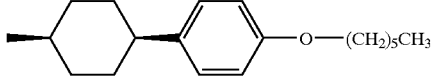 |
| T⁹⁰ | 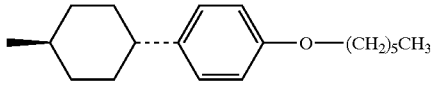 |
| T⁹¹ | 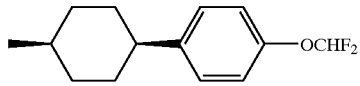 |
| T⁹² | 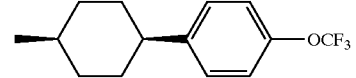 |
| T⁹³ | 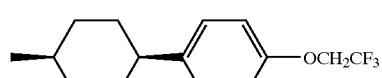 |
| T⁹⁴ | 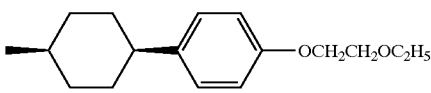 |
| T⁹⁵ | 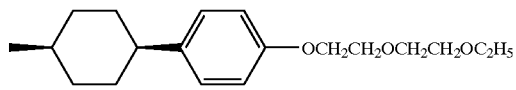 |
| T⁹⁶ | 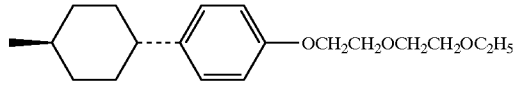 |
| T⁹⁷ | 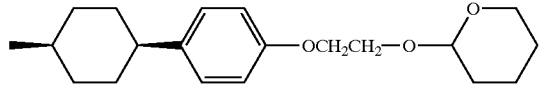 |
| T⁹⁸ | 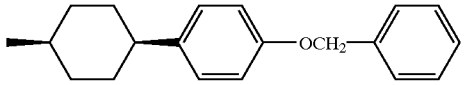 |

-continued
Abbreviations used
T⁹⁹ 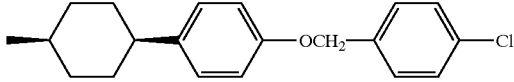
T¹⁰⁰ 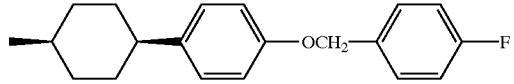
T¹⁰¹ 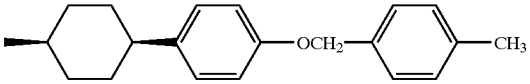
T¹⁰² 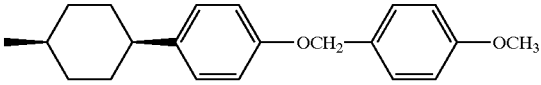
T¹⁰³ 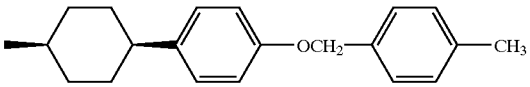
T¹⁰⁴ 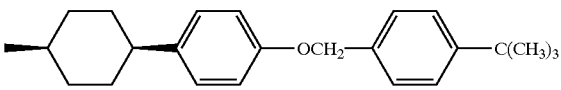
T¹⁰⁵ 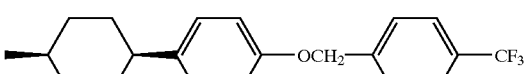
T¹⁰⁶ 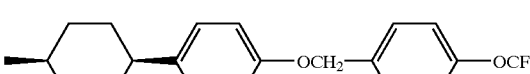
T¹⁰⁷ 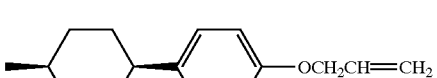
T¹⁰⁸ 
T¹⁰⁹ 
T¹¹⁰ 
T¹¹¹ 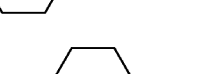
T¹¹² 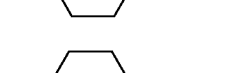
T¹¹³ 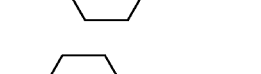

-continued
| Abbreviations used | |
|---|---|
| T$^{114}$ | 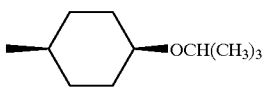 |
| T$^{115}$ | 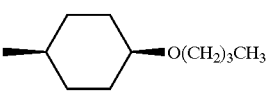 |
| T$^{116}$ | 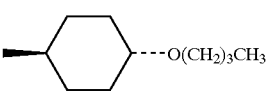 |
| T$^{117}$ | 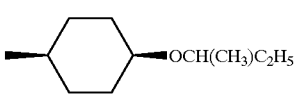 |
| T$^{118}$ | 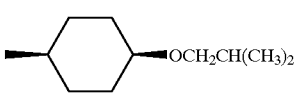 |
| T$^{119}$ | 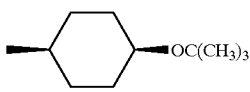 |
| T$^{120}$ | 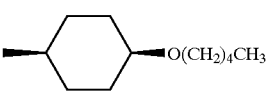 |
| T$^{121}$ | 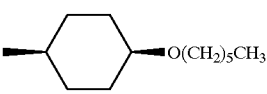 |
| T$^{122}$ | 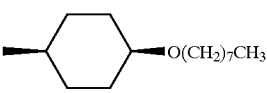 |
| T$^{123}$ | 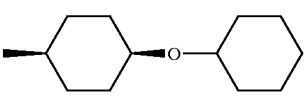 |
| T$^{124}$ | 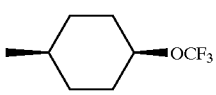 |
| T$^{125}$ | 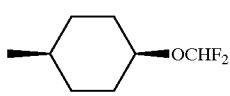 |
| T$^{126}$ | 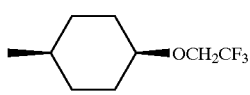 |
| T$^{127}$ | 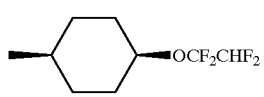 |
| T$^{128}$ | 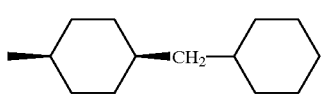 |

-continued
| Abbreviations used | |
|---|---|
| $T^{129}$ |  |
| $T^{130}$ | 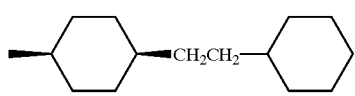 |
| $T^{131}$ | 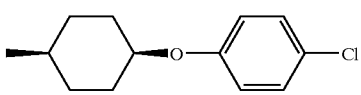 |
| $T^{132}$ | 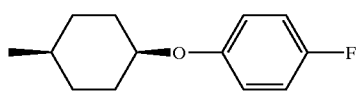 |
| $T^{133}$ | 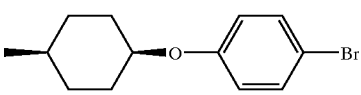 |
| $T^{134}$ | 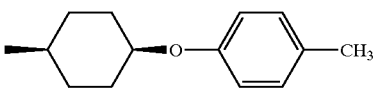 |
| $T^{135}$ | 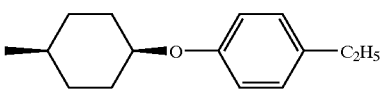 |
| $T^{136}$ | 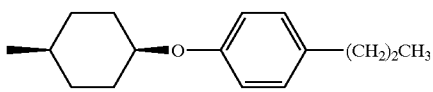 |
| $T^{137}$ | 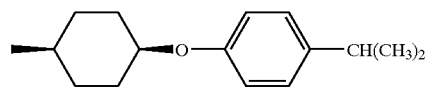 |
| $T^{138}$ | 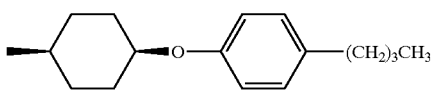 |
| $T^{139}$ | 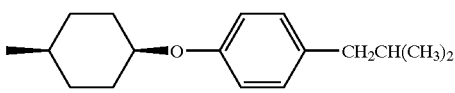 |
| $T^{140}$ | 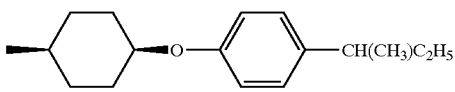 |
| $T^{141}$ | 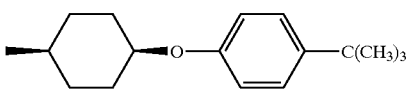 |
| $T^{142}$ | 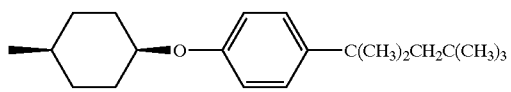 |
| $T^{143}$ | 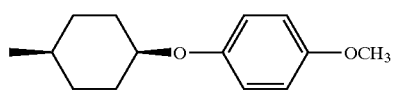 |

-continued
| Abbreviations used | |
|---|---|
| T144 | 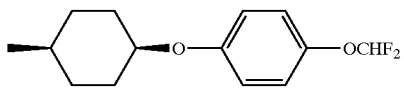 |
| T145 | 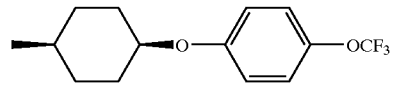 |
| T146 | 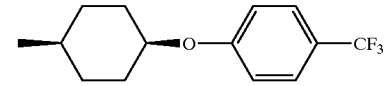 |
| T147 | 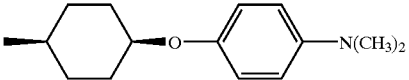 |
| T148 | 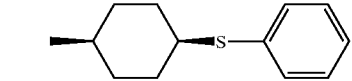 |
| T149 | 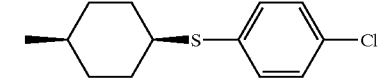 |
| T150 | 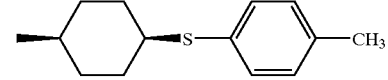 |
| T151 | 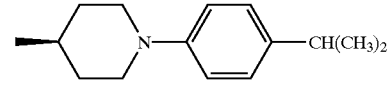 |
| T152 | 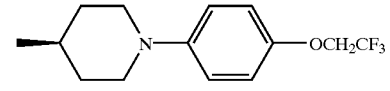 |
| T153 | 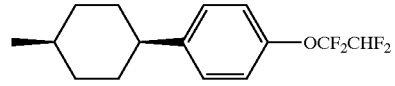 |
| T154 | 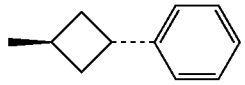 |
| T155 | 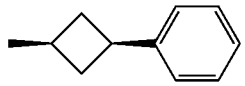 |
| T156 | 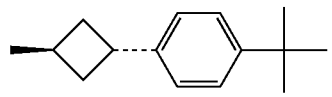 |
| T157 | 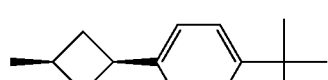 |
| T158 | 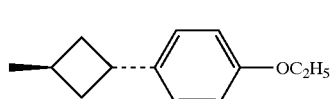 |

-continued
| Abbreviations used | |
|---|---|
| T$^{159}$ | 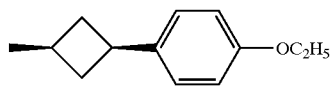 |
| T$^{160}$ |  |
| T$^{161}$ | 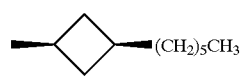 |
| T$^{162}$ | 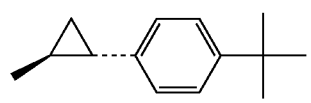 |
| T$^{163}$ | 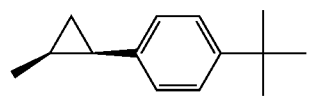 |
| T$^{164}$ | 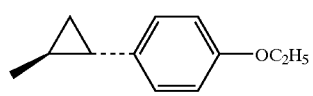 |
| T$^{165}$ | 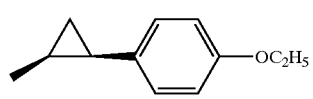 |
| T$^{166}$ | 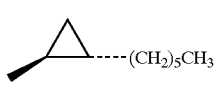 |
| T$^{167}$ | 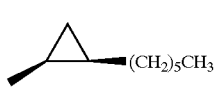 |
| T$^{168}$ | 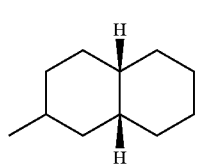 |
| T$^{169}$ | 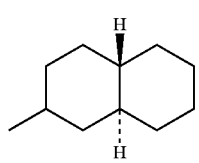 |
| T$^{170}$ | 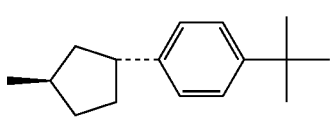 |
| T$^{171}$ | 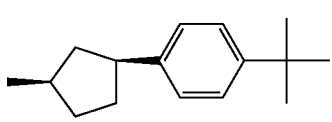 |

-continued
| Abbreviations used | |
|---|---|
| T[172] | 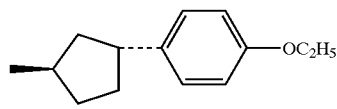 |
| T[173] | 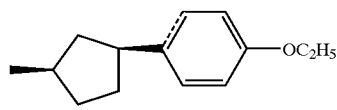 |
| T[174] | 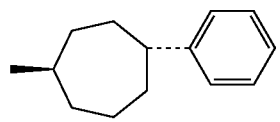 |
| T[175] | 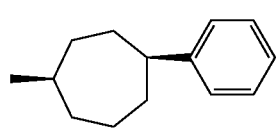 |
| T[176] | 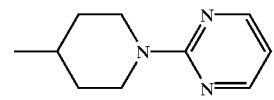 |
| T[177] | 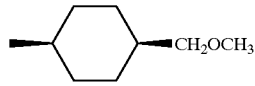 |
| T[178] | 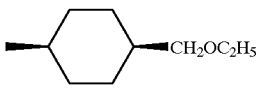 |
| T[179] | 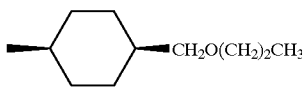 |
| T[180] | 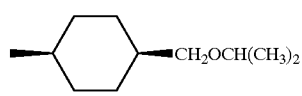 |
| T[181] | 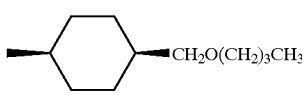 |
| T[182] | 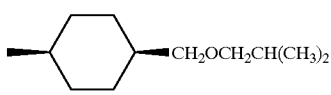 |
| T[183] | 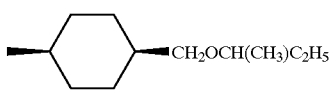 |
| T[184] | 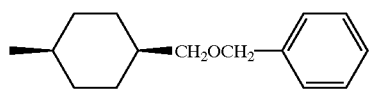 |
| T[185] |  |

-continued
| Abbreviations used | |
|---|---|
| T¹⁸⁶ | 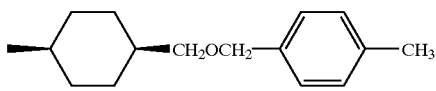 |
| T¹⁸⁷ | 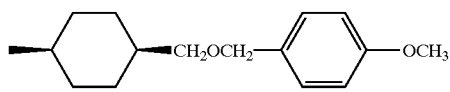 |
| T¹⁸⁸ | 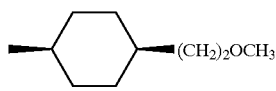 |
| T¹⁸⁹ | 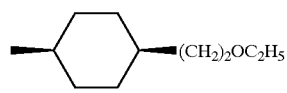 |
| T¹⁹⁰ | 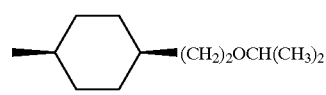 |
| T¹⁹¹ | 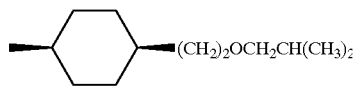 |
| T¹⁹² | 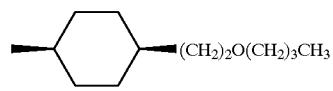 |
| T¹⁹³ | 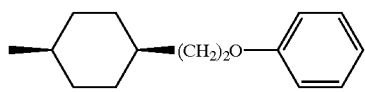 |
| T¹⁹⁴ | 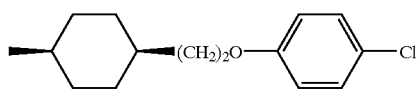 |
| T¹⁹⁵ | 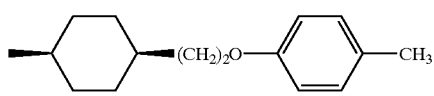 |
| T¹⁹⁶ | 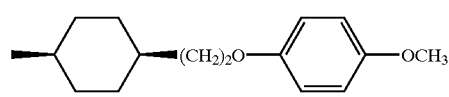 |
| T¹⁹⁷ | 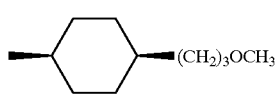 |
| T¹⁹⁸ | 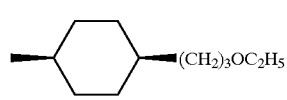 |
| T¹⁹⁹ | 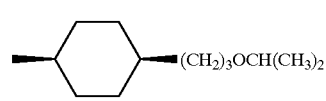 |
| T²⁰⁰ | 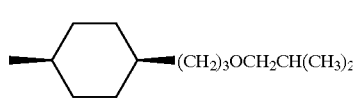 |

-continued
| Abbreviations used | |
|---|---|
| T²⁰¹ | 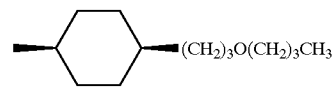 |
| T²⁰² | 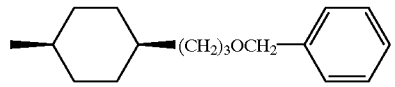 |
| T²⁰³ | 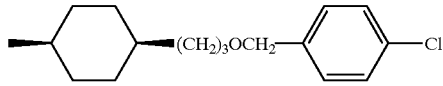 |
| T²⁰⁴ | 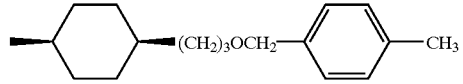 |
| T²⁰⁵ | 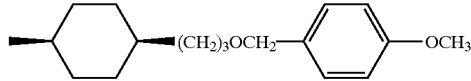 |
| T²⁰⁶ | 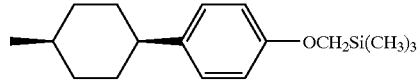 |
| T²⁰⁷ | 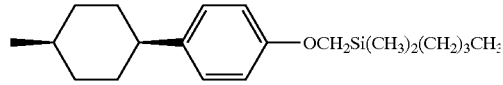 |
| T²⁰⁸ | 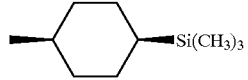 |
| T²⁰⁹ | 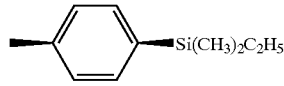 |
| T²¹⁰ | 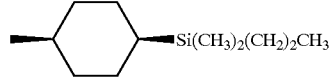 |
| T²¹¹ | 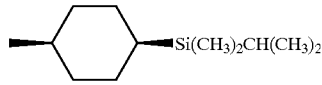 |
| T²¹² | 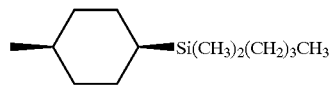 |
| T²¹³ |  |
| T²¹⁴ |  |
| T²¹⁵ | 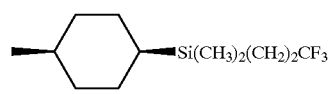 |

| Abbreviations used | |
|---|---|
| T216 | 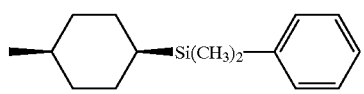 |
| T217 | 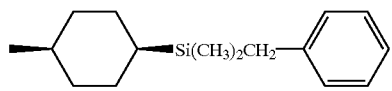 |
| T218 | 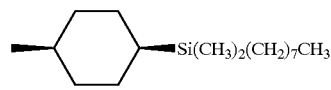 |
| T219 | 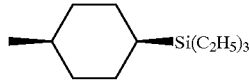 |
| T220 | 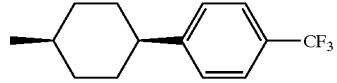 |
| T221 | 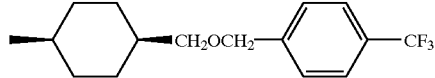 |
| T222 | 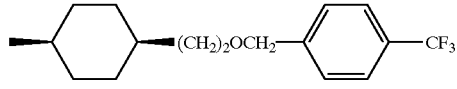 |
| T223 | 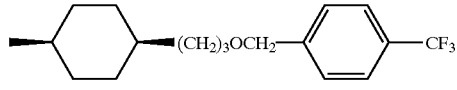 |
| T224 | 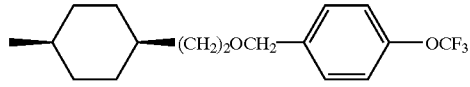 |
| T225 | 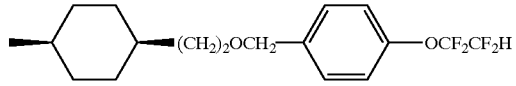 |
| T226 | 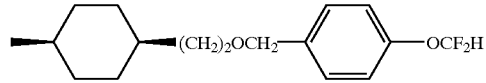 |
| T227 | 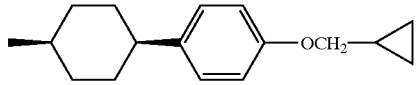 |
| T228 |  |
| T229 |  |
| T230 | 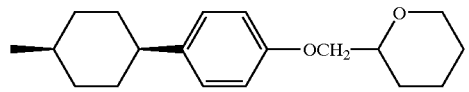 |

-continued
| Abbreviations used | |
|---|---|
| T²³¹ | 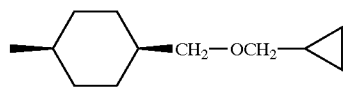 |
| T²³² | 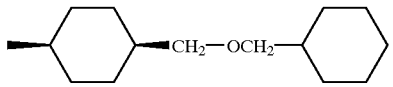 |
| T²³³ | 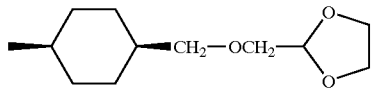 |
| T²³⁴ | 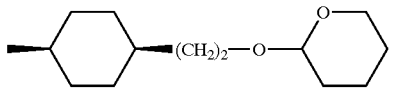 |
| T²³⁵ | 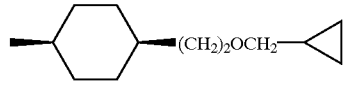 |
| T²³⁶ | 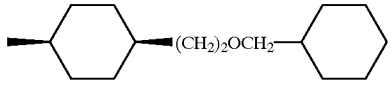 |
| T²³⁷ | 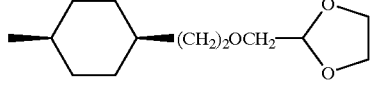 |
| T²³⁸ | 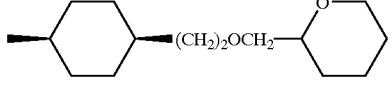 |
| T²³⁹ | 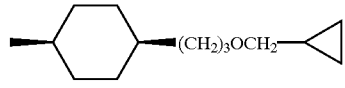 |
| T²⁴⁰ | 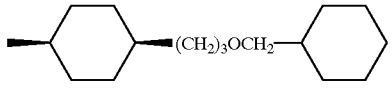 |
| T²⁴¹ | 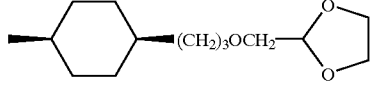 |
| T²⁴² | 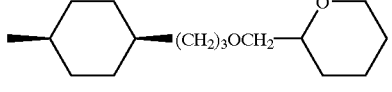 |
| T²⁴³ | 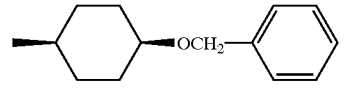 |
| T²⁴⁴ | 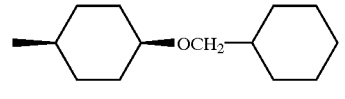 |
| T²⁴⁵ | 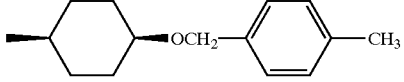 |

-continued

| Abbreviations used | |
|---|---|
| $T^{246}$ | cyclohexyl-OCH$_2$-phenyl-Cl |
| $T^{247}$ | cyclohexyl-OCH$_2$-phenyl-OCH$_3$ |
| $T^{248}$ | cyclohexyl-OCH$_2$-cyclopropyl |

TABLE I $$\text{pyrimidine with } X\text{—}E\text{—}Q \text{ at position 4, } R^3 \text{ at 5, } R^2 \text{ at 6, } R^1 \text{ at 2}$$

| Example No. | $R^1$ | $R^2$ | $R^3$ | X | E | Q | M.p. [° C.] |
|---|---|---|---|---|---|---|---|
| 1 | H | CH$_2$OCH$_3$ | OCH$_3$ | NH | — | $T^1$ | 76–78 |
| 2 | H | CH$_2$OCH$_3$ | OCH$_3$ | NH | — | $T^2$ | oil |
| 3 | H | CH$_2$OCH$_3$ | OCH$_3$ | NH | — | $T^3$ | oil |
| 4 | H | CH$_2$OCH$_3$ | OCH$_3$ | NH | — | $T^4$ | oil |
| 5 | H | CH$_2$OCH$_3$ | OCH$_3$ | O | — | $T^4$ | |
| 6 | H | —(CH$_2$)$_4$— | | O | — | $T^4$ | |
| 7 | H | C$_2$H$_5$ | Cl | NH | — | $T^4$ | oil |
| 8 | H | C$_2$H$_5$ | Cl | O | — | $T^4$ | |
| 9 | H | CH$_2$OCH$_3$ | OCH$_3$ | NH | — | $T^5$, cis/trans = 1:2 | oil |
| 10 | H | —(CH$_2$)$_4$— | | NH | — | $T^5$, cis/trans = 2:1 | oil |
| 11 | H | —(CH$_2$)$_4$— | | O | — | $T^6$ | 104 |
| 12 | H | CH$_2$OCH$_3$ | OCH$_3$ | NH | — | $T^6$ | 76–77 |
| 13 | H | CH$_2$OCH$_3$ | OCH$_3$ | O | — | $T^6$ | oil |
| 14 | H | C$_2$H$_5$ | Cl | NH | — | $T^6$ | 94–96 |
| 15 | H | C$_2$H$_5$ | Cl | O | — | $T^7$ | oil |
| 16 | H | C$_2$H$_5$ | Cl | NH | — | $T^7$ | oil |
| 17 | H | CH$_2$OCH$_3$ | OCH$_3$ | NH | — | $T^7$ | oil |
| 18 | H | CH$_2$OCH$_3$ | OCH$_3$ | O | — | $T^7$ | oil |
| 19 | H | —(CH$_2$)$_4$— | | O | — | $T^7$ | oil |
| 20 | CH$_3$ | C$_2$H$_5$ | Cl | NH | — | $T^7$ | |
| 21 | CH$_3$ | C$_2$H$_5$ | Cl | O | — | $T^7$ | |
| 22 | H | CH$_2$OCH$_3$ | OCH$_3$ | NH | CH$_2$ | $T^5$ | oil |
| 23 | H | CH$_2$OCH$_3$ | OCH$_3$ | O | " | $T^5$ | oil |
| 24 | H | —(CH$_2$)$_4$— | | O | CH$_2$ | $T^5$ | oil |
| 25 | H | CH$_2$OCH$_3$ | OCH$_3$ | NH | H | $T^8$ | oil |
| 26 | H | CH$_2$OCH$_3$ | OCH$_3$ | O | H | $T^8$ | oil |
| 27 | H | C$_2$H$_5$ | Cl | NH | H | $T^8$ | oil |
| 28 | H | C$_2$H$_5$ | Cl | O | H | $T^8$ | oil |
| 29 | H | —(CH$_2$)$_4$— | | O | H | $T^8$ | oil |
| 30 | H | CH$_2$OCH$_3$ | OCH$_3$ | NH | H | $T^9$ | oil |
| 31 | H | CH$_2$OCH$_3$ | OCH$_3$ | O | H | $T^9$ | oil |
| 32 | H | C$_2$H$_5$ | Cl | NH | H | $T^9$ | oil |
| 33 | H | C$_2$H$_5$ | Cl | O | H | $T^9$ | |
| 34 | H | —(CH$_2$)$_4$— | | O | H | $T^9$ | oil |
| 35 | H | CH$_2$OCH$_3$ | OCH$_3$ | NH | H | $T^{10}$ | oil |
| 36 | H | CH$_2$OCH$_3$ | OCH$_3$ | O | H | $T^{10}$ | |
| 37 | H | C$_2$H$_5$ | Cl | NH | H | $T^{10}$ | oil |
| 38 | H | C$_2$H$_5$ | Cl | O | H | $T^{10}$ | |
| 39 | H | —(CH$_2$)$_4$— | | O | H | $T^{10}$ | |
| 40 | H | CH$_2$OCH$_3$ | OCH$_3$ | NH | H | $T^{11}$ | oil |
| 41 | H | CH$_2$OCH$_3$ | OCH$_3$ | O | H | $T^{11}$ | |
| 42 | H | —(CH$_2$)$_4$— | | O | H | $T^{11}$ | |
| 43 | H | C$_2$H$_5$ | Cl | NH | — | $T^{11}$ | oil |
| 44 | H | C$_2$H$_5$ | Cl | O | — | $T^{11}$ | |
| 45 | H | CH$_2$OCH$_3$ | OCH$_3$ | NH | — | $T^{12}$ | |
| 46 | H | CH$_2$OCH$_3$ | OCH$_3$ | O | — | $T^{12}$ | |

TABLE I-continued

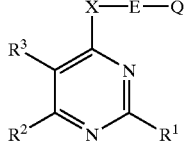

| Example No. | $R^1$ | $R^2$ | $R^3$ | X | E | Q | M.p. [°C.] |
|---|---|---|---|---|---|---|---|
| 47 | H | $C_2H_5$ | Cl | NH | — | $T^{12}$ | |
| 48 | H | $C_2H_5$ | Cl | O | — | $T^{12}$ | |
| 49 | H | —$(CH_2)_4$— | | O | — | $T^{12}$ | |
| 50 | H | $CH_2OCH_3$ | $OCH_3$ | NH | — | $T^{13}$ | |
| 51 | H | $CH_2OCH_3$ | $OCH_3$ | O | — | $T^{13}$ | |
| 52 | H | $C_2H_5$ | Cl | NH | — | $T^{13}$ | |
| 53 | H | $C_2H_5$ | Cl | O | — | $T^{13}$ | |
| 54 | H | —$(CH_2)_4$— | | O | — | $T^{13}$ | oil |
| 55 | H | $CH_2OCH_3$ | $OCH_3$ | NH | — | $T^{14}$ | oil |
| 56 | H | $CH_2OCH_3$ | $OCH_3$ | O | — | $T^{14}$ | |
| 57 | H | $C_2H_5$ | Cl | NH | — | $T^{14}$ | 80–81 |
| 58 | H | $C_2H_5$ | Cl | O | — | $T^{14}$ | |
| 59 | H | —$(CH_2)_4$— | | O | — | $T^{14}$ | 69 |
| 60 | H | $CH_2OCH_3$ | $OCH_3$ | NH | — | $T^{15}$ | 78–80 |
| 61 | | $CH_2OCH_3$ | $OCH_3$ | O | — | $T^{15}$ | |
| 62 | | $C_2H_5$ | $OCH_3$ | NH | — | $T^{15}$ | |
| 63 | | $C_2H_5$ | $OCH_3$ | O | — | $T^{15}$ | |
| 64 | | —$(CH_2)_4$— | | O | — | $T^{15}$ | |
| 65 | | $CH_2OCH_3$ | $OCH_3$ | NH | — | $T^{16}$ | |
| 66 | H | $CH_2OCH_3$ | $OCH_3$ | O | — | $T^{16}$ | |
| 67 | H | $C_2H_5$ | Cl | NH | — | $T^{16}$ | |
| 68 | H | $C_2H_5$ | Cl | O | — | $T^{16}$ | |
| 69 | H | —$(CH_2)_4$— | | O | — | $T^{16}$ | |
| 70 | H | $CH_2OCH_3$ | Cl | NH | — | $T^{17}$ | |
| 71 | H | $CH_2OCH_3$ | Cl | O | — | $T^{17}$ | |
| 72 | H | $C_2H_5$ | Cl | NH | — | $T^{17}$ | |
| 73 | H | $C_2H_5$ | Cl | O | — | $T^{17}$ | |
| 74 | H | —$(CH_2)_4$— | | O | — | $T^{17}$ | |
| 75 | H | $CH_2OCH_3$ | $OCH_3$ | NH | — | $T^{18}$ | 69–70 |
| 76 | H | $CH_2OCH_3$ | $OCH_3$ | O | — | $T^{18}$ | |
| 77 | H | $C_2H_5$ | Cl | NH | — | $T^{18}$ | |
| 78 | H | $C_2H_5$ | Cl | O | — | $T^{18}$ | |
| 79 | H | —$(CH_2)_4$— | | O | — | $T^{18}$ | |
| 80 | H | $CH_2OCH_3$ | $OCH_3$ | NH | — | $T^{19}$ | oil |
| 81 | H | $CH_2OCH_3$ | $OCH_3$ | O | — | $T^{19}$ | oil |
| 82 | H | $C_2H_5$ | Cl | NH | — | $T^{19}$ | oil |
| 83 | H | $C_2H_5$ | Cl | O | — | $T^{19}$ | |
| 84 | H | —$(CH_2)_4$— | | O | — | $T^{19}$ | oil |
| 85 | H | $CH_2OCH_3$ | $OCH_3$ | NH | $CH_2$ | $T^5$ | oil |
| 86 | H | $CH_2OCH_3$ | $OCH_3$ | O | " | $T^5$ | oil |
| 87 | | —$(CH_2)_4$— | | O | " | $T^5$ | oil |
| 88 | H | $CH_2OCH_3$ | $OCH_3$ | NH | $CHCH_3$ | $T^{20}$ | oil |
| 89 | H | $CH_2OCH_3$ | $OCH_3$ | O | " | $T^{20}$ | |
| 90 | H | $C_2H_5$ | Cl | NH | " | $T^{20}$ | |
| 91 | H | $C_2H_5$ | Cl | O | " | $T^{20}$ | |
| 92 | H | —$(CH_2)_4$— | | O | " | $T^{20}$ | oil |
| 93 | H | $CH_2OCH_3$ | $OCH_3$ | NH | — | $T^{21}$, cis/trans = 2:1 | oil |
| 94 | H | $CH_2OCH_3$ | $OCH_3$ | NH | — | $T^{22}$ | 70–72 |
| 95 | H | $CH_2OCH_3$ | $OCH_3$ | O | — | $T^{22}$ | 37 |
| 96 | H | $C_2H_5$ | Cl | NH | — | $T^{22}$ | 79–80 |
| 97 | H | —$(CH_2)_4$— | | NH | — | $T^{22}$ | 165–166 |
| 98 | H | —$(CH_2)_4$— | | O | — | $T^{22}$ | 112 |
| 99 | H | $CH_2OCH_3$ | $OCH_3$ | NH | — | $T^{23}$ | 82–84 |
| 100 | H | $CH_2OCH_3$ | $OCH_3$ | O | — | $T^{23}$ | 109 |
| 101 | H | $C_2H_5$ | Cl | NH | — | $T^{23}$ | 74–75 |
| 102 | H | $C_2H_5$ | Cl | O | — | $T^{23}$ | |
| 103 | $CH_3$ | $C_2H_5$ | Cl | NH | — | $T^{23}$ | |
| 104 | $CH_3$ | $C_2H_5$ | Cl | O | — | $T^{23}$ | |
| 105 | H | —$(CH_2)_4$— | | NH | — | $T^{23}$ | 121–123 |
| 106 | H | —$(CH_2)_4$— | | O | — | $T^{23}$ | 109 |
| 107 | H | $C_2H_5$ | $C_2H_5$ | O | — | $T^{23}$ | |
| 108 | H | $CH_2OCH_3$ | $OCH_3$ | NH | — | $T^{24}$ | oil |
| 109 | H | $CH_2OCH_3$ | $OCH_3$ | O | — | $T^{24}$ | |
| 110 | H | $C_2H_5$ | Cl | NH | — | $T^{24}$ | 63–65 |
| 111 | H | $C_2H_5$ | Cl | O | — | $T^{24}$ | |
| 112 | H | —$(CH_2)_4$— | | O | — | $T^{24}$ | 93–94 |
| 113 | H | $CH_2OCH_3$ | $OCH_3$ | NH | — | $T^{25}$ | |

TABLE I-continued

![structure: pyrimidine with X-E-Q at position 4, R³ at 5, R² at 6, R¹ at 2]

| Example No. | R¹ | R² | R³ | X | E | Q | M.p. [° C.] |
|---|---|---|---|---|---|---|---|
| 114 | H | CH₂OCH₃ | OCH₃ | O | — | T²⁵ | |
| 115 | H | C₂H₅ | Cl | NH | — | T²⁵ | |
| 116 | H | C₂H₅ | Cl | NH | — | T²⁵ | |
| 117 | H | —(CH₂)₄— | | O | — | T²⁵ | |
| 118 | H | CH₂OCH₃ | OCH₃ | NH | — | T²⁶ | |
| 119 | H | CH₂OCH₃ | OCH₃ | O | — | T²⁶ | |
| 120 | H | C₂H₅ | Cl | NH | — | T²⁶ | |
| 121 | H | C₂H₅ | Cl | O | — | T²⁶ | |
| 122 | H | —(CH₂)₄— | | O | — | T²⁶ | |
| 123 | H | CH₂OCH₃ | OCH₃ | NH | — | T²⁷ | |
| 124 | H | CH₂OCH₃ | OCH₃ | O | — | T²⁷ | |
| 125 | H | C₂H₅ | Cl | NH | — | T²⁷ | |
| 126 | H | C₂H₅ | Cl | O | — | T²⁷ | |
| 127 | H | —(CH₂)₄— | | O | — | T²⁷ | |
| 128 | H | CH₂OCH₃ | Cl | NH | — | T²⁸ | |
| 129 | H | CH₂OCH₃ | Cl | O | — | T²⁸ | |
| 130 | H | C₂H₅ | Cl | NH | — | T²⁸ | |
| 131 | H | C₂H₅ | Cl | O | — | T²⁸ | |
| 132 | H | —(CH₂)₄— | | O | — | T²⁸ | |
| 133 | H | CH₂OCH₃ | OCH₃ | NH | — | T²⁹ | |
| 134 | H | CH₂OCH₃ | OCH₃ | O | — | T²⁹ | |
| 135 | H | C₂H₅ | Cl | NH | — | T²⁹ | |
| 136 | H | C₂H₅ | Cl | NH | — | T²⁹ | |
| 137 | H | —(CH₂)₄— | | O | — | T²⁹ | |
| 138 | H | CH₂OCH₃ | OCH₃ | NH | — | T³⁰ | oil |
| 139 | H | C₂H₅ | Cl | NH | — | T³⁰ | oil |
| 140 | H | CH₂OCH₃ | OCH₃ | NH | — | T³¹ | |
| 141 | H | CH₂OCH₃ | OCH₃ | O | — | T³¹ | |
| 142 | H | C₂H₅ | Cl | NH | — | T³¹ | |
| 143 | H | C₂H₅ | Cl | O | — | T³¹ | |
| 144 | H | —(CH₂)₄— | | O | — | T³¹ | |
| 145 | H | CH₂OCH₃ | OCH₃ | NH | — | T³² | |
| 146 | H | CH₂OCH₃ | OCH₃ | O | — | T³² | |
| 147 | H | C₂H₅ | Cl | NH | — | T³² | |
| 148 | H | C₂H₅ | Cl | O | — | T³² | |
| 149 | H | —(CH₂)₄— | | O | — | T³² | |
| 150 | H | CH₂OCH₃ | OCH₃ | NH | | T³³ | |
| 151 | H | CH₂OCH₃ | OCH₃ | O | | T³³ | |
| 152 | H | C₂H₅ | Cl | NH | | T³³ | |
| 153 | H | C₂H₅ | Cl | O | | T³³ | |
| 154 | H | —(CH₂)₄— | | O | | T³³ | |
| 155 | H | CH₂OCH₃ | OCH₃ | NH | — | T³⁴ | oil |
| 156 | H | CH₂OCH₃ | OCH₃ | NH | — | T³⁵ | oil |
| 157 | H | CH₂OCH₃ | OCH₃ | O | — | T³⁵ | |
| 158 | H | C₂H₅ | Cl | NH | — | T³⁵ | |
| 159 | H | C₂H₅ | Cl | O | — | T³⁵ | |
| 160 | H | —(CH₂)₄— | | O | — | T³⁵ | |
| 161 | H | CH₂OCH₃ | OCH₃ | NH | — | T³⁶ | |
| 162 | H | CH₂OCH₃ | OCH₃ | O | — | T³⁶ | |
| 163 | H | C₂H₅ | Cl | NH | — | T³⁶ | |
| 164 | H | C₂H₅ | Cl | O | — | T³⁶ | |
| 165 | H | —(CH₂)₄— | | O | — | T³⁶ | |
| 166 | H | CH₂OCH₃ | OCH₃ | NH | — | T³⁷ | |
| 167 | H | CH₂OCH₃ | OCH₃ | O | — | T³⁷ | |
| 168 | H | C₂H₅ | Cl | NH | — | T³⁷ | |
| 169 | H | C₂H₅ | Cl | O | — | T³⁷ | |
| 170 | H | —(CH₂)₄— | | O | — | T³⁷ | |
| 171 | H | CH₂OCH₃ | OCH₃ | NH | — | T³⁸ | |
| 172 | H | CH₂OCH₃ | OCH₃ | O | — | T³⁸ | |
| 173 | H | C₂H₅ | Cl | NH | — | T³⁸ | |
| 174 | H | C₂H₅ | Cl | O | — | T³⁸ | |
| 175 | H | —(CH₂)₄— | | O | — | T³⁸ | |
| 176 | H | CH₂OCH₃ | OCH₃ | NH | — | T³⁹ | |
| 177 | H | CH₂OCH₃ | OCH₃ | O | — | T³⁹ | |
| 178 | H | C₂H₅ | Cl | NH | — | T⁴⁰ | |
| 179 | H | C₂H₅ | Cl | O | — | T⁴⁰ | |
| 180 | H | —(CH₂)₄— | | O | — | T⁴⁰ | |

TABLE I-continued $$\underset{R^2}{\overset{R^3}{\text{pyrimidine with X-E-Q at 4, R}^1\text{ at 2}}}$$

| Example No. | R$^1$ | R$^2$ | R$^3$ | X | E | Q | M.p. [° C.] |
|---|---|---|---|---|---|---|---|
| 181 | H | CH$_2$OCH$_3$ | OCH$_3$ | NH | — | T$^{41}$ | |
| 182 | H | CH$_2$OCH$_3$ | OCH$_3$ | O | — | T$^{41}$ | |
| 183 | H | C$_2$H$_5$ | Cl | NH | — | T$^{41}$ | |
| 184 | H | C$_2$H$_5$ | Cl | O | — | T$^{41}$ | |
| 185 | H | —(CH$_2$)$_4$— | | O | — | T$^{41}$ | |
| 186 | H | CH$_2$OCH$_3$ | OCH$_3$ | NH | — | T$^{42}$ | |
| 187 | H | CH$_2$OCH$_3$ | OCH$_3$ | O | — | T$^{42}$ | |
| 188 | H | C$_2$H$_5$ | Cl | NH | — | T$^{42}$ | |
| 189 | H | C$_2$H$_5$ | Cl | O | — | T$^{42}$ | |
| 190 | H | —(CH$_2$)$_4$— | | O | — | T$^{43}$ | |
| 191 | H | CH$_2$OCH$_3$ | OCH$_3$ | NH | — | T$^{43}$ | |
| 192 | H | CH$_2$OCH$_3$ | OCH$_3$ | NH | — | T$^{44}$ | oil |
| 193 | H | CH$_2$OCH$_3$ | OCH$_3$ | O | — | T$^{44}$ | |
| 194 | H | C$_2$H$_5$ | Cl | NH | — | T$^{44}$ | |
| 195 | H | C$_2$H$_5$ | Cl | O | — | T$^{44}$ | |
| 196 | H | —(CH$_2$)$_4$— | | O | — | T$^{44}$ | |
| 197 | H | CH$_2$OCH$_3$ | OCH$_3$ | NH | — | T$^{45}$ | |
| 198 | H | CH$_2$OCH$_3$ | OCH$_3$ | O | — | T$^{45}$ | |
| 199 | H | C$_2$H$_5$ | Cl | NH | — | T$^{45}$ | |
| 200 | H | C$_2$H$_5$ | Cl | O | — | T$^{45}$ | |
| 201 | H | —(CH$_2$)$_4$— | | O | — | T$^{45}$ | |
| 202 | H | CH$_2$OCH$_3$ | OCH$_3$ | NH | — | T$^{46}$ | 60–62 |
| 203 | H | CH$_2$OCH$_3$ | OCH$_3$ | NH | — | T$^{47}$ | |
| 204 | H | C$_2$H$_5$ | Cl | NH | — | T$^{47}$ | |
| 205 | H | CH$_2$OCH$_3$ | OCH$_3$ | NH | — | T$^{48}$ | |
| 206 | H | C$_2$H$_5$ | Cl | NH | — | T$^{48}$ | |
| 207 | H | CH$_2$OCH$_3$ | OCH$_3$ | NH | — | T$^{49}$ | |
| 208 | H | CH$_2$OCH$_3$ | OCH$_3$ | NH | — | T$^{50}$ | solid |
| 209 | H | CH$_2$OCH$_3$ | OCH$_3$ | O | — | T$^{50}$ | |
| 210 | H | C$_2$H$_5$ | Cl | NH | — | T$^{50}$ | |
| 211 | H | C$_2$H$_5$ | Cl | O | — | T$^{50}$ | |
| 212 | H | —(CH$_2$)$_4$— | | O | — | T$^{50}$ | |
| 213 | H | CH$_2$OCH$_3$ | Cl | NH | — | T$^{51}$ | |
| 214 | H | CH$_2$OCH$_3$ | Cl | O | — | T$^{51}$ | |
| 215 | H | C$_2$H$_5$ | Cl | NH | — | T$^{51}$ | |
| 216 | H | C$_2$H$_5$ | Cl | O | — | T$^{51}$ | |
| 217 | H | —(CH$_2$)$_4$— | | O | — | T$^{51}$ | |
| 218 | | CH$_2$OCH$_3$ | OCH$_3$ | NH | — | T$^{52}$ | |
| 219 | | CH$_2$OCH$_3$ | OCH$_3$ | O | — | T$^{52}$ | |
| 220 | H | C$_2$H$_5$ | Cl | NH | — | T$^{52}$ | |
| 221 | H | C$_2$H$_5$ | Cl | O | — | T$^{52}$ | |
| 222 | H | —(CH$_2$)$_4$— | | O | — | T$^{52}$ | |
| 223 | H | CH$_2$OCH$_3$ | OCH$_3$ | NH | — | T$^{53}$ | 142–143 |
| 224 | H | CH$_2$OCH$_3$ | OCH$_3$ | O | — | T$^{53}$ | oil |
| 225 | H | —(CH$_2$)$_4$— | | O | — | T$^{53}$ | |
| 226 | H | CH$_2$OCH$_3$ | OCH$_3$ | NH | — | T$^{54}$ | 83–85 |
| 227 | H | CH$_2$OCH$_3$ | OCH$_3$ | O | — | T$^{54}$ | oil |
| 228 | H | —(CH$_2$)$_4$— | | O | — | T$^{54}$ | 95–100 |
| 229 | H | CH$_2$OCH$_3$ | OCH$_3$ | NH | — | T$^{55}$ | 112–114 |
| 230 | H | CH$_2$OCH$_3$ | OCH$_3$ | NH | — | T$^{56}$ | |
| 231 | H | CH$_2$OCH$_3$ | OCH$_3$ | NH | — | T$^{57}$ | |
| 232 | H | CH$_2$OCH$_3$ | OCH$_3$ | O | — | T$^{57}$ | |
| 233 | H | C$_2$H$_5$ | Cl | NH | — | T$^{57}$ | |
| 234 | H | C$_2$H$_5$ | Cl | O | — | T$^{57}$ | |
| 235 | H | —(CH$_2$)$_4$— | | O | — | T$^{57}$ | |
| 236 | H | CH$_2$OCH$_3$ | OCH$_3$ | NH | — | T$^{58}$ | 137–139 |
| 237 | H | CH$_2$OCH$_3$ | OCH$_3$ | O | — | T$^{58}$ | |
| 238 | H | C$_2$H$_5$ | Cl | NH | — | T$^{58}$ | |
| 239 | H | C$_2$H$_5$ | Cl | O | — | T$^{58}$ | |
| 240 | H | —(CH$_2$)$_4$— | | O | — | T$^{58}$ | |
| 241 | H | CH$_2$OCH$_3$ | OCH$_3$ | NH | — | T$^{59}$ | 84–85 |
| 242 | H | CH$_2$OCH$_3$ | OCH$_3$ | O | — | T$^{59}$ | |
| 243 | H | C$_2$H$_5$ | Cl | NH | — | T$^{59}$ | 83–84 |
| 244 | H | C$_2$H$_5$ | Cl | O | — | T$^{59}$ | |
| 245 | H | —(CH$_2$)$_4$— | | NH | — | T$^{59}$ | oil |
| 246 | H | CH$_2$OCH$_3$ | OCH$_3$ | NH | — | T$^{60}$ | |
| 247 | H | CH$_2$OCH$_3$ | OCH$_3$ | O | — | T$^{60}$ | |

TABLE I-continued

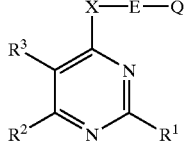

| Example No. | R¹ | R² | R³ | X | E | Q | M.p. [° C.] |
|---|---|---|---|---|---|---|---|
| 248 | H | C₂H₅ | Cl | NH | — | T⁶⁰ | |
| 249 | H | C₂H₅ | Cl | O | — | T⁶⁰ | |
| 250 | H | —(CH₂)₄— | | O | — | T⁶⁰ | |
| 251 | H | CH₂OCH₃ | OCH₃ | NH | — | T⁶¹ | |
| 252 | H | CH₂OCH₃ | OCH₃ | O | — | T⁶¹ | |
| 253 | H | C₂H₅ | Cl | NH | — | T⁶¹ | |
| 254 | H | C₂H₅ | Cl | O | — | T⁶¹ | |
| 255 | H | —(CH₂)₄— | | O | — | T⁶¹ | |
| 256 | H | CH₂OCH₃ | OCH₃ | NH | — | T⁶² | 95–96 |
| 257 | H | CH₂OCH₃ | OCH₃ | O | — | T⁶² | |
| 258 | H | C₂H₅ | Cl | NH | — | T⁶² | 101–102 |
| 259 | H | C₂H₅ | Cl | O | — | T⁶² | |
| 260 | H | —(CH₂)₄— | | O | — | T⁶² | |
| 261 | H | CH₂OCH₃ | OCH₃ | NH | — | T⁶³ | |
| 262 | H | CH₂OCH₃ | OCH₃ | O | — | T⁶³ | |
| 263 | H | C₂H₅ | Cl | NH | — | T⁶³ | 81–83 |
| 264 | H | C₂H₅ | Cl | O | — | T⁶³ | |
| 265 | H | —(CH₂)₄— | | O | — | T⁶³ | |
| 266 | H | CH₂OCH₃ | OCH₃ | NH | — | T⁶⁴ | |
| 267 | H | CH₂OCH₃ | OCH₃ | O | — | T⁶⁴ | |
| 268 | H | C₂H₅ | Cl | NH | — | T⁶⁴ | |
| 269 | H | C₂H₅ | Cl | O | — | T⁶⁴ | |
| 270 | H | —(CH₂)₄— | | — | — | T⁶⁴ | |
| 271 | H | CH₂OCH₃ | OCH₃ | NH | — | T⁶⁵ | |
| 272 | H | CH₂OCH₃ | OCH₃ | O | — | T⁶⁵ | |
| 273 | H | C₂H₅ | Cl | NH | — | T⁶⁵ | |
| 274 | H | C₂H₅ | Cl | O | — | T⁶⁵ | |
| 275 | H | —(CH₂)₄— | | O | — | T⁶⁵ | |
| 276 | H | CH₂OCH₃ | Cl | NH | — | T⁴ | |
| 277 | H | C₂C₅ | Br | NH | — | T⁴ | |
| 278 | H | C₂C₅ | C₂C₅ | NH | — | T⁴ | |
| 279 | H | CH₂OCH₃ | Cl | NH | — | T⁷ | oil |
| 280 | H | CH₂OCH₃ | C₂C₅ | NH | — | T⁷ | oil |
| 281 | H | CH₂OCH₃ | H | NH | — | T⁷ | oil |
| 282 | H | C₂H₅ | C₂H₅ | NH | — | T⁷ | |
| 283 | H | C₂H₅ | Br | NH | — | T⁷ | |
| 284 | H | C₂H₅ | F | NH | — | T⁷ | |
| 285 | H | CH₃ | Cl | NH | — | T⁷ | |
| 286 | H | CH₃ | OCH₃ | NH | — | T⁷ | |
| 287 | H | C₂H₅ | OCH₃ | NH | — | T⁷ | |
| 288 | H | CH(CH₃)₂ | Cl | NH | — | T⁷ | |
| 289 | H | cyclo-propyl | Cl | NH | — | T⁷ | |
| 290 | H | C₂H₅ | C₂H₅ | NH | — | T⁸ | |
| 291 | H | C₂H₅ | Br | NH | — | T⁸ | |
| 292 | H | CH₂OCH₃ | Cl | NH | — | T⁸ | |
| 293 | H | C₂H₅ | C₂H₅ | NH | — | T⁹ | |
| 294 | H | CH₂OCH₃ | Cl | NH | — | T⁹ | |
| 295 | H | C₂H₅ | Br | NH | — | T⁹ | |
| 296 | H | C₂H₅ | C₂H₅ | NH | — | T¹⁰ | |
| 297 | H | C₂H₅ | Br | NH | — | T¹⁰ | |
| 298 | H | CH₂OCH₃ | Cl | NH | — | T¹⁰ | |
| 299 | H | C₂H₅ | C₂H₅ | NH | — | T¹¹ | |
| 300 | H | C₂H₅ | C₂H₅ | O | — | T¹¹ | |
| 301 | H | CH₂OCH₃ | Cl | NH | — | T¹¹ | |
| 302 | H | C₂H₅ | Br | NH | — | T¹¹ | |
| 303 | H | C₂H₅ | C₂H₅ | NH | — | T¹⁴ | |
| 304 | H | C₂H₅ | C₂H₅ | O | — | T¹⁴ | |
| 305 | H | CH₂OCH₃ | Cl | NH | — | T¹⁴ | |
| 306 | H | CH₂OCH₃ | Cl | NH | — | T²³ | oil |
| 307 | H | CH₂OCH₃ | C₂H₅ | NH | — | T²³ | 78–79 |
| 308 | H | CH₂OCH₃ | H | NH | — | T²³ | oil |
| 309 | H | C₂H₅ | C₂H₅ | NH | — | T²³ | |
| 310 | H | C₂H₅ | I | NH | — | T²³ | |
| 311 | H | C₂H₅ | F | NH | — | T²³ | |
| 312 | H | C₂H₅ | F | O | — | T²³ | |
| 313 | H | C₂H₅ | Br | NH | — | T²³ | |

TABLE I-continued $$\text{structure with X-E-Q at position 4, R}^3\text{ at 5, R}^2\text{ at 6, R}^1\text{ at 2 of pyrimidine}$$

| Example No. | R¹ | R² | R³ | X | E | Q | M.p. [° C.] |
|---|---|---|---|---|---|---|---|
| 314 | H | $CH_3$ | Cl | NH | — | $T^{23}$ | |
| 315 | H | $(CH_2)_4$ | | NH | — | $T^{24}$ | 164–166 |
| 316 | H | $CH_2OCH_3$ | $OCH_3$ | NH | — | $T^{66}$ | |
| 317 | H | $CH_2OCH_3$ | $OCH_3$ | O | — | $T^{66}$ | oil |
| 318 | H | $C_2H_5$ | Cl | NH | — | $T^{66}$ | |
| 319 | H | $C_2H_5$ | Cl | O | — | $T^{66}$ | oil |
| 320 | H | $(CH_2)_4$ | | NH | — | $T^{66}$ | |
| 321 | H | $(CH_2)_4$ | | O | — | $T^{66}$ | oil |
| 322 | H | $C_2C_5$ | $C_2H_5$ | NH | — | $T^{66}$ | |
| 323 | H | $CH_2OCH_3$ | Cl | NH | — | $T^{66}$ | |
| 324 | H | $CH_2OCH_3$ | $OCH_3$ | NH | — | $T^{67}$ | |
| 325 | H | $CH_2OCH_3$ | $OCH_3$ | O | — | $T^{67}$ | |
| 326 | H | $C_2H_5$ | Cl | NH | — | $T^{67}$ | |
| 327 | H | $C_2H_5$ | Cl | O | — | $T^{67}$ | |
| 328 | H | $(CH_2)_4$ | | O | — | $T^{67}$ | |
| 329 | H | $CH_2OCH_3$ | $OCH_3$ | NH | — | $T^{68}$ | oil |
| 330 | H | $CH_2OCH_3$ | $OCH_3$ | O | — | $T^{68}$ | oil |
| 331 | H | $C_2H_5$ | Cl | NH | — | $T^{68}$ | oil |
| 332 | H | $C_2H_5$ | Cl | O | — | $T^{68}$ | oil |
| 333 | H | $C_2H_5$ | $C_2H_5$ | NH | — | $T^{68}$ | |
| 334 | H | $C_2H_5$ | $C_2H_5$ | O | — | $T^{68}$ | |
| 335 | H | $(CH_2)_4$ | | NH | — | $T^{68}$ | |
| 336 | H | $(CH_2)_4$ | | O | — | $T^{68}$ | oil |
| 337 | H | $C_2C_5$ | Br | NH | — | $T^{68}$ | |
| 338 | H | $C_2H_5$ | Br | O | — | $T^{68}$ | |
| 339 | H | $C_2H_5$ | F | NH | — | $T^{68}$ | |
| 340 | H | $C_2H_5$ | F | O | — | $T^{68}$ | |
| 341 | H | $CH_2OCH_3$ | Cl | NH | — | $T^{68}$ | |
| 342 | H | $CH_2OCH_3$ | Cl | O | — | $T^{68}$ | |
| 343 | H | $CH_3$ | Cl | NH | — | $T^{68}$ | |
| 344 | H | $CH_2OCH_3$ | $OCH_3$ | NH | — | $T^{69}$ | |
| 345 | H | $CH_2OCH_3$ | $OCH_3$ | O | — | $T^{69}$ | |
| 346 | H | $C_2H_5$ | Cl | NH | — | $T^{69}$ | |
| 347 | H | $C_2H_5$ | Cl | NH | — | $T^{69}$ | |
| 348 | H | $(CH_2)_4$ | | NH | — | $T^{69}$ | |
| 349 | H | $(CH_2)_4$ | | O | — | $T^{69}$ | 79–82 |
| 350 | H | $C_2H_5$ | $C_2H_5$ | NH | — | $T^{69}$ | |
| 351 | H | $C_2H_5$ | $C_2H_5$ | O | — | $T^{69}$ | |
| 352 | H | $C_2H_5$ | Cl | NH | — | $T^{70}$ | |
| 352 | H | $C_2H_5$ | Cl | O | — | $T^{70}$ | oil |
| 354 | H | $CH_2OCH_3$ | $OCH_3$ | NH | — | $T^{70}$ | |
| 355 | H | $CH_2OCH_3$ | $OCH_3$ | O | — | $T^{70}$ | oil |
| 356 | H | $(CH_2)_4$ | | O | — | $T^{70}$ | oil |
| 357 | H | $CH_2OCH_3$ | $OCH_3$ | NH | — | $T^{71}$ | oil |
| 358 | H | $CH_2OCH_3$ | $OCH_3$ | O | — | $T^{71}$ | |
| 359 | H | $C_2H_5$ | Cl | NH | — | $T^{71}$ | oil |
| 360 | H | $C_2H_5$ | Cl | O | — | $T^{71}$ | |
| 361 | H | $(CH_2)_4$ | | NH | — | $T^{71}$ | |
| 362 | H | $(CH_2)_4$ | | O | — | $T^{71}$ | |
| 363 | H | $C_2H_5$ | $C_2H_5$ | NH | — | $T^{71}$ | |
| 364 | H | $C_2H_5$ | $C_2H_5$ | O | — | $T^{71}$ | |
| 365 | H | $CH_2OCH_3$ | $OCH_3$ | NH | — | $T^{72}$ | oil |
| 366 | H | $CH_2OCH_3$ | $OCH_3$ | O | — | $T^{72}$ | |
| 367 | H | $C_2H_5$ | Cl | NH | — | $T^{72}$ | |
| 368 | H | $C_2H_5$ | Cl | O | — | $T^{72}$ | |
| 369 | H | $(CH_2)_4$ | | NH | — | $T^{72}$ | |
| 370 | H | $(CH_2)_4$ | | O | — | $T^{72}$ | |
| 371 | H | $C_2H_5$ | $C_2H_5$ | NH | — | $T^{72}$ | |
| 372 | H | $C_2H_5$ | $C_2H_5$ | O | — | $T^{72}$ | |
| 373 | H | $CH_2OCH_3$ | $OCH_3$ | NH | — | $T^{73}$ | |
| 374 | H | $CH_2OCH_3$ | $OCH_3$ | O | — | $T^{73}$ | |
| 375 | H | $C_2H_5$ | Cl | NH | — | $T^{73}$ | |
| 376 | H | $C_2H_5$ | Cl | O | — | $T^{73}$ | |
| 377 | H | $(CH_2)_4$ | | O | | — | $T^{73}$ |
| 378 | H | $CH_2OCH_3$ | $OCH_3$ | NH | — | $T^{74}$ | |
| 379 | H | $CH_2OCH_3$ | $OCH_3$ | O | — | $T^{74}$ | oil |
| 380 | H | $C_2H_5$ | Cl | NH | — | $T^{74}$ | |

TABLE I-continued

| Example No. | R¹ | R² | R³ | X | E | Q | M.p. [° C.] |
|---|---|---|---|---|---|---|---|
| 381 | H | $C_2H_5$ | Cl | O | — | $T^{74}$ | 87 |
| 382 | H | $(CH_2)_4$ | | O | — | $T^{74}$ | 86 |
| 383 | H | $C_2H_5$ | Cl | NH | — | $T^{75}$ | |
| 384 | H | $CH_2OCH_3$ | $OCH_3$ | NH | — | $T^{76}$ | oil |
| 385 | H | $CH_2OCH_3$ | $OCH_3$ | O | — | $T^{76}$ | oil |
| 386 | H | $C_2H_5$ | Cl | NH | — | $T^{76}$ | oil |
| 387 | H | $C_2H_5$ | Cl | O | — | $T^{76}$ | 58 |
| 388 | H | $(CH_2)_4$ | | NH | — | $T^{76}$ | |
| 389 | H | $(CH_2)_4$ | | O | — | $T^{76}$ | 99–100 |
| 390 | H | $CH_2OCH_3$ | $C_2H_5$ | NH | — | $T^{76}$ | oil |
| 391 | H | $C_2H_5$ | $C_2H_5$ | NH | — | $T^{76}$ | |
| 392 | H | $C_2H_5$ | $C_2H_5$ | O | — | $T^{76}$ | |
| 393 | H | $CH_2OCH_3$ | Cl | NH | — | $T^{76}$ | |
| 394 | H | $C_2H_5$ | F | NH | — | $T^{76}$ | |
| 395 | H | $C_2H_5$ | Br | NH | — | $T^{76}$ | |
| 396 | H | $CH_3$ | Cl | NH | — | $T^{76}$ | |
| 397 | H | $C_2H_5$ | Cl | NH | — | $T^{76}$ | 73–75 |
| 398 | H | $(CH_2)_4$ | | O | — | $T^{77}$ | 83 |
| 399 | H | $CH_2OCH_3$ | $C_2H_5$ | NH | — | $T^{77}$ | 90–92 |
| 400 | H | $CH_2OCH_3$ | $OCH_3$ | NH | — | $T^{78}$ | |
| 401 | H | $CH_2OCH_3$ | $OCH_3$ | O | — | $T^{78}$ | |
| 402 | H | $C_2H_5$ | Cl | NH | — | $T^{78}$ | oil |
| 403 | H | $C_2H_5$ | Cl | O | — | $T^{78}$ | oil |
| 404 | H | $(CH_2)_4$ | | O | — | $T^{78}$ | oil |
| 405 | H | $CH_2OCH_3$ | $OCH_3$ | NH | — | $T^{79}$ | |
| 406 | H | $C_2H_5$ | Cl | NH | — | $T^{79}$ | 78–79 |
| 407 | H | $CH_2OCH_3$ | $OCH_3$ | NH | — | $T^{80}$ | |
| 408 | H | $CH_2OCH_3$ | $OCH_3$ | O | — | $T^{80}$ | oil |
| 409 | H | $C_2H_5$ | Cl | NH | — | $T^{80}$ | oil |
| 410 | H | $C_2H_5$ | Cl | O | — | $T^{80}$ | oil |
| 411 | H | $(CH_2)_4$ | | O | — | $T^{80}$ | oil |
| 412 | H | $C_2H_5$ | Cl | NH | — | $T^{81}$ | 72–74 |
| 413 | H | $C_2H_5$ | Cl | O | — | $T^{81}$ | oil |
| 414 | H | $CH_2OCH_3$ | $OCH_3$ | NH | — | $T^{82}$ | |
| 415 | H | $CH_2OCH_3$ | $OCH_3$ | O | — | $T^{82}$ | oil |
| 416 | H | $C_2H_5$ | Cl | NH | — | $T^{82}$ | |
| 417 | H | $C_2H_5$ | Cl | O | — | $T^{82}$ | 65 |
| 418 | H | $(CH_2)_4$ | | O | — | $T^{82}$ | 68 |
| 419 | H | $CH_2OCH_3$ | $OCH_3$ | NH | — | $T^{84}$ | |
| 420 | H | $CH_2OCH_3$ | $OCH_3$ | O | — | $T^{84}$ | |
| 421 | H | $C_2H_5$ | Cl | NH | — | $T^{84}$ | |
| 422 | H | $C_2H_5$ | Cl | O | — | $T^{84}$ | |
| 423 | H | $(CH_2)_4$ | | O | — | $T^{84}$ | |
| 424 | H | $CH_2OCH_3$ | $OCH_3$ | NH | | $T^{85}$ | |
| 425 | H | $CH_2OCH_3$ | $OCH_3$ | O | | $T^{85}$ | |
| 426 | H | $C_2H_5$ | Cl | NH | | $T^{85}$ | |
| 427 | H | $C_2H_5$ | Cl | O | | $T^{85}$ | |
| 428 | H | $(CH_2)_4$ | | O | | $T^{85}$ | |
| 429 | H | $CH_2OCH_3$ | $OCH_3$ | NH | — | $T^{86}$ | |
| 430 | H | $CH_2OCH_3$ | $OCH_3$ | O | — | $T^{86}$ | |
| 431 | H | $C_2H_5$ | Cl | NH | — | $T^{86}$ | |
| 432 | H | $C_2H_5$ | Cl | O | — | $T^{86}$ | |
| 433 | H | $(CH_2)_4$ | | O | — | $T^{86}$ | |
| 434 | H | $CH_2OCH_3$ | $OCH_3$ | NH | — | $T^{87}$ | |
| 435 | H | $CH_2OCH_3$ | $OCH_3$ | O | — | $T^{87}$ | oil |
| 436 | H | $C_2H_5$ | Cl | NH | — | $T^{87}$ | oil |
| 437 | H | $C_2H_5$ | Cl | O | — | $T^{87}$ | 57 |
| 438 | H | $(CH_2)_4$ | | O | — | $T^{87}$ | 67 |
| 439 | H | $C_2H_5$ | Cl | NH | — | $T^{88}$ | 65–66 |
| 440 | H | $CH_2OCH_3$ | $OCH_3$ | NH | — | $T^{89}$ | oil |
| 441 | H | $CH_2OCH_3$ | $OCH_3$ | O | — | $T^{89}$ | oil |
| 442 | H | $C_2H_5$ | Cl | NH | — | $T^{89}$ | oil |
| 443 | H | $C_2H_5$ | Cl | O | — | $T^{89}$ | 53 |
| 444 | H | $(CH_2)_4$ | | O | — | $T^{89}$ | 59 |
| 445 | H | $CH_2OCH_3$ | $OCH_3$ | NH | — | $T^{90}$ | oil |
| 446 | H | $C_2H_5$ | $OCH_3$ | NH | — | $T^{90}$ | 63–65 |
| 447 | H | $CH_2OCH_3$ | $OCH_3$ | NH | — | $T^{91}$ | |

TABLE I-continued $$\underset{R^2}{\overset{R^3}{\bigcirc}}\underset{N}{\overset{X-E-Q}{\underset{R^1}{\bigcirc}}}$$

| Example No. | R¹ | R² | R³ | X | E | Q | M.p. [° C.] |
|---|---|---|---|---|---|---|---|
| 448 | H | CH₂OCH₃ | OCH₃ | O | — | T⁹¹ | |
| 449 | H | C₂H₅ | Cl | NH | — | T⁹¹ | |
| 450 | H | C₂H₅ | Cl | O | — | T⁹¹ | |
| 451 | H | (CH₂)₄ | | O | — | T⁹¹ | |
| 452 | H | CH₂OCH₃ | OCH₃ | NH | — | T⁹² | |
| 453 | H | CH₂OCH₃ | OCH₃ | O | — | T⁹² | |
| 454 | H | C₂H₅ | Cl | NH | — | T⁹² | |
| 455 | H | C₂H₅ | Cl | O | — | T⁹² | |
| 456 | H | (CH₂)₄ | | NH | — | T⁹² | |
| 457 | H | CH₂OCH₃ | OCH₃ | O | — | T⁹³ | |
| 458 | H | CH₂OCH₃ | OCH₃ | NH | — | T⁹³ | |
| 459 | H | C₂H₅ | Cl | O | — | T⁹³ | |
| 460 | H | C₂H₅ | Cl | O | — | T⁹³ | |
| 461 | H | (CH₂)₄ | | NH | — | T⁹³ | |
| 462 | H | (CH₂)₄ | | O | — | T⁹³ | |
| 463 | H | CH₂OCH₃ | OCH₃ | NH | — | T⁹⁴ | |
| 464 | H | CH₂OCH₃ | OCH₃ | O | — | T⁹⁴ | |
| 465 | H | C₂H₅ | Cl | NH | — | T⁹⁴ | oil |
| 466 | H | C₂H₅ | Cl | O | — | T⁹⁴ | 58–60 |
| 467 | H | (CH₂)₄ | | O | — | T⁹⁴ | oil |
| 468 | H | CH₂OCH₃ | OCH₃ | NH | — | T⁹⁵ | |
| 469 | H | CH₂OCH₃ | OCH₃ | O | — | T⁹⁵ | |
| 470 | H | C₂H₅ | Cl | NH | — | T⁹⁵ | oil |
| 471 | H | C₂H₅ | Cl | O | — | T⁹⁵ | oil |
| 472 | H | (CH₂)₄ | | O | — | T⁹⁵ | oil |
| 473 | H | C₂H₅ | Cl | NH | — | T⁹⁶ | oil |
| 474 | H | CH₂OCH₃ | OCH₃ | NH | — | T⁹⁷ | |
| 475 | H | CH₂OCH₃ | OCH₃ | O | — | T⁹⁷ | |
| 476 | H | C₂H₅ | Cl | NH | — | T⁹⁷ | |
| 477 | H | C₂H₅ | Cl | O | — | T⁹⁷ | 71 |
| 478 | H | (CH₂)₄ | | NH | — | T⁹⁷ | |
| 479 | H | (CH₂)₄ | | O | — | T⁹⁷ | oil |
| 480 | H | CH₂OCH₃ | OCH₃ | NH | — | T⁹⁸ | |
| 481 | H | CH₂OCH₃ | OCH₃ | O | — | T⁹⁸ | |
| 482 | H | C₂H₅ | Cl | NH | — | T⁹⁸ | |
| 483 | H | C₂H₅ | Cl | O | — | T⁹⁸ | |
| 484 | H | (CH₂)₄ | | O | — | T⁹⁸ | oil |
| 485 | H | CH₂OCH₃ | OCH₃ | NH | — | T⁹⁹ | |
| 486 | H | CH₂OCH₃ | OCH₃ | O | — | T⁹⁹ | |
| 487 | H | C₂H₅ | Cl | NH | — | T⁹⁹ | |
| 488 | H | C₂H₅ | Cl | O | — | T⁹⁹ | |
| 489 | H | (CH₂)₄ | | O | — | T⁹⁹ | |
| 490 | H | CH₂OCH₃ | OCH₃ | NH | — | T¹⁰⁰ | |
| 491 | H | CH₂OCH₃ | OCH₃ | O | — | T¹⁰⁰ | |
| 492 | H | C₂H₅ | Cl | NH | — | T¹⁰⁰ | |
| 493 | H | C₂H₅ | Cl | O | — | T¹⁰⁰ | |
| 494 | H | (CH₂)₄ | | O | — | T¹⁰⁰ | |
| 495 | H | CH₂OCH₃ | OCH₃ | NH | — | T¹⁰¹ | |
| 496 | H | CH₂OCH₃ | OCH₃ | O | — | T¹⁰¹ | |
| 497 | H | C₂H₅ | Cl | NH | — | T¹⁰¹ | |
| 498 | H | C₂H₅ | Cl | O | — | T¹⁰¹ | |
| 499 | H | (CH₂)₄ | | O | — | T¹⁰¹ | |
| 500 | H | CH₂OCH₃ | OCH₃ | NH | — | T¹⁰² | |
| 501 | H | CH₂OCH₃ | OCH₃ | O | — | T¹⁰² | |
| 502 | H | C₂H₅ | Cl | NH | — | T¹⁰² | |
| 503 | H | C₂H₅ | Cl | O | — | T¹⁰² | |
| 504 | H | (CH₂)₄ | | O | — | T¹⁰² | |
| 505 | H | CH₂OCH₃ | OCH₃ | NH | — | T¹⁰³ | |
| 506 | H | CH₂OCH₃ | OCH₃ | O | — | T¹⁰³ | |
| 507 | H | C₂H₅ | Cl | NH | — | T¹⁰³ | |
| 508 | H | C₂H₅ | Cl | O | — | T¹⁰³ | |
| 509 | H | (CH₂)₄ | | O | — | T¹⁰³ | |
| 510 | H | CH₂OCH₃ | OCH₃ | NH | — | T¹⁰⁴ | |
| 511 | H | CH₂OCH₃ | OCH₃ | O | — | T¹⁰⁴ | oil |
| 512 | H | C₂H₅ | Cl | NH | — | T¹⁰⁴ | |
| 513 | H | C₂H₅ | Cl | O | — | T¹⁰⁴ | 100–103 |
| 514 | H | (CH₂)₄ | | O | — | T¹⁰⁴ | 108–112 |

TABLE I-continued

| Example No. | R$^1$ | R$^2$ | R$^3$ | X | E | Q | M.p. [° C.] |
|---|---|---|---|---|---|---|---|
| 515 | H | CH$_2$OCH$_3$ | OCH$_3$ | NH | — | T$^{105}$ | |
| 516 | H | CH$_2$OCH$_3$ | OCH$_3$ | O | — | T$^{105}$ | |
| 517 | H | C$_2$H$_5$ | Cl | NH | — | T$^{105}$ | |
| 518 | H | C$_2$H$_5$ | Cl | O | — | T$^{105}$ | |
| 519 | H | (CH$_2$)$_4$ | | O | — | T$^{105}$ | |
| 520 | H | CH$_2$OCH$_3$ | OCH$_3$ | NH | — | T$^{106}$ | |
| 521 | H | CH$_2$OCH$_3$ | OCH$_3$ | O | — | T$^{106}$ | |
| 522 | H | C$_2$H$_5$ | Cl | NH | — | T$^{106}$ | |
| 523 | H | C$_2$H$_5$ | Cl | O | — | T$^{106}$ | |
| 524 | H | (CH$_2$)$_4$ | | O | — | T$^{106}$ | |
| 525 | H | CH$_2$OCH$_3$ | OCH$_3$ | NH | — | T$^{107}$ | |
| 526 | H | CH$_2$OCH$_3$ | OCH$_3$ | O | — | T$^{107}$ | oil |
| 527 | H | C$_2$H$_5$ | Cl | NH | — | T$^{107}$ | |
| 528 | H | C$_2$H$_5$ | Cl | O | — | T$^{107}$ | oil |
| 529 | H | (CH$_2$)$_4$ | | O | — | T$^{107}$ | oil |
| 530 | H | CH$_2$OCH$_3$ | OCH$_3$ | NH | — | T$^{108}$ | |
| 531 | H | CH$_2$OCH$_3$ | OCH$_3$ | O | — | T$^{108}$ | |
| 532 | H | C$_2$H$_5$ | Cl | NH | — | T$^{108}$ | |
| 533 | H | C$_2$H$_5$ | Cl | O | — | T$^{108}$ | |
| 534 | H | (CH$_2$)$_4$ | | O | — | T$^{108}$ | |
| 535 | H | CH$_2$OCH$_3$ | OCH$_3$ | NH | — | T$^{109}$ | |
| 536 | H | CH$_2$OCH$_3$ | OCH$_3$ | O | — | T$^{109}$ | |
| 537 | H | C$_2$H$_5$ | Cl | NH | — | T$^{109}$ | |
| 538 | H | C$_2$H$_5$ | Cl | O | — | T$^{109}$ | |
| 539 | H | (CH$_2$)$_4$ | | O | — | T$^{109}$ | |
| 540 | H | CH$_2$OCH$_3$ | OCH$_3$ | NH | — | T$^{110}$ | |
| 541 | H | CH$_2$OCH$_3$ | OCH$_3$ | O | — | T$^{110}$ | |
| 542 | H | C$_2$H$_5$ | Cl | NH | — | T$^{110}$ | |
| 543 | H | C$_2$H$_5$ | Cl | O | — | T$^{110}$ | |
| 544 | H | (CH$_2$)$_4$ | | O | — | T$^{110}$ | |
| 545 | H | CH$_2$OCH$_3$ | OCH$_3$ | NH | — | T$^{111}$ | |
| 546 | H | CH$_2$OCH$_3$ | OCH$_3$ | O | — | T$^{111}$ | |
| 547 | H | C$_2$H$_5$ | Cl | NH | — | T$^{111}$ | |
| 548 | H | C$_2$H$_5$ | Cl | O | — | T$^{111}$ | |
| 549 | H | (CH$_2$)$_4$ | | O | — | T$^{111}$ | |
| 550 | H | CH$_2$OCH$_3$ | OCH$_3$ | NH | — | T$^{112}$ | |
| 551 | H | CH$_2$OCH$_3$ | OCH$_3$ | O | — | T$^{112}$ | |
| 552 | H | C$_2$H$_5$ | Cl | NH | — | T$^{112}$ | |
| 553 | H | C$_2$H$_5$ | Cl | O | — | T$^{112}$ | |
| 554 | H | (CH$_2$)$_4$ | | O | — | T$^{112}$ | oil |
| 555 | H | CH$_2$OCH$_3$ | OCH$_3$ | NH | — | T$^{113}$ | |
| 556 | H | CH$_2$OCH$_3$ | OCH$_3$ | O | — | T$^{113}$ | |
| 557 | H | C$_2$H$_5$ | Cl | NH | — | T$^{113}$ | |
| 558 | H | C$_2$H$_5$ | Cl | O | — | T$^{113}$ | |
| 559 | H | (CH$_2$)$_4$ | | O | — | T$^{113}$ | |
| 560 | H | CH$_2$OCH$_3$ | OCH$_3$ | NH | — | T$^{114}$ | |
| 561 | H | CH$_2$OCH$_3$ | OCH$_3$ | O | — | T$^{114}$ | |
| 562 | H | C$_2$H$_5$ | Cl | NH | — | T$^{114}$ | |
| 563 | H | C$_2$H$_5$ | Cl | O | — | T$^{114}$ | oil |
| 564 | H | (CH$_2$)$_4$ | | O | — | T$^{114}$ | |
| 565 | H | CH$_2$OCH$_3$ | OCH$_3$ | NH | — | T$^{115}$ | |
| 566 | H | CH$_2$OCH$_3$ | OCH$_3$ | O | — | T$^{115}$ | oil |
| 567 | H | C$_2$H$_5$ | Cl | NH | — | T$^{115}$ | oil |
| 568 | H | C$_2$H$_5$ | Cl | O | — | T$^{115}$ | |
| 569 | H | (CH$_2$)$_4$ | | O | — | T$^{115}$ | oil |
| 570 | H | C$_2$H$_5$ | Cl | NH | — | T$^{116}$ | oil |
| 571 | H | CH$_2$OCH$_3$ | OCH$_3$ | NH | — | T$^{117}$ | |
| 572 | H | CH$_2$OCH$_3$ | OCH$_3$ | O | — | T$^{117}$ | |
| 573 | H | C$_2$H$_5$ | Cl | NH | — | T$^{117}$ | |
| 574 | H | C$_2$H$_5$ | Cl | O | — | T$^{117}$ | |
| 575 | H | (CH$_2$)$_4$ | | O | — | T$^{117}$ | |
| 576 | H | CH$_2$OCH$_3$ | OCH$_3$ | NH | — | T$^{118}$ | |
| 577 | H | CH$_2$OCH$_3$ | OCH$_3$ | O | — | T$^{118}$ | oil |
| 578 | H | C$_2$H$_5$ | Cl | NH | — | T$^{118}$ | |
| 579 | H | C$_2$H$_5$ | Cl | O | — | T$^{118}$ | oil |
| 580 | H | (CH$_2$)$_4$ | | O | — | T$^{118}$ | oil |
| 581 | H | CH$_2$OCH$_3$ | OCH$_3$ | NH | — | T$^{119}$ | |

TABLE I-continued

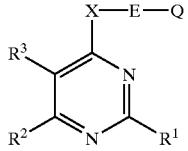

| Example No. | $R^1$ | $R^2$ | $R^3$ | X | E | Q | M.p. [° C.] |
|---|---|---|---|---|---|---|---|
| 582 | H | $CH_2OCH_3$ | $OCH_3$ | O | — | $T^{119}$ | |
| 583 | H | $C_2H_5$ | Cl | NH | — | $T^{119}$ | |
| 584 | H | $C_2H_5$ | Cl | O | — | $T^{119}$ | |
| 585 | H | $(CH_2)_4$ | | O | — | $T^{119}$ | |
| 586 | H | $CH_2OCH_3$ | $OCH_3$ | NH | — | $T^{120}$ | |
| 587 | H | $CH_2OCH_3$ | $OCH_3$ | O | — | $T^{120}$ | |
| 588 | H | $C_2H_5$ | Cl | NH | — | $T^{120}$ | |
| 589 | H | $C_2H_5$ | Cl | O | — | $T^{120}$ | |
| 590 | H | $(CH_2)_4$ | | O | — | $T^{120}$ | |
| 591 | H | $CH_2OCH_3$ | $OCH_3$ | NH | — | $T^{121}$ | |
| 592 | H | $CH_2OCH_3$ | $OCH_3$ | O | — | $T^{121}$ | |
| 593 | H | $C_2H_5$ | Cl | NH | — | $T^{121}$ | |
| 594 | H | $C_2H_5$ | Cl | O | — | $T^{121}$ | |
| 595 | H | $(CH_2)_4$ | | O | — | $T^{121}$ | |
| 596 | H | $CH_2OCH_3$ | $OCH_3$ | NH | — | $T^{122}$ | |
| 597 | H | $CH_2OCH_3$ | $OCH_3$ | O | — | $T^{122}$ | |
| 598 | H | $C_2H_5$ | Cl | NH | — | $T^{122}$ | |
| 599 | H | $C_2H_5$ | Cl | O | — | $T^{122}$ | |
| 600 | H | $(CH_2)_4$ | | O | — | $T^{122}$ | |
| 601 | H | $CH_2OCH_3$ | $OCH_3$ | NH | — | $T^{123}$ | |
| 602 | H | $CH_2OCH_3$ | $OCH_3$ | O | — | $T^{123}$ | oil |
| 603 | H | $C_2H_5$ | Cl | NH | — | $T^{123}$ | |
| 604 | H | $C_2H_5$ | Cl | O | — | $T^{123}$ | |
| 605 | H | $(CH_2)_4$ | | O | — | $T^{123}$ | 63–73 |
| 606 | H | $CH_2OCH_3$ | $OCH_3$ | NH | — | $T^{124}$ | |
| 607 | H | $CH_2OCH_3$ | $OCH_3$ | O | — | $T^{124}$ | |
| 608 | H | $C_2H_5$ | Cl | NH | — | $T^{124}$ | |
| 609 | H | $C_2H_5$ | Cl | O | — | $T^{124}$ | |
| 610 | H | $(CH_2)_4$ | | O | — | $T^{124}$ | |
| 611 | H | $CH_2OCH_3$ | $OCH_3$ | NH | — | $T^{125}$ | |
| 612 | H | $CH_2OCH_3$ | $OCH_3$ | O | — | $T^{125}$ | |
| 613 | H | $C_2H_5$ | Cl | NH | — | $T^{125}$ | |
| 614 | H | $C_2H_5$ | Cl | O | — | $T^{125}$ | |
| 615 | H | $(CH_2)_4$ | | O | — | $T^{125}$ | |
| 616 | H | $CH_2OCH_3$ | $OCH_3$ | NH | — | $T^{126}$ | |
| 617 | H | $CH_2OCH_3$ | $OCH_3$ | O | — | $T^{126}$ | |
| 618 | H | $C_2H_5$ | Cl | NH | — | $T^{126}$ | |
| 619 | H | $C_2H_5$ | Cl | O | — | $T^{126}$ | |
| 620 | H | $(CH_2)_4$ | | O | — | $T^{126}$ | |
| 621 | H | $CH_2OCH_3$ | $OCH_3$ | NH | — | $T^{127}$ | |
| 622 | H | $CH_2OCH_3$ | $OCH_3$ | O | — | $T^{127}$ | |
| 623 | H | $C_2H_5$ | Cl | NH | — | $T^{127}$ | |
| 624 | H | $C_2H_5$ | Cl | O | — | $T^{127}$ | |
| 625 | H | $(CH_2)_4$ | | O | — | $T^{127}$ | |
| 626 | H | $CH_2OCH_3$ | $OCH_3$ | NH | — | $T^{128}$ | |
| 627 | H | $CH_2OCH_3$ | $OCH_3$ | O | — | $T^{128}$ | |
| 628 | H | $C_2H_5$ | Cl | NH | — | $T^{128}$ | |
| 629 | H | $C_2H_5$ | Cl | O | — | $T^{128}$ | |
| 630 | H | $(CH_2)_4$ | | O | — | $T^{128}$ | |
| 631 | H | $CH_2OCH_3$ | $OCH_3$ | NH | — | $T^{129}$ | |
| 632 | H | $CH_2OCH_3$ | $OCH_3$ | O | — | $T^{129}$ | |
| 633 | H | $C_2H_5$ | Cl | NH | — | $T^{129}$ | |
| 634 | H | $C_2H_5$ | Cl | O | — | $T^{129}$ | |
| 635 | H | $(CH_2)_4$ | | O | — | $T^{129}$ | |
| 636 | H | $CH_2OCH_3$ | $OCH_3$ | NH | — | $T^{130}$ | |
| 637 | H | $CH_2OCH_3$ | $OCH_3$ | O | — | $T^{130}$ | |
| 638 | H | $C_2H_5$ | Cl | NH | — | $T^{130}$ | |
| 639 | H | $C_2H_5$ | Cl | O | — | $T^{130}$ | |
| 640 | H | $(CH_2)_4$ | | O | — | $T^{130}$ | |
| 641 | H | $CH_2OCH_3$ | $OCH_3$ | NH | — | $T^{131}$ | |
| 642 | H | $CH_2OCH_3$ | $OCH_3$ | O | — | $T^{131}$ | |
| 643 | H | $C_2H_5$ | Cl | NH | — | $T^{131}$ | |
| 644 | H | $C_2H_5$ | Cl | O | — | $T^{131}$ | |
| 645 | H | $(CH_2)_4$ | | O | — | $T^{131}$ | |
| 646 | H | $CH_2OCH_3$ | $OCH_3$ | NH | — | $T^{132}$ | |
| 647 | H | $CH_2OCH_3$ | $OCH_3$ | O | — | $T^{132}$ | |
| 648 | H | $C_2H_5$ | Cl | NH | — | $T^{132}$ | |

TABLE I-continued

| Example No. | R¹ | R² | R³ | X | E | Q | M.p. [° C.] |
|---|---|---|---|---|---|---|---|
| 649 | H | C₂H₅ | Cl | O | — | T¹³² | |
| 650 | H | (CH₂)₄ | | O | — | T¹³² | |
| 651 | H | CH₂OCH₃ | OCH₃ | NH | — | T¹³³ | |
| 652 | H | CH₂OCH₃ | OCH₃ | O | — | T¹³³ | |
| 653 | H | C₂H₅ | Cl | NH | — | T¹³³ | |
| 654 | H | C₂H₅ | Cl | O | — | T¹³³ | |
| 655 | H | (CH₂)₄ | | O | — | T¹³³ | |
| 656 | H | CH₂OCH₃ | OCH₃ | NH | — | T¹³⁴ | |
| 657 | H | CH₂OCH₃ | OCH₃ | O | — | T¹³⁴ | |
| 658 | H | C₂H₅ | Cl | NH | — | T¹³⁴ | |
| 659 | H | C₂H₅ | Cl | O | — | T¹³⁴ | |
| 660 | H | (CH₂)₄ | | O | — | T¹³⁴ | |
| 661 | H | CH₂OCH₃ | OCH₃ | NH | — | T¹³⁵ | |
| 662 | H | CH₂OCH₃ | OCH₃ | O | — | T¹³⁵ | |
| 663 | H | C₂H₅ | Cl | NH | — | T¹³⁵ | |
| 664 | H | C₂H₅ | Cl | O | — | T¹³⁵ | |
| 665 | H | (CH₂)₄ | | O | — | T¹³⁵ | |
| 666 | H | CH₂OCH₃ | OCH₃ | NH | — | T¹³⁶ | |
| 667 | H | CH₂OCH₃ | OCH₃ | O | — | T¹³⁶ | |
| 668 | H | C₂H₅ | Cl | NH | — | T¹³⁶ | |
| 669 | H | C₂H₅ | Cl | O | — | T¹³⁶ | |
| 670 | H | (CH₂)₄ | | O | — | T¹³⁶ | |
| 671 | H | CH₂OCH₃ | OCH₃ | NH | — | T¹³⁷ | |
| 672 | H | CH₂OCH₃ | OCH₃ | O | — | T¹³⁷ | |
| 673 | H | C₂H₅ | Cl | NH | — | T¹³⁷ | |
| 674 | H | C₂H₅ | Cl | O | — | T¹³⁷ | |
| 675 | H | (CH₂)₄ | | O | — | T¹³⁷ | |
| 676 | H | CH₂OCH₃ | OCH₃ | NH | — | T¹³⁸ | |
| 677 | H | CH₂OCH₃ | OCH₃ | O | — | T¹³⁸ | |
| 678 | H | C₂H₅ | Cl | NH | — | T¹³⁸ | |
| 679 | H | C₂H₅ | Cl | O | — | T¹³⁸ | |
| 680 | H | (CH₂)₄ | | O | — | T¹³⁸ | |
| 681 | H | CH₂OCH₃ | OCH₃ | NH | — | T¹³⁹ | |
| 682 | H | CH₂OCH₃ | OCH₃ | O | — | T¹³⁹ | |
| 683 | H | C₂H₅ | Cl | NH | — | T¹³⁹ | |
| 684 | H | C₂H₅ | Cl | O | — | T¹³⁹ | |
| 685 | H | (CH₂)₄ | | O | — | T¹³⁹ | |
| 686 | H | CH₂OCH₃ | OCH₃ | NH | — | T¹⁴⁰ | |
| 687 | H | CH₂OCH₃ | OCH₃ | O | — | T¹⁴⁰ | |
| 688 | H | C₂H₅ | Cl | NH | — | T¹⁴⁰ | |
| 689 | H | C₂H₅ | Cl | O | — | T¹⁴⁰ | |
| 690 | H | (CH₂)₄ | | O | — | T¹⁴⁰ | |
| 691 | H | CH₂OCH₃ | OCH₃ | NH | — | T¹⁴¹ | |
| 692 | H | CH₂OCH₃ | OCH₃ | O | — | T¹⁴¹ | |
| 693 | H | C₂H₅ | Cl | NH | — | T¹⁴¹ | 65–66 |
| 694 | H | C₂H₅ | Cl | O | — | T¹⁴¹ | |
| 695 | H | (CH₂)₄ | | O | — | T¹⁴¹ | |
| 696 | H | CH₂OCH₃ | OCH₃ | NH | — | T¹⁴² | |
| 697 | H | CH₂OCH₃ | OCH₃ | O | — | T¹⁴² | |
| 698 | H | C₂H₅ | Cl | NH | — | T¹⁴² | |
| 699 | H | C₂H₅ | Cl | O | — | T¹⁴² | |
| 700 | H | (CH₂)₄ | | O | — | T¹⁴² | |
| 701 | H | CH₂OCH₃ | OCH₃ | NH | — | T¹⁴³ | |
| 702 | H | CH₂OCH₃ | OCH₃ | O | — | T¹⁴³ | |
| 703 | H | C₂H₅ | Cl | NH | — | T¹⁴³ | |
| 704 | H | C₂H₅ | Cl | O | — | T¹⁴³ | |
| 705 | H | (CH₂)₄ | | O | — | T¹⁴³ | |
| 706 | H | CH₂OCH₃ | OCH₃ | NH | — | T¹⁴⁴ | |
| 707 | H | CH₂OCH₃ | OCH₃ | O | — | T¹⁴⁴ | |
| 708 | H | C₂H₅ | Cl | NH | — | T¹⁴⁴ | |
| 709 | H | C₂H₅ | Cl | O | — | T¹⁴⁴ | |
| 710 | H | (CH₂)₄ | | O | — | T¹⁴⁴ | |
| 711 | H | CH₂OCH₃ | OCH₃ | NH | — | T¹⁴⁵ | |
| 712 | H | CH₂OCH₃ | OCH₃ | O | — | T¹⁴⁵ | |
| 713 | H | C₂H₅ | Cl | NH | — | T¹⁴⁵ | |
| 714 | H | C₂H₅ | Cl | O | — | T¹⁴⁵ | |

TABLE I-continued

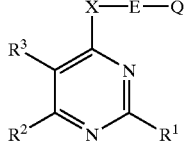

| Example No. | R¹ | R² | R³ | X | E | Q | M.p. [° C.] |
|---|---|---|---|---|---|---|---|
| 715 | H | (CH₂)₄ | | O | — | T¹⁴⁵ | |
| 716 | H | CH₂OCH₃ | OCH₃ | NH | — | T¹⁴⁶ | |
| 717 | H | CH₂OCH₃ | OCH₃ | O | — | T¹⁴⁶ | |
| 718 | H | C₂H₅ | Cl | NH | — | T¹⁴⁶ | |
| 719 | H | C₂H₅ | Cl | O | — | T¹⁴⁶ | |
| 720 | H | (CH₂)₄ | | O | — | T¹⁴⁶ | |
| 721 | H | CH₂OCH₃ | OCH₃ | NH | — | T¹⁴⁷ | |
| 722 | H | CH₂OCH₃ | OCH₃ | O | — | T¹⁴⁷ | |
| 723 | H | C₂H₅ | Cl | NH | — | T¹⁴⁷ | |
| 724 | H | C₂H₅ | Cl | O | — | T¹⁴⁷ | |
| 725 | H | (CH₂)₄ | | O | — | T¹⁴⁷ | |
| 726 | H | CH₂OCH₃ | OCH₃ | NH | — | T¹⁴⁸ | |
| 727 | H | CH₂OCH₃ | OCH₃ | O | — | T¹⁴⁸ | |
| 728 | H | C₂H₅ | Cl | NH | — | T¹⁴⁸ | |
| 729 | H | C₂H₅ | Cl | O | — | T¹⁴⁸ | |
| 730 | H | (CH₂)₄ | | O | — | T¹⁴⁸ | |
| 731 | H | CH₂OCH₃ | OCH₃ | NH | — | T¹⁴⁹ | |
| 732 | H | CH₂OCH₃ | OCH₃ | O | — | T¹⁴⁹ | |
| 733 | H | C₂H₅ | Cl | NH | — | T¹⁴⁹ | |
| 734 | H | C₂H₅ | Cl | O | — | T¹⁴⁹ | |
| 735 | H | (CH₂)₄ | | O | — | T¹⁴⁹ | |
| 736 | H | CH₂OCH₃ | OCH₃ | NH | — | T¹⁵⁰ | |
| 737 | H | CH₂OCH₃ | OCH₃ | O | — | T¹⁵⁰ | |
| 738 | H | C₂H₅ | Cl | NH | — | T¹⁵⁰ | |
| 739 | H | C₂H₅ | Cl | O | — | T¹⁵⁰ | |
| 740 | H | (CH₂)₄ | | O | — | T¹⁵⁰ | |
| 741 | H | CH₂OCH₃ | OCH₃ | NH | — | T¹⁵¹ | 93–94 |
| 742 | H | CH₂OCH₃ | OCH₃ | O | — | T¹⁵¹ | oil |
| 743 | H | C₂H₅ | Cl | NH | — | T¹⁵¹ | 110–111 |
| 744 | H | C₂H₅ | Cl | O | — | T¹⁵¹ | 72 |
| 745 | H | (CH₂)₄ | | O | — | T¹⁵¹ | 108 |
| 746 | H | CH₂OCH₃ | OCH₃ | NH | — | T¹⁵² | oil |
| 747 | H | CH₂OCH₃ | OCH₃ | O | — | T¹⁵² | |
| 748 | H | C₂H₅ | Cl | NH | — | T¹⁵² | 87–88 |
| 749 | H | C₂H₅ | Cl | O | — | T¹⁵² | |
| 750 | H | (CH₂)₄ | | O | — | T¹⁵² | |
| 751 | H | CH₂OCH₃ | OCH₃ | NH | — | T¹⁵³ | |
| 752 | H | CH₂OCH₃ | OCH₃ | O | — | T¹⁵³ | |
| 753 | H | C₂H₅ | Cl | NH | — | T¹⁵³ | |
| 754 | H | C₂H₅ | Cl | O | — | T¹⁵³ | |
| 755 | H | (CH₂)₄ | | O | — | T¹⁵³ | |
| 756 | H | CH₂OCH₃ | OCH₃ | NH | — | T¹⁵⁴ | |
| 757 | H | CH₂OCH₃ | OCH₃ | O | — | T¹⁵⁴ | |
| 758 | H | C₂H₅ | Cl | NH | — | T¹⁵⁴ | oil |
| 759 | H | C₂H₅ | Cl | O | — | T¹⁵⁴ | |
| 760 | H | (CH₂)₄ | | O | — | T¹⁵⁴ | |
| 761 | H | CH₂OCH₃ | OCH₃ | NH | — | T¹⁵⁵ | |
| 762 | H | CH₂OCH₃ | OCH₃ | O | — | T¹⁵⁵ | |
| 763 | H | C₂H₅ | Cl | NH | — | T¹⁵⁵ | oil |
| 764 | H | C₂H₅ | Cl | O | — | T¹⁵⁵ | |
| 765 | H | (CH₂)₄ | | O | — | T¹⁵⁵ | |
| 766 | H | CH₂OCH₃ | OCH₃ | NH | — | T¹⁵⁶ | |
| 767 | H | CH₂OCH₃ | OCH₃ | O | — | T¹⁵⁶ | |
| 768 | H | C₂H₅ | Cl | NH | — | T¹⁵⁶ | |
| 769 | H | C₂H₅ | Cl | O | — | T¹⁵⁶ | |
| 770 | H | (CH₂)₄ | | O | — | T¹⁵⁶ | |
| 771 | H | CH₂OCH₃ | OCH₃ | NH | — | T¹⁵⁷ | |
| 772 | H | CH₂OCH₃ | OCH₃ | O | — | T¹⁵⁷ | |
| 773 | H | C₂H₅ | Cl | NH | — | T¹⁵⁷ | |
| 774 | H | C₂H₅ | Cl | O | — | T¹⁵⁷ | |
| 775 | H | (CH₂)₄ | | O | — | T¹⁵⁷ | |
| 776 | H | CH₂OCH₃ | OCH₃ | NH | — | T¹⁵⁸ | |
| 777 | H | CH₂OCH₃ | OCH₃ | O | — | T¹⁵⁸ | |
| 778 | H | C₂H₅ | Cl | NH | — | T¹⁵⁸ | |
| 779 | H | C₂H₅ | Cl | O | — | T¹⁵⁸ | |

TABLE I-continued

| Example No. | R¹ | R² | R³ | X | E | Q | M.p. [° C.] |
|---|---|---|---|---|---|---|---|
| 780 | H | (CH$_2$)$_4$ | | O | — | T$^{158}$ | |
| 781 | H | CH$_2$OCH$_3$ | OCH$_3$ | NH | — | T$^{159}$ | |
| 782 | H | CH$_2$OCH$_3$ | OCH$_3$ | O | — | T$^{159}$ | |
| 783 | H | C$_2$H$_5$ | Cl | NH | — | T$^{159}$ | |
| 784 | H | C$_2$H$_5$ | Cl | O | — | T$^{159}$ | |
| 785 | H | (CH$_2$)$_4$ | | O | — | T$^{159}$ | |
| 786 | H | CH$_2$OCH$_3$ | OCH$_3$ | NH | — | T$^{160}$ | oil |
| 787 | H | CH$_2$OCH$_3$ | OCH$_3$ | O | — | T$^{160}$ | |
| 788 | H | C$_2$H$_5$ | Cl | NH | — | T$^{160}$ | oil |
| 789 | H | C$_2$H$_5$ | Cl | O | — | T$^{160}$ | |
| 790 | H | (CH$_2$)$_4$ | | O | — | T$^{160}$ | |
| 791 | H | CH$_2$OCH$_3$ | OCH$_3$ | NH | — | T$^{161}$ | oil |
| 792 | H | CH$_2$OCH$_3$ | OCH$_3$ | O | — | T$^{161}$ | |
| 793 | H | C$_2$H$_5$ | Cl | NH | — | T$^{161}$ | oil |
| 794 | H | C$_2$H$_5$ | Cl | O | — | T$^{161}$ | |
| 795 | H | (CH$_2$)$_4$ | | O | — | T$^{161}$ | |
| 796 | H | CH$_2$OCH$_3$ | OCH$_3$ | NH | — | T$^{162}$ | |
| 797 | H | CH$_2$OCH$_3$ | OCH$_3$ | O | — | T$^{162}$ | |
| 798 | H | C$_2$H$_5$ | Cl | NH | — | T$^{162}$ | |
| 799 | H | C$_2$H$_5$ | Cl | O | — | T$^{162}$ | |
| 800 | H | (CH$_2$)$_4$ | | O | — | T$^{162}$ | |
| 801 | H | CH$_2$OCH$_3$ | OCH$_3$ | NH | — | T$^{163}$ | |
| 802 | H | CH$_2$OCH$_3$ | OCH$_3$ | O | — | T$^{163}$ | |
| 803 | H | C$_2$H$_5$ | Cl | NH | — | T$^{163}$ | |
| 804 | H | C$_2$H$_5$ | Cl | O | — | T$^{163}$ | |
| 805 | H | (CH$_2$)$_4$ | | O | — | T$^{163}$ | |
| 806 | H | CH$_2$OCH$_3$ | OCH$_3$ | NH | — | T$^{164}$ | |
| 807 | H | CH$_2$OCH$_3$ | OCH$_3$ | O | — | T$^{164}$ | |
| 808 | H | C$_2$H$_5$ | Cl | NH | — | T$^{164}$ | |
| 809 | H | C$_2$H$_5$ | Cl | O | — | T$^{164}$ | |
| 810 | H | (CH$_2$)$_4$ | | O | — | T$^{164}$ | |
| 811 | H | CH$_2$OCH$_3$ | OCH$_3$ | NH | — | T$^{165}$ | |
| 812 | H | CH$_2$OCH$_3$ | OCH$_3$ | O | — | T$^{165}$ | |
| 813 | H | C$_2$H$_5$ | Cl | NH | — | T$^{165}$ | |
| 814 | H | C$_2$H$_5$ | Cl | O | — | T$^{165}$ | |
| 815 | H | (CH$_2$)$_4$ | | O | — | T$^{165}$ | |
| 816 | H | CH$_2$OCH$_3$ | OCH$_3$ | NH | — | T$^{166}$ | |
| 817 | H | CH$_2$OCH$_3$ | OCH$_3$ | O | — | T$^{166}$ | |
| 818 | H | C$_2$H$_5$ | Cl | NH | — | T$^{166}$ | |
| 819 | H | C$_2$H$_5$ | Cl | O | — | T$^{166}$ | |
| 820 | H | (CH$_2$)$_4$ | | O | — | T$^{166}$ | |
| 821 | H | CH$_2$OCH$_3$ | OCH$_3$ | NH | — | T$^{167}$ | |
| 822 | H | CH$_2$OCH$_3$ | OCH$_3$ | O | — | T$^{167}$ | |
| 823 | H | C$_2$H$_5$ | Cl | NH | — | T$^{167}$ | |
| 824 | H | C$_2$H$_5$ | Cl | O | — | T$^{167}$ | |
| 825 | H | (CH$_2$)$_4$ | | O | — | T$^{167}$ | |
| 826 | H | CH$_2$OCH$_3$ | OCH$_3$ | NH | — | T$^{168}$ | |
| 827 | H | CH$_2$OCH$_3$ | OCH$_3$ | O | — | T$^{168}$ | |
| 828 | H | C$_2$H$_5$ | Cl | NH | — | T$^{168}$ | |
| 829 | H | C$_2$H$_5$ | Cl | O | — | T$^{168}$ | |
| 830 | H | (CH$_2$)$_4$ | | O | — | T$^{168}$ | |
| 831 | H | CH$_2$OCH$_3$ | OCH$_3$ | NH | — | T$^{169}$ | |
| 832 | H | CH$_2$OCH$_3$ | OCH$_3$ | O | — | T$^{169}$ | |
| 833 | H | C$_2$H$_5$ | Cl | NH | — | T$^{169}$ | |
| 834 | H | C$_2$H$_5$ | Cl | O | — | T$^{169}$ | |
| 835 | H | (CH$_2$)$_4$ | | O | — | T$^{169}$ | |
| 836 | H | CH$_2$OCH$_3$ | OCH$_3$ | NH | — | T$^{170}$ | |
| 837 | H | CH$_2$OCH$_3$ | OCH$_3$ | O | — | T$^{170}$ | |
| 838 | H | C$_2$H$_5$ | Cl | NH | — | T$^{170}$ | |
| 839 | H | C$_2$H$_5$ | Cl | O | — | T$^{170}$ | |
| 840 | H | (CH$_2$)$_4$ | | O | — | T$^{170}$ | |
| 841 | H | CH$_2$OCH$_3$ | OCH$_3$ | NH | — | T$^{171}$ | |
| 842 | H | CH$_2$OCH$_3$ | OCH$_3$ | O | — | T$^{171}$ | |
| 843 | H | C$_2$H$_5$ | Cl | NH | — | T$^{171}$ | |
| 844 | H | C$_2$H$_5$ | Cl | O | — | T$^{171}$ | |

TABLE I-continued

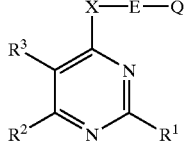

| Example No. | $R^1$ | $R^2$ | $R^3$ | X | E | Q | M.p. [° C.] |
|---|---|---|---|---|---|---|---|
| 845 | H | (CH$_2$)$_4$ | | O | — | T$^{171}$ | |
| 846 | H | CH$_2$OCH$_3$ | OCH$_3$ | NH | — | T$^{172}$ | |
| 847 | H | CH$_2$OCH$_3$ | OCH$_3$ | O | — | T$^{172}$ | |
| 848 | H | C$_2$H$_5$ | Cl | NH | — | T$^{172}$ | |
| 849 | H | C$_2$H$_5$ | Cl | O | — | T$^{172}$ | |
| 850 | H | (CH$_2$)$_4$ | | O | — | T$^{172}$ | |
| 851 | H | CH$_2$OCH$_3$ | OCH$_3$ | NH | — | T$^{173}$ | |
| 852 | H | CH$_2$OCH$_3$ | OCH$_3$ | O | — | T$^{173}$ | |
| 853 | H | C$_2$H$_5$ | Cl | NH | — | T$^{173}$ | |
| 854 | H | C$_2$H$_5$ | Cl | O | — | T$^{173}$ | |
| 855 | H | (CH$_2$)$_4$ | | O | — | T$^{173}$ | |
| 856 | H | CH$_2$OCH$_3$ | OCH$_3$ | NH | — | T$^{174}$ | |
| 857 | H | CH$_2$OCH$_3$ | OCH$_3$ | O | — | T$^{174}$ | |
| 858 | H | C$_2$H$_5$ | Cl | NH | — | T$^{174}$ | oil |
| 859 | H | C$_2$H$_5$ | Cl | O | — | T$^{174}$ | |
| 860 | H | (CH$_2$)$_4$ | | O | — | T$^{174}$ | |
| 861 | H | CH$_2$OCH$_3$ | OCH$_3$ | NH | — | T$^{175}$ | |
| 862 | H | CH$_2$OCH$_3$ | OCH$_3$ | O | — | T$^{175}$ | |
| 863 | H | C$_2$H$_5$ | Cl | NH | — | T$^{175}$ | oil |
| 864 | H | C$_2$H$_5$ | Cl | O | — | T$^{175}$ | |
| 865 | H | (CH$_2$)$_4$ | | O | — | T$^{175}$ | |
| 866 | H | CH$_2$OCH$_3$ | OCH$_3$ | NH | — | T$^{176}$ | |
| 867 | H | CH$_2$OCH$_3$ | OCH$_3$ | O | — | T$^{176}$ | |
| 868 | H | C$_2$H$_5$ | Cl | NH | — | T$^{176}$ | |
| 869 | H | C$_2$H$_5$ | Cl | O | — | T$^{176}$ | |
| 870 | H | (CH$_2$)$_4$ | | O | — | T$^{176}$ | |
| 871 | H | CH$_2$OCH$_3$ | OCH$_3$ | NH | — | T$^{177}$ | |
| 872 | H | CH$_2$OCH$_3$ | OCH$_3$ | O | — | T$^{177}$ | |
| 873 | H | C$_2$H$_5$ | Cl | NH | — | T$^{177}$ | |
| 874 | H | C$_2$H$_5$ | Cl | O | — | T$^{177}$ | |
| 875 | H | (CH$_2$)$_4$ | | O | — | T$^{177}$ | |
| 876 | H | CH$_2$OCH$_3$ | OCH$_3$ | NH | — | T$^{178}$ | |
| 877 | H | CH$_2$OCH$_3$ | OCH$_3$ | O | — | T$^{178}$ | |
| 878 | H | C$_2$H$_5$ | Cl | NH | — | T$^{178}$ | |
| 879 | H | C$_2$H$_5$ | Cl | O | — | T$^{178}$ | |
| 880 | H | (CH$_2$)$_4$ | | O | — | T$^{178}$ | |
| 881 | H | CH$_2$OCH$_3$ | OCH$_3$ | NH | — | T$^{179}$ | |
| 882 | H | CH$_2$OCH$_3$ | OCH$_3$ | O | — | T$^{179}$ | |
| 883 | H | C$_2$H$_5$ | Cl | NH | — | T$^{179}$ | |
| 884 | H | C$_2$H$_5$ | Cl | O | — | T$^{179}$ | |
| 885 | H | (CH$_2$)$_4$ | | O | — | T$^{179}$ | |
| 886 | H | CH$_2$OCH$_3$ | OCH$_3$ | NH | — | T$^{180}$ | |
| 887 | H | CH$_2$OCH$_3$ | OCH$_3$ | O | — | T$^{180}$ | |
| 888 | H | C$_2$H$_5$ | Cl | NH | — | T$^{180}$ | oil |
| 889 | H | C$_2$H$_5$ | Cl | O | — | T$^{180}$ | |
| 890 | H | (CH$_2$)$_4$ | | O | — | T$^{180}$ | |
| 891 | H | CH$_2$OCH$_3$ | OCH$_3$ | NH | — | T$^{181}$ | |
| 892 | H | CH$_2$OCH$_3$ | OCH$_3$ | O | — | T$^{181}$ | |
| 893 | H | C$_2$H$_5$ | Cl | NH | — | T$^{181}$ | |
| 894 | H | C$_2$H$_5$ | Cl | O | — | T$^{181}$ | |
| 895 | H | (CH$_2$)$_4$ | | O | — | T$^{181}$ | |
| 896 | H | CH$_2$OCH$_3$ | OCH$_3$ | NH | — | T$^{182}$ | |
| 897 | H | CH$_2$OCH$_3$ | OCH$_3$ | O | — | T$^{182}$ | |
| 898 | H | C$_2$H$_5$ | Cl | NH | — | T$^{182}$ | |
| 899 | H | C$_2$H$_5$ | Cl | O | — | T$^{182}$ | |
| 900 | H | (CH$_2$)$_4$ | | O | — | T$^{182}$ | |
| 901 | H | CH$_2$OCH$_3$ | OCH$_3$ | NH | — | T$^{183}$ | |
| 902 | H | CH$_2$OCH$_3$ | OCH$_3$ | O | — | T$^{183}$ | |
| 903 | H | C$_2$H$_5$ | Cl | NH | — | T$^{183}$ | |
| 904 | H | C$_2$H$_5$ | Cl | O | — | T$^{183}$ | |
| 905 | H | (CH$_2$)$_4$ | | O | — | T$^{183}$ | |
| 906 | H | CH$_2$OCH$_3$ | OCH$_3$ | NH | — | T$^{184}$ | |
| 907 | H | CH$_2$OCH$_3$ | OCH$_3$ | O | — | T$^{184}$ | |
| 908 | H | C$_2$H$_5$ | Cl | NH | — | T$^{184}$ | |
| 909 | H | C$_2$H$_5$ | Cl | O | — | T$^{184}$ | |

TABLE I-continued $$\underset{R^2}{\overset{R^3}{\prod}}\underset{N}{\overset{X-E-Q}{\underset{\|}{\bigvee}}}R^1$$

| Example No. | R¹ | R² | R³ | X | E | Q | M.p. [° C.] |
|---|---|---|---|---|---|---|---|
| 910 | H | (CH$_2$)$_4$ | | O | — | T$^{184}$ | |
| 911 | H | CH$_2$OCH$_3$ | OCH$_3$ | NH | — | T$^{185}$ | |
| 912 | H | CH$_2$OCH$_3$ | OCH$_3$ | O | — | T$^{185}$ | |
| 913 | H | C$_2$H$_5$ | Cl | NH | — | T$^{185}$ | |
| 914 | H | C$_2$H$_5$ | Cl | O | — | T$^{185}$ | |
| 915 | H | (CH$_2$)$_4$ | | O | — | T$^{185}$ | |
| 916 | H | CH$_2$OCH$_3$ | OCH$_3$ | NH | — | T$^{186}$ | |
| 917 | H | CH$_2$OCH$_3$ | OCH$_3$ | O | — | T$^{186}$ | |
| 918 | H | C$_2$H$_5$ | Cl | NH | — | T$^{186}$ | oil |
| 919 | H | C$_2$H$_5$ | Cl | O | — | T$^{186}$ | |
| 920 | H | (CH$_2$)$_4$ | | O | — | T$^{186}$ | |
| 921 | H | CH$_2$OCH$_3$ | OCH$_3$ | NH | — | T$^{187}$ | |
| 922 | H | CH$_2$OCH$_3$ | OCH$_3$ | O | — | T$^{187}$ | |
| 923 | H | C$_2$H$_5$ | Cl | NH | — | T$^{187}$ | |
| 924 | H | C$_2$H$_5$ | Cl | O | — | T$^{187}$ | |
| 925 | H | (CH$_2$)$_4$ | | O | — | T$^{187}$ | |
| 926 | H | CH$_2$OCH$_3$ | OCH$_3$ | NH | — | T$^{188}$ | |
| 927 | H | CH$_2$OCH$_3$ | OCH$_3$ | O | — | T$^{188}$ | |
| 928 | H | C$_2$H$_5$ | Cl | NH | — | T$^{188}$ | |
| 929 | H | C$_2$H$_5$ | Cl | O | — | T$^{188}$ | |
| 930 | H | (CH$_2$)$_4$ | | O | — | T$^{188}$ | |
| 931 | H | CH$_2$OCH$_3$ | OCH$_3$ | NH | — | T$^{189}$ | |
| 932 | H | CH$_2$OCH$_3$ | OCH$_3$ | O | — | T$^{189}$ | |
| 933 | H | C$_2$H$_5$ | Cl | NH | — | T$^{189}$ | |
| 934 | H | C$_2$H$_5$ | Cl | O | — | T$^{189}$ | |
| 935 | H | (CH$_2$)$_4$ | | O | — | T$^{189}$ | |
| 936 | H | CH$_2$OCH$_3$ | OCH$_3$ | NH | — | T$^{190}$ | |
| 937 | H | CH$_2$OCH$_3$ | OCH$_3$ | O | — | T$^{190}$ | |
| 938 | H | C$_2$H$_5$ | Cl | NH | — | T$^{190}$ | |
| 939 | H | C$_2$H$_5$ | Cl | O | — | T$^{190}$ | |
| 940 | H | (CH$_2$)$_4$ | | O | — | T$^{190}$ | |
| 941 | H | CH$_2$OCH$_3$ | OCH$_3$ | NH | — | T$^{191}$ | |
| 942 | H | CH$_2$OCH$_3$ | OCH$_3$ | O | — | T$^{191}$ | |
| 943 | H | C$_2$H$_5$ | Cl | NH | — | T$^{191}$ | |
| 944 | H | C$_2$H$_5$ | Cl | O | — | T$^{191}$ | |
| 945 | H | (CH$_2$)$_4$ | | O | — | T$^{191}$ | |
| 946 | H | CH$_2$OCH$_3$ | OCH$_3$ | NH | — | T$^{192}$ | |
| 947 | H | CH$_2$OCH$_3$ | OCH$_3$ | O | — | T$^{192}$ | |
| 948 | H | C$_2$H$_5$ | Cl | NH | — | T$^{192}$ | |
| 949 | H | C$_2$H$_5$ | Cl | O | — | T$^{192}$ | |
| 950 | H | (CH$_2$)$_4$ | | O | — | T$^{192}$ | |
| 951 | H | CH$_2$OCH$_3$ | OCH$_3$ | NH | — | T$^{193}$ | |
| 952 | H | CH$_2$OCH$_3$ | OCH$_3$ | O | — | T$^{193}$ | |
| 953 | H | C$_2$H$_5$ | Cl | NH | — | T$^{193}$ | |
| 954 | H | C$_2$H$_5$ | Cl | O | — | T$^{193}$ | |
| 955 | H | (CH$_2$)$_4$ | | O | — | T$^{193}$ | |
| 956 | H | CH$_2$OCH$_3$ | OCH$_3$ | NH | — | T$^{194}$ | |
| 957 | H | CH$_2$OCH$_3$ | OCH$_3$ | O | — | T$^{194}$ | |
| 958 | H | C$_2$H$_5$ | Cl | NH | — | T$^{194}$ | |
| 959 | H | C$_2$H$_5$ | Cl | O | — | T$^{194}$ | |
| 960 | H | (CH$_2$)$_4$ | | O | — | T$^{194}$ | |
| 961 | H | CH$_2$OCH$_3$ | OCH$_3$ | NH | — | T$^{195}$ | |
| 962 | H | CH$_2$OCH$_3$ | OCH$_3$ | O | — | T$^{195}$ | |
| 963 | H | C$_2$H$_5$ | Cl | NH | — | T$^{195}$ | |
| 964 | H | C$_2$H$_5$ | Cl | O | — | T$^{195}$ | |
| 965 | H | (CH$_2$)$_4$ | | O | — | T$^{195}$ | |
| 966 | H | CH$_2$OCH$_3$ | OCH$_3$ | NH | — | T$^{196}$ | |
| 967 | H | CH$_2$OCH$_3$ | OCH$_3$ | O | — | T$^{196}$ | |
| 968 | H | C$_2$H$_5$ | Cl | NH | — | T$^{196}$ | |
| 969 | H | C$_2$H$_5$ | Cl | O | — | T$^{196}$ | |
| 970 | H | (CH$_2$)$_4$ | | O | — | T$^{196}$ | |
| 971 | H | CH$_2$OCH$_3$ | OCH$_3$ | NH | — | T$^{197}$ | |
| 972 | H | CH$_2$OCH$_3$ | OCH$_3$ | O | — | T$^{197}$ | |
| 973 | H | C$_2$H$_5$ | Cl | NH | — | T$^{197}$ | |
| 974 | H | C$_2$H$_5$ | Cl | O | — | T$^{197}$ | |

TABLE I-continued structure: X—E—Q attached to pyrimidine ring with $R^3$ at 5-position, $R^2$ at 6-position, $R^1$ at 2-position

| Example No. | $R^1$ | $R^2$ | $R^3$ | X | E | Q | M.p. [° C.] |
|---|---|---|---|---|---|---|---|
| 975 | H | $(CH_2)_4$ | | O | — | $T^{197}$ | |
| 976 | H | $CH_2OCH_3$ | $OCH_3$ | NH | — | $T^{198}$ | |
| 977 | H | $CH_2OCH_3$ | $OCH_3$ | O | — | $T^{198}$ | |
| 978 | H | $C_2H_5$ | Cl | NH | — | $T^{198}$ | |
| 979 | H | $C_2H_5$ | Cl | O | — | $T^{198}$ | |
| 980 | H | $(CH_2)_4$ | | O | — | $T^{198}$ | |
| 981 | H | $CH_2OCH_3$ | $OCH_3$ | NH | — | $T^{199}$ | |
| 982 | H | $CH_2OCH_3$ | $OCH_3$ | O | — | $T^{199}$ | |
| 983 | H | $C_2H_5$ | Cl | NH | — | $T^{199}$ | |
| 984 | H | $C_2H_5$ | Cl | O | — | $T^{199}$ | |
| 985 | H | $(CH_2)_4$ | | O | — | $T^{199}$ | |
| 986 | H | $CH_2OCH_3$ | $OCH_3$ | NH | — | $T^{200}$ | |
| 987 | H | $CH_2OCH_3$ | $OCH_3$ | O | — | $T^{200}$ | |
| 988 | H | $C_2H_5$ | Cl | NH | — | $T^{200}$ | |
| 989 | H | $C_2H_5$ | Cl | O | — | $T^{200}$ | |
| 990 | H | $(CH_2)_4$ | | — | O | $T^{200}$ | |
| 991 | H | $CH_2OCH_3$ | $OCH_3$ | — | NH | $T^{201}$ | |
| 992 | H | $CH_2OCH_3$ | $OCH_3$ | — | O | $T^{201}$ | |
| 993 | H | $C_2H_5$ | Cl | — | NH | $T^{201}$ | |
| 994 | H | $C_2H_5$ | Cl | — | O | $T^{201}$ | |
| 995 | H | $(CH_2)_4$ | | — | O | $T^{201}$ | |
| 996 | H | $C_2H_5$ | Cl | — | NH | $T^4$ | 177–178 |
| 997 | H | $C_2H_5$ | Cl | — | NH | $T^7$ | 177–178 |
| 998 | H | $C_2H_5$ | I | — | NH | $T^7$ | |
| 999 | H | $C_2H_5$ | I | — | NH | $T^{14}$ | |
| 1000 | H | $(CH_2)_2CH_3$ | Cl | — | NH | $T^{23}$ | |
| 1001 | H | $C_2H_5$ | I | — | NH | $T^{76}$ | |
| 1002 | H | $CH_2OCH_3$ | $OCH_3$ | — | NH | $T^{202}$ | |
| 1003 | H | $CH_2OCH_3$ | $OCH_3$ | — | O | $T^{202}$ | |
| 1004 | H | $C_2H_5$ | Cl | — | NH | $T^{202}$ | |
| 1005 | H | $C_2H_5$ | $OCH_3$ | — | O | $T^{202}$ | |
| 1006 | H | $(CH_2)_4$ | | — | O | $T^{202}$ | |
| 1007 | H | $CH_2OCH_3$ | $OCH_3$ | NH | — | $T^{203}$ | |
| 1008 | H | $CH_2OCH_3$ | $OCH_3$ | O | — | $T^{203}$ | |
| 1009 | H | $C_2H_5$ | Cl | NH | — | $T^{203}$ | |
| 1010 | H | $C_2H_5$ | Cl | O | — | $T^{203}$ | |
| 1011 | H | $(CH_2)_4$ | | O | — | $T^{203}$ | |
| 1012 | H | $CH_2OCH_3$ | $OCH_3$ | NH | — | $T^{204}$ | |
| 1013 | H | $CH_2OCH_3$ | $OCH_3$ | O | — | $T^{204}$ | |
| 1014 | H | $C_2H_5$ | Cl | NH | — | $T^{204}$ | |
| 1015 | H | $C_2H_5$ | Cl | O | — | $T^{204}$ | |
| 1016 | H | $(CH_2)_4$ | | O | — | $T^{204}$ | |
| 1017 | H | $CH_2OCH_3$ | $OCH_3$ | NH | — | $T^{205}$ | |
| 1018 | H | $CH_2OCH_3$ | $OCH_3$ | O | — | $T^{205}$ | |
| 1019 | H | $C_2H_5$ | Cl | NH | — | $T^{205}$ | |
| 1020 | H | $C_2H_5$ | Cl | O | — | $T^{205}$ | |
| 1021 | H | $(CH_2)_4$ | | O | — | $T^{206}$ | |
| 1022 | H | $CH_2OCH_3$ | $OCH_3$ | NH | — | $T^{206}$ | |
| 1023 | H | $CH_2OCH_3$ | $OCH_3$ | O | — | $T^{206}$ | |
| 1024 | H | $C_2H_5$ | Cl | NH | — | $T^{206}$ | |
| 1025 | H | $C_2H_5$ | Cl | O | — | $T^{206}$ | |
| 1026 | H | $(CH_2)_4$ | | O | — | $T^{206}$ | |
| 1027 | H | $CH_2OCH_3$ | $OCH_3$ | NH | — | $T^{207}$ | |
| 1028 | H | $CH_2OCH_3$ | $OCH_3$ | O | — | $T^{207}$ | |
| 1029 | H | $C_2H_5$ | Cl | NH | — | $T^{207}$ | |
| 1030 | H | $C_2H_5$ | Cl | O | — | $T^{207}$ | |
| 1031 | H | $(CH_2)_4$ | | O | — | $T^{207}$ | |
| 1032 | H | $CH_2OCH_3$ | $OCH_3$ | NH | — | $T^{208}$ | |
| 1033 | H | $CH_2OCH_3$ | $OCH_3$ | O | — | $T^{208}$ | |
| 1034 | H | $C_2H_5$ | Cl | NH | — | $T^{208}$ | |
| 1035 | H | $C_2H_5$ | Cl | O | — | $T^{208}$ | |
| 1036 | H | $(CH_2)_4$ | | O | — | $T^{208}$ | |
| 1037 | H | $CH_2OCH_3$ | $OCH_3$ | NH | — | $T^{209}$ | |
| 1038 | H | $CH_2OCH_3$ | $OCH_3$ | O | — | $T^{209}$ | |
| 1039 | H | $C_2H_5$ | Cl | NH | — | $T^{209}$ | |

TABLE I-continued

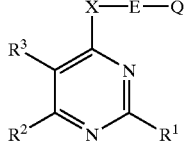

| Example No. | $R^1$ | $R^2$ | $R^3$ | X | E | Q | M.p. [° C.] |
|---|---|---|---|---|---|---|---|
| 1040 | H | $C_2H_5$ | Cl | O | — | $T^{209}$ | |
| 1041 | H | $(CH_2)_4$ | | O | — | $T^{209}$ | |
| 1042 | H | $CH_2OCH_3$ | $OCH_3$ | NH | — | $T^{210}$ | |
| 1043 | H | $CH_2OCH_3$ | $OCH_3$ | O | — | $T^{210}$ | |
| 1044 | H | $C_2H_5$ | Cl | NH | — | $T^{210}$ | |
| 1045 | H | $C_2H_5$ | Cl | O | — | $T^{210}$ | |
| 1046 | H | $(CH_2)_4$ | | O | — | $T^{210}$ | |
| 1047 | H | $CH_2OCH_3$ | $OCH_3$ | NH | — | $T^{211}$ | |
| 1048 | H | $CH_2OCH_3$ | $OCH_3$ | O | — | $T^{211}$ | |
| 1049 | H | $C_2H_5$ | Cl | NH | — | $T^{211}$ | |
| 1050 | H | $C_2H_5$ | Cl | O | — | $T^{211}$ | |
| 1051 | H | $(CH_2)_4$ | | O | — | $T^{211}$ | |
| 1052 | H | $CH_2OCH_3$ | $OCH_3$ | NH | — | $T^{212}$ | |
| 1053 | H | $CH_2OCH_3$ | $OCH_3$ | O | — | $T^{212}$ | |
| 1054 | H | $C_2H_5$ | Cl | NH | — | $T^{212}$ | |
| 1055 | H | $C_2H_5$ | Cl | O | — | $T^{212}$ | |
| 1056 | H | $(CH_2)_4$ | | O | — | $T^{212}$ | |
| 1057 | H | $CH_2OCH_3$ | $OCH_3$ | NH | — | $T^{213}$ | |
| 1058 | H | $CH_2OCH_3$ | $OCH_3$ | — | O | $T^{213}$ | |
| 1059 | H | $C_2H_5$ | Cl | — | NH | $T^{213}$ | |
| 1060 | H | $C_2H_5$ | Cl | — | O | $T^{213}$ | |
| 1061 | H | $(CH_2)_4$ | | — | O | $T^{213}$ | |
| 1062 | H | $CH_2OCH_3$ | $OCH_3$ | — | NH | $T^{214}$ | |
| 1063 | H | $CH_2OCH_3$ | $OCH_3$ | — | O | $T^{214}$ | |
| 1064 | H | $C_2H_5$ | Cl | — | NH | $T^{214}$ | |
| 1065 | H | $C_2H_5$ | Cl | — | O | $T^{214}$ | |
| 1066 | H | $(CH_2)_4$ | | — | O | $T^{214}$ | |
| 1067 | H | $CH_2OCH_3$ | $OCH_3$ | — | NH | $T^{215}$ | |
| 1068 | H | $CH_2OCH_3$ | $OCH_3$ | — | O | $T^{215}$ | |
| 1069 | H | $C_2H_5$ | Cl | — | NH | $T^{215}$ | |
| 1070 | H | $C_2H_5$ | Cl | — | O | $T^{215}$ | |
| 1071 | H | $(CH_2)_4$ | | — | O | $T^{215}$ | |
| 1072 | H | $CH_2OCH_3$ | $OCH_3$ | — | NH | $T^{216}$ | |
| 1073 | H | $CH_2OCH_3$ | $OCH_3$ | — | O | $T^{216}$ | |
| 1074 | H | $C_2H_5$ | Cl | — | NH | $T^{216}$ | |
| 1075 | H | $C_2H_5$ | Cl | O | — | $T^{216}$ | |
| 1076 | H | $(CH_2)_4$ | | O | — | $T^{216}$ | |
| 1077 | H | $CH_2OCH_3$ | $OCH_3$ | NH | — | $T^{217}$ | |
| 1078 | H | $CH_2OCH_3$ | $OCH_3$ | O | — | $T^{217}$ | |
| 1079 | H | $C_2H_5$ | Cl | NH | — | $T^{217}$ | |
| 1080 | H | $C_2H_5$ | Cl | O | — | $T^{217}$ | |
| 1081 | H | $(CH_2)_4$ | | O | — | $T^{217}$ | |
| 1082 | H | $CH_2OCH_3$ | $OCH_3$ | NH | — | $T^{218}$ | |
| 1083 | H | $CH_2OCH_3$ | $OCH_3$ | O | — | $T^{218}$ | |
| 1084 | H | $C_2H_5$ | Cl | NH | — | $T^{218}$ | |
| 1085 | H | $C_2H_5$ | Cl | O | — | $T^{218}$ | |
| 1086 | H | $(CH_2)_4$ | | O | — | $T^{218}$ | |
| 1087 | H | $CH_2OCH_3$ | $OCH_3$ | NH | — | $T^{219}$ | |
| 1088 | H | $CH_2OCH_3$ | $OCH_3$ | O | — | $T^{219}$ | |
| 1089 | H | $C_2H_5$ | Cl | NH | — | $T^{219}$ | |
| 1090 | H | $C_2H_5$ | Cl | O | — | $T^{219}$ | |
| 1091 | H | $(CH_2)_4$ | | O | — | $T^{219}$ | |
| 1092 | H | $CH_2OCH_3$ | $OCH_3$ | NH | — | $T^{220}$ | |
| 1093 | H | $CH_2OCH_3$ | $OCH_3$ | O | — | $T^{220}$ | |
| 1094 | H | $C_2H_5$ | Cl | NH | — | $T^{220}$ | |
| 1095 | H | $C_2H_5$ | Cl | O | — | $T^{220}$ | |
| 1096 | H | $(CH_2)_4$ | | O | — | $T^{220}$ | |
| 1097 | H | $CH_2OCH_3$ | $OCH_3$ | NH | — | $T^{221}$ | |
| 1098 | H | $CH_2OCH_3$ | $OCH_3$ | O | — | $T^{221}$ | |
| 1099 | H | $C_2H_5$ | Cl | NH | — | $T^{221}$ | |
| 1100 | H | $C_2H_5$ | Cl | O | — | $T^{221}$ | |
| 1101 | H | $(CH_2)_4$ | | O | — | $T^{221}$ | |
| 1102 | H | $CH_2OCH_3$ | $OCH_3$ | NH | — | $T^{222}$ | |
| 1103 | H | $CH_2OCH_3$ | $OCH_3$ | O | — | $T^{222}$ | |
| 1104 | H | $C_2H_5$ | Cl | NH | — | $T^{222}$ | |

TABLE I-continued

| Example No. | R¹ | R² | R³ | X | E | Q | M.p. [° C.] |
|---|---|---|---|---|---|---|---|
| 1105 | H | C₂H₅ | Cl | O | — | T²²² | |
| 1106 | H | (CH₂)₄ | | O | — | T²²² | |
| 1107 | H | CH₂OCH₃ | OCH₃ | NH | — | T²²³ | |
| 1108 | H | CH₂OCH₃ | OCH₃ | O | — | T²²³ | |
| 1109 | H | C₂H₅ | Cl | NH | — | T²²³ | |
| 1110 | H | C₂H₅ | Cl | O | — | T²²³ | |
| 1111 | H | (CH₂)₄ | | O | — | T²²³ | |
| 1112 | H | CH₂OCH₃ | OCH₃ | NH | — | T²²⁵ | |
| 1113 | H | CH₂OCH₃ | OCH₃ | O | — | T²²⁵ | |
| 1114 | H | C₂H₅ | Cl | NH | — | T²²⁵ | |
| 1115 | H | C₂H₅ | Cl | O | — | T²²⁵ | |
| 1116 | H | (CH₂)₄ | | O | — | T²²⁵ | |
| 1117 | H | CH₂OCH₃ | OCH₃ | NH | — | T²²⁶ | |
| 1118 | H | CH₂OCH₃ | OCH₃ | O | — | T²²⁶ | |
| 1119 | H | C₂H₅ | Cl | NH | — | T²²⁶ | |
| 1120 | H | C₂H₅ | Cl | O | — | T²²⁶ | |
| 1121 | H | (CH₂)₄ | | O | — | T²²⁶ | |
| 1122 | H | CH₂OCH₃ | OCH₃ | NH | — | T²²⁷ | |
| 1123 | H | CH₂OCH₃ | OCH₃ | O | — | T²²⁷ | |
| 1124 | H | C₂H₅ | Cl | NH | — | T²²⁷ | |
| 1125 | H | C₂H₅ | Cl | O | — | T²²⁷ | |
| 1126 | H | (CH₂)₄ | | O | — | T²²⁷ | |
| 1127 | H | CH₂OCH₃ | OCH₃ | NH | — | T²²⁸ | |
| 1128 | H | CH₂OCH₃ | OCH₃ | O | — | T²²⁸ | |
| 1129 | H | C₂H₅ | Cl | NH | — | T²²⁸ | |
| 1130 | H | C₂H₅ | Cl | O | — | T²²⁸ | |
| 1131 | H | (CH₂)₄ | | O | — | T²²⁸ | |
| 1132 | H | CH₂OCH₃ | OCH₃ | NH | — | T²²⁹ | |
| 1133 | H | CH₂OCH₃ | OCH₃ | O | — | T²²⁹ | |
| 1134 | H | C₂H₅ | Cl | NH | — | T²²⁹ | |
| 1135 | H | C₂H₅ | Cl | O | — | T²²⁹ | |
| 1136 | H | (CH₂)₄ | | O | — | T²²⁹ | |
| 1137 | H | CH₂OCH₃ | OCH₃ | NH | — | T²³⁰ | |
| 1138 | H | CH₂OCH₃ | OCH₃ | O | — | T²³⁰ | |
| 1139 | H | C₂H₅ | Cl | NH | — | T²³⁰ | |
| 1140 | H | C₂H₅ | Cl | O | — | T²³⁰ | |
| 1141 | H | (CH₂)₄ | | O | — | T²³⁰ | |
| 1142 | H | CH₂OCH₃ | OCH₃ | NH | — | T²³¹ | |
| 1143 | H | CH₂OCH₃ | OCH₃ | O | — | T²³¹ | |
| 1144 | H | C₂H₅ | Cl | NH | — | T²³¹ | |
| 1145 | H | C₂H₅ | Cl | O | — | T²³¹ | |
| 1146 | H | (CH₂)₄ | | O | — | T²³¹ | |
| 1147 | H | CH₂OCH₃ | OCH₃ | NH | — | T²³² | |
| 1148 | H | CH₂OCH₃ | OCH₃ | O | — | T²³² | |
| 1149 | H | C₂H₅ | Cl | NH | — | T²³² | |
| 1150 | H | C₂H₅ | Cl | O | — | T²³² | |
| 1151 | H | (CH₂)₄ | | O | — | T²³² | |
| 1152 | H | CH₂OCH₃ | OCH₃ | NH | — | T²³³ | |
| 1153 | H | CH₂OCH₃ | OCH₃ | O | — | T²³³ | |
| 1154 | H | C₂H₅ | Cl | NH | — | T²³³ | |
| 1155 | H | C₂H₅ | Cl | O | — | T²³³ | |
| 1156 | H | (CH₂)₄ | | O | — | T²³³ | |
| 1157 | H | CH₂OCH₃ | OCH₃ | NH | — | T²³⁴ | |
| 1158 | H | CH₂OCH₃ | OCH₃ | O | — | T²³⁴ | |
| 1159 | H | C₂H₅ | Cl | NH | — | T²³⁴ | |
| 1160 | H | C₂H₅ | Cl | O | — | T²³⁴ | |
| 1161 | H | (CH₂)₄ | | O | — | T²³⁴ | |
| 1162 | H | CH₂OCH₃ | OCH₃ | NH | — | T²³⁵ | |
| 1163 | H | CH₂OCH₃ | OCH₃ | O | — | T²³⁵ | |
| 1164 | H | C₂H₅ | Cl | NH | — | T²³⁵ | |
| 1165 | H | C₂H₅ | Cl | O | — | T²³⁵ | |
| 1166 | H | (CH₂)₄ | | O | — | T²³⁵ | |
| 1167 | H | CH₂OCH₃ | OCH₃ | NH | — | T²³⁶ | |
| 1168 | H | CH₂OCH₃ | OCH₃ | O | — | T²³⁶ | |
| 1169 | H | C₂H₅ | Cl | NH | — | T²³⁶ | |

TABLE I-continued $$\underset{R^2}{\overset{R^3}{\bigvee}}\underset{N}{\overset{X-E-Q}{\bigvee}}R^1$$

| Example No. | R¹ | R² | R³ | X | E | Q | M.p. [° C.] |
|---|---|---|---|---|---|---|---|
| 1170 | H | C₂H₅ | Cl | O | — | T²³⁶ | |
| 1171 | H | (CH₂)₄ | | O | — | T²³⁶ | |
| 1172 | H | CH₂OCH₃ | OCH₃ | NH | — | T²³⁷ | |
| 1173 | H | CH₂OCH₃ | OCH₃ | O | — | T²³⁷ | |
| 1174 | H | C₂H₅ | Cl | NH | — | T²³⁷ | |
| 1175 | H | C₂H₅ | Cl | O | — | T²³⁷ | |
| 1176 | H | (CH₂)₄ | | O | — | T²³⁷ | |
| 1177 | H | CH₂OCH₃ | OCH₃ | NH | — | T²³⁸ | |
| 1178 | H | CH₂OCH₃ | OCH₃ | O | — | T²³⁸ | |
| 1179 | H | C₂H₅ | Cl | NH | — | T²³⁸ | |
| 1180 | H | C₂H₅ | Cl | O | — | T²³⁸ | |
| 1181 | H | (CH₂)₄ | | O | — | T²³⁸ | |
| 1182 | H | CH₂OCH₃ | OCH₃ | NH | — | T²³⁹ | |
| 1183 | H | CH₂OCH₃ | OCH₃ | O | — | T²³⁹ | |
| 1184 | H | C₂H₅ | Cl | NH | — | T²³⁹ | |
| 1185 | H | C₂H₅ | Cl | O | — | T²³⁹ | |
| 1186 | H | (CH₂)₄ | | O | — | T²³⁹ | |
| 1187 | H | CH₂OCH₃ | OCH₃ | NH | — | T²⁴⁰ | |
| 1188 | H | CH₂OCH₃ | OCH₃ | O | — | T²⁴⁰ | |
| 1189 | H | C₂H₅ | Cl | NH | — | T²⁴⁰ | |
| 1190 | H | C₂H₅ | Cl | O | — | T²⁴⁰ | |
| 1191 | H | (CH₂)₄ | | O | — | T²⁴⁰ | |
| 1192 | H | CH₂OCH₃ | OCH₃ | NH | — | T²⁴¹ | |
| 1193 | H | CH₂OCH₃ | OCH₃ | O | — | T²⁴¹ | |
| 1194 | H | C₂H₅ | Cl | NH | — | T²⁴¹ | |
| 1195 | H | C₂H₅ | Cl | O | — | T²⁴¹ | |
| 1196 | H | (CH₂)₄ | | O | — | T²⁴¹ | |
| 1197 | H | CH₂OCH₃ | OCH₃ | NH | — | T²⁴² | |
| 1198 | H | CH₂OCH₃ | OCH₃ | O | — | T²⁴² | |
| 1199 | H | C₂H₅ | Cl | NH | — | T²⁴² | |
| 1200 | H | C₂H₅ | Cl | O | — | T²⁴² | |
| 1201 | H | (CH₂)₄ | | O | — | T²⁴² | |
| 1202 | H | CH₂OCH₃ | OCH₃ | NH | — | T²⁴³ | |
| 1203 | H | CH₂OCH₃ | OCH₃ | O | — | T²⁴³ | |
| 1204 | H | C₂H₅ | Cl | NH | — | T²⁴³ | |
| 1205 | H | C₂H₅ | Cl | O | — | T²⁴³ | |
| 1206 | H | (CH₂)₄ | | O | — | T²⁴³ | |
| 1207 | H | CH₂OCH₃ | OCH₃ | NH | — | T²⁴⁴ | |
| 1208 | H | CH₂OCH₃ | OCH₃ | O | — | T²⁴⁴ | |
| 1209 | H | C₂H₅ | Cl | NH | — | T²⁴⁴ | |
| 1210 | H | C₂H₅ | Cl | O | — | T²⁴⁴ | |
| 1211 | H | (CH₂)₄ | | O | — | T²⁴⁴ | |
| 1212 | H | CH₂OCH₃ | OCH₃ | NH | — | T²⁴⁵ | |
| 1213 | H | CH₂OCH₃ | OCH₃ | O | — | T²⁴⁵ | |
| 1214 | H | C₂H₅ | Cl | NH | — | T²⁴⁵ | |
| 1215 | H | C₂H₅ | Cl | O | — | T²⁴⁵ | |
| 1216 | H | (CH₂)₄ | | O | — | T²⁴⁵ | |
| 1217 | H | CH₂OCH₃ | OCH₃ | NH | — | T²⁴⁶ | |
| 1218 | H | CH₂OCH₃ | OCH₃ | O | — | T²⁴⁶ | |
| 1219 | H | C₂H₅ | Cl | NH | — | T²⁴⁶ | |
| 1220 | H | C₂H₅ | Cl | O | — | T²⁴⁶ | |
| 1221 | H | (CH₂)₄ | | O | — | T²⁴⁶ | |
| 1222 | H | CH₂OCH₃ | OCH₃ | NH | — | T²⁴⁷ | |
| 1223 | H | CH₂OCH₃ | OCH₃ | O | — | T²⁴⁷ | |
| 1224 | H | C₂H₅ | Cl | NH | — | T²⁴⁷ | |
| 1225 | H | C₂H₅ | Cl | O | — | T²⁴⁷ | |
| 1226 | H | (CH₂)₄ | | O | — | T²⁴⁷ | |
| 1227 | H | CH₂OCH₃ | OCH₃ | NH | — | T²⁴⁸ | |
| 1228 | H | CH₂OCH₃ | OCH₃ | O | — | T²⁴⁸ | |
| 1229 | H | C₂H₅ | Cl | NH | — | T²⁴⁸ | |
| 1230 | H | C₂H₅ | Cl | O | — | T²⁴⁸ | |
| 1231 | H | (CH₂)₄ | | O | — | T²⁴⁸ | |

TABLE II

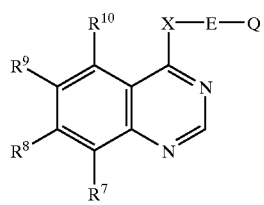

| Example No. | $R^7$ | $R^8$ | $R^9$ | $R^{10}$ | X | E | Q | M.p. [° C.] |
|---|---|---|---|---|---|---|---|---|
| 1232 | H | H | H | H | NH | — | $T^7$ | 135–137 |
| 1233 | H | H | H | H | O | — | $T^7$ | |
| 1234 | H | Cl | H | H | NH | — | $T^7$ | |
| 1235 | H | Cl | H | H | O | — | $T^7$ | |
| 1236 | H | H | Cl | H | NH | — | $T^7$ | |
| 1237 | H | H | Cl | H | O | — | $T^7$ | |
| 1238 | $CH_3$ | H | H | H | NH | — | $T^7$ | |
| 1239 | $CH_3$ | H | H | H | O | — | $T^7$ | |
| 1240 | H | H | $CH_3$ | H | NH | — | $T^7$ | |
| 1241 | H | H | $CH_3$ | H | O | — | $T^7$ | |
| 1242 | H | H | H | $CH_3$ | NH | — | $T^7$ | |
| 1243 | H | H | H | $CH_3$ | O | — | $T^7$ | |
| 1244 | H | H | H | H | NH | — | $T^6$ | 140–142 |
| 1245 | H | H | H | H | NH | — | $T^9$ | 90–92 |
| 1246 | H | H | H | H | O | — | $T^9$ | oil |
| 1247 | H | H | H | H | NH | — | $T^8$ | 143–145 |
| 1248 | H | H | H | H | O | — | $T^8$ | |
| 1249 | H | H | H | H | NH | — | $T^4$ | 158–160 |
| 1250 | H | H | H | H | O | — | $T^4$ | |
| 1251 | H | H | H | H | NH | — | $T^{10}$ | |
| 1252 | H | H | H | H | O | — | $T^{10}$ | |
| 1253 | H | H | H | H | NH | — | $T^{11}$ | |
| 1254 | H | H | H | H | O | — | $T^{11}$ | |
| 1255 | H | H | H | H | NH | — | $T^{12}$ | |
| 1256 | H | H | H | H | O | — | $T^{12}$ | |
| 1257 | H | H | H | H | NH | — | $T^{14}$ | |
| 1258 | H | H | H | H | O | — | $T^{14}$ | |
| 1259 | H | H | H | H | NH | — | $T^{22}$ | 210–211 |
| 1260 | H | H | H | H | NH | — | $T^{23}$ | 153–155 |
| 1261 | H | H | H | H | O | — | $T^{23}$ | |
| 1262 | H | H | H | H | NH | — | $T^{23}$ | |
| 1263 | F | H | H | H | O | — | $T^{23}$ | |
| 1264 | H | H | Cl | H | NH | — | $T^{23}$ | |
| 1265 | H | H | Cl | H | O | — | $T^{23}$ | |
| 1266 | Cl | H | H | H | NH | — | $T^{23}$ | |
| 1267 | Cl | H | H | H | O | — | $T^{23}$ | |
| 1268 | H | H | $CH_3$ | H | NH | — | $T^{23}$ | |
| 1269 | H | H | $CH_3$ | H | O | — | $T^{23}$ | |
| 1270 | H | H | H | $CH_3$ | NH | — | $T^{23}$ | |
| 1271 | H | H | H | $CH_3$ | O | — | $T^{23}$ | |
| 1272 | H | H | H | H | NH | — | $T^{58}$ | 184–185 |
| 1273 | H | H | H | H | NH | — | $T^{13}$ | |
| 1274 | H | H | H | H | O | — | $T^{13}$ | |
| 1275 | H | H | H | H | NH | — | $T^{16}$ | |
| 1276 | H | H | H | H | O | — | $T^{16}$ | |
| 1277 | H | H | H | H | NH | — | $T^{17}$ | |
| 1278 | H | H | H | H | O | — | $T^{17}$ | |
| 1279 | H | H | H | H | NH | — | $T^{19}$ | |
| 1280 | H | H | H | H | O | — | $T^{19}$ | |
| 1281 | H | H | H | H | NH | — | $T^{24}$ | 155–157 |
| 1282 | H | H | H | H | O | — | $T^{24}$ | |
| 1283 | H | H | H | H | NH | — | $T^{25}$ | |
| 1284 | H | H | H | H | O | — | $T^{25}$ | |
| 1285 | H | H | H | H | NH | — | $T^{26}$ | |
| 1286 | H | H | H | H | O | — | $T^{26}$ | |
| 1287 | H | H | H | H | NH | — | $T^{27}$ | |
| 1288 | H | H | H | H | O | — | $T^{27}$ | |
| 1289 | H | H | H | H | NH | — | $T^{28}$ | |
| 1290 | H | H | H | H | O | — | $T^{28}$ | |
| 1291 | H | H | H | H | NH | — | $T^{29}$ | |
| 1292 | H | H | H | H | O | — | $T^{29}$ | |
| 1293 | H | H | H | H | NH | — | $T^{30}$ | |
| 1294 | H | H | H | H | O | — | $T^{30}$ | |
| 1295 | H | H | H | H | NH | — | $T^{31}$ | |
| 1296 | H | H | H | H | O | — | $T^{31}$ | |
| 1297 | H | H | H | H | NH | — | $T^{32}$ | |
| 1298 | H | H | H | H | O | — | $T^{32}$ | |
| 1299 | H | H | H | H | NH | — | $T^{33}$ | |
| 1300 | H | H | H | H | O | — | $T^{33}$ | |
| 1301 | H | H | H | H | NH | — | $T^{34}$ | |
| 1302 | H | H | H | H | O | — | $T^{34}$ | |
| 1303 | H | H | H | H | NH | — | $T^{35}$ | |
| 1304 | H | H | H | H | O | — | $T^{35}$ | |
| 1305 | H | H | H | H | NH | — | $T^{36}$ | |
| 1306 | H | H | H | H | O | — | $T^{36}$ | |
| 1307 | H | H | H | H | NH | — | $T^{37}$ | |
| 1308 | H | H | H | H | O | — | $T^{37}$ | |
| 1309 | H | H | H | H | NH | — | $T^{38}$ | |
| 1310 | H | H | H | H | O | — | $T^{38}$ | |
| 1311 | H | H | H | H | NH | — | $T^{39}$ | |
| 1312 | H | H | H | H | O | — | $T^{39}$ | |
| 1313 | H | H | H | H | NH | — | $T^{40}$ | |
| 1314 | H | H | H | H | O | — | $T^{40}$ | |
| 1315 | H | H | H | H | NH | — | $T^{41}$ | |
| 1316 | H | H | H | H | O | — | $T^{41}$ | |
| 1317 | H | H | H | H | NH | — | $T^{42}$ | |
| 1318 | H | H | H | H | O | — | $T^{42}$ | |
| 1319 | H | H | H | H | NH | — | $T^{44}$ | |
| 1320 | H | H | H | H | O | — | $T^{44}$ | |
| 1321 | H | H | H | H | NH | — | $T^{45}$ | |
| 1322 | H | H | H | H | O | — | $T^{45}$ | |
| 1323 | H | H | H | H | NH | — | $T^{47}$ | |
| 1324 | H | H | H | H | O | — | $T^{47}$ | |
| 1325 | H | H | H | H | NH | — | $T^{50}$ | |
| 1326 | H | H | H | H | O | — | $T^{50}$ | |
| 1327 | H | H | H | H | NH | — | $T^{51}$ | |
| 1328 | H | H | H | H | O | — | $T^{51}$ | |
| 1329 | H | H | H | H | NH | — | $T^{52}$ | |
| 1330 | H | H | H | H | O | — | $T^{52}$ | |
| 1331 | H | H | H | H | NH | — | $T^{54}$ | |
| 1332 | H | H | H | H | O | — | $T^{54}$ | |
| 1333 | H | H | H | H | NH | — | $T^{55}$ | |
| 1334 | H | H | H | H | O | — | $T^{55}$ | 121 |
| 1335 | H | H | H | H | NH | — | $T^{56}$ | |
| 1336 | H | H | H | H | O | — | $T^{56}$ | |
| 1337 | H | H | H | H | NH | — | $T^{59}$ | 144–145 |
| 1338 | H | H | H | H | O | — | $T^{59}$ | |
| 1339 | H | H | H | H | NH | — | $T^{60}$ | |
| 1340 | H | H | H | H | O | — | $T^{60}$ | |
| 1341 | H | H | H | H | NH | — | $T^{61}$ | |
| 1342 | H | H | H | H | O | — | $T^{61}$ | |
| 1343 | H | H | H | H | NH | — | $T^{62}$ | 176 |
| 1344 | H | H | H | H | O | — | $T^{62}$ | 117 |
| 1345 | H | H | H | H | NH | — | $T^{66}$ | |
| 1346 | H | H | H | H | O | — | $T^{66}$ | oil |
| 1347 | H | H | H | H | NH | — | $T^{67}$ | |
| 1348 | H | H | H | H | O | — | $T^{67}$ | |
| 1349 | H | H | H | H | NH | — | $T^{68}$ | glass |
| 1350 | H | H | H | H | O | — | $T^{68}$ | oil |
| 1351 | H | H | H | H | NH | — | $T^{69}$ | |
| 1352 | H | H | H | H | O | — | $T^{69}$ | 69–72 |
| 1353 | H | H | H | H | NH | — | $T^{70}$ | |
| 1354 | H | H | H | H | O | — | $T^{70}$ | |
| 1355 | H | H | H | H | NH | — | $T^{72}$ | |
| 1356 | H | H | H | H | O | — | $T^{72}$ | |
| 1357 | H | H | H | H | NH | — | $T^{73}$ | |
| 1358 | H | H | H | H | O | — | $T^{73}$ | |
| 1359 | H | H | H | H | NH | — | $T^{74}$ | |
| 1360 | H | H | H | H | O | — | $T^{74}$ | 161 |
| 1361 | H | H | H | H | NH | — | $T^{75}$ | |

TABLE II-continued

Structure: R10, R9, R8, R7 substituted quinazoline with X—E—Q at position 4, N at positions 1,3.

| Example No. | R⁷ | R⁸ | R⁹ | R¹⁰ | X | E | Q | M.p. [° C.] |
|---|---|---|---|---|---|---|---|---|
| 1362 | H | H | H | H | O | — | T⁷⁵ | |
| 1363 | H | H | H | H | NH | — | T⁷⁶ | 160–161 |
| 1364 | H | H | H | H | O | — | T⁷⁶ | 103 |
| 1365 | H | H | H | H | NH | — | T⁷⁷ | 224–225 |
| 1366 | H | H | H | H | O | — | T⁷⁷ | |
| 1367 | H | H | H | H | NH | — | T⁷⁸ | |
| 1368 | H | H | H | H | O | — | T⁷⁸ | |
| 1369 | H | H | H | H | NH | — | T⁷⁹ | |
| 1370 | H | H | H | H | O | — | T⁷⁹ | |
| 1371 | H | H | H | H | NH | — | T⁸⁰ | |
| 1372 | H | H | H | H | O | — | T⁸⁰ | 104 |
| 1373 | H | H | H | H | NH | — | T⁸¹ | |
| 1374 | H | H | H | H | O | — | T⁸¹ | |
| 1375 | H | H | H | H | NH | — | T⁸² | 134–136 |
| 1376 | H | H | H | H | O | — | T⁸² | |
| 1377 | H | H | H | H | NH | — | T⁸³ | 158–160 |
| 1378 | H | H | H | H | O | — | T⁸³ | |
| 1379 | H | H | H | H | NH | — | T⁸⁴ | |
| 1380 | H | H | H | H | O | — | T⁸⁴ | |
| 1381 | H | H | H | H | NH | — | T⁸⁵ | |
| 1382 | H | H | H | H | O | — | T⁸⁵ | |
| 1383 | H | H | H | H | NH | — | T⁸⁶ | |
| 1384 | H | H | H | H | O | — | T⁸⁶ | |
| 1385 | H | H | H | H | NH | — | T⁸⁷ | 123–124 |
| 1386 | H | H | H | H | O | — | T⁸⁷ | 75 |
| 1387 | H | H | H | H | NH | — | T⁸⁸ | 156–157 |
| 1388 | H | H | H | H | O | — | T⁸⁸ | |
| 1389 | H | H | H | H | NH | — | T⁸⁹ | |
| 1390 | H | H | H | H | O | — | T⁸⁹ | 65 |
| 1391 | H | H | H | H | NH | — | T⁹⁰ | |
| 1392 | H | H | H | H | O | — | T⁹⁰ | |
| 1393 | H | H | H | H | NH | — | T⁹¹ | |
| 1394 | H | H | H | H | O | — | T⁹¹ | |
| 1395 | H | H | H | H | NH | — | T⁹² | |
| 1396 | H | H | H | H | O | — | T⁹² | |
| 1397 | H | H | H | H | NH | — | T⁹³ | |
| 1398 | H | H | H | H | O | — | T⁹³ | |
| 1399 | H | H | H | H | NH | — | T⁹⁴ | |
| 1400 | H | H | H | H | O | — | T⁹⁴ | 78–81 |
| 1401 | H | H | H | H | NH | — | T⁹⁵ | |
| 1402 | H | H | H | H | O | — | T⁹⁵ | 57 |
| 1403 | H | H | H | H | NH | — | T⁹⁶ | |
| 1404 | H | H | H | H | O | — | T⁹⁶ | |
| 1405 | H | H | H | H | NH | — | T⁹⁷ | |
| 1406 | H | H | H | H | O | — | T⁹⁷ | 97 |
| 1407 | H | H | H | H | NH | — | T⁹⁸ | |
| 1408 | H | H | H | H | O | — | T⁹⁸ | |
| 1409 | H | H | H | H | NH | — | T⁹⁹ | |
| 1410 | H | H | H | H | O | — | T⁹⁹ | |
| 1411 | H | H | H | H | NH | — | T¹⁰⁰ | |
| 1412 | H | H | H | H | O | — | T¹⁰⁰ | |
| 1413 | H | H | H | H | NH | — | T¹⁰¹ | |
| 1414 | H | H | H | H | O | — | T¹⁰¹ | |
| 1415 | H | H | H | H | NH | — | T¹⁰² | |
| 1416 | H | H | H | H | O | — | T¹⁰² | |
| 1417 | H | H | H | H | NH | — | T¹⁰³ | |
| 1418 | H | H | H | H | O | — | T¹⁰³ | |
| 1419 | H | H | H | H | NH | — | T¹⁰⁴ | |
| 1420 | H | H | H | H | O | — | T¹⁰⁴ | 107 |
| 1421 | H | H | H | H | NH | — | T¹⁰⁵ | |
| 1422 | H | H | H | H | O | — | T¹⁰⁵ | |
| 1423 | H | H | H | H | NH | — | T¹⁰⁶ | |
| 1424 | H | H | H | H | O | — | T¹⁰⁶ | |
| 1425 | H | H | H | H | NH | — | T¹⁰⁷ | |
| 1426 | H | H | H | H | O | — | T¹⁰⁷ | oil |
| 1427 | H | H | H | H | NH | — | T¹⁰⁸ | |
| 1428 | H | H | H | H | O | — | T¹⁰⁸ | |
| 1429 | H | H | H | H | NH | — | T¹⁰⁹ | |
| 1430 | H | H | H | H | O | — | T¹⁰⁹ | |
| 1431 | H | H | H | H | NH | — | T¹¹⁰ | |
| 1432 | H | H | H | H | O | — | T¹¹⁰ | |
| 1433 | H | H | H | H | NH | — | T¹¹¹ | |
| 1434 | H | H | H | H | O | — | T¹¹¹ | oil |
| 1435 | H | H | H | H | NH | — | T¹¹² | |
| 1436 | H | H | H | H | O | — | T¹¹² | oil |
| 1437 | H | H | H | H | NH | — | T¹¹³ | |
| 1438 | H | H | H | H | O | — | T¹¹³ | |
| 1439 | H | H | H | H | NH | — | T¹¹⁴ | |
| 1440 | H | H | H | H | O | — | T¹¹⁴ | |
| 1441 | H | H | H | H | NH | — | T¹¹⁵ | |
| 1442 | H | H | H | H | O | — | T¹¹⁵ | oil |
| 1443 | H | H | H | H | NH | — | T¹¹⁶ | |
| 1444 | H | H | H | H | O | — | T¹¹⁶ | |
| 1445 | H | H | H | H | NH | — | T¹¹⁷ | |
| 1446 | H | H | H | H | O | — | T¹¹⁷ | |
| 1447 | H | H | H | H | NH | — | T¹¹⁸ | |
| 1448 | H | H | H | H | O | — | T¹¹⁸ | oil |
| 1449 | H | H | H | H | NH | — | T¹¹⁹ | |
| 1450 | H | H | H | H | O | — | T¹¹⁹ | |
| 1451 | H | H | H | H | NH | — | T¹²⁰ | |
| 1452 | H | H | H | H | O | — | T¹²⁰ | |
| 1453 | H | H | H | H | NH | — | T¹²¹ | |
| 1454 | H | H | H | H | O | — | T¹²¹ | |
| 1455 | H | H | H | H | NH | — | T¹²² | |
| 1456 | H | H | H | H | O | — | T¹²² | oil |
| 1457 | H | H | H | H | NH | — | T¹²³ | |
| 1458 | H | H | H | H | O | — | T¹²³ | 80 |
| 1459 | H | H | H | H | NH | — | T¹²⁴ | |
| 1460 | H | H | H | H | O | — | T¹²⁴ | |
| 1461 | H | H | H | H | NH | — | T¹²⁵ | |
| 1462 | H | H | H | H | O | — | T¹²⁵ | |
| 1463 | H | H | H | H | NH | — | T¹²⁶ | |
| 1464 | H | H | H | H | O | — | T¹²⁶ | |
| 1465 | H | H | H | H | NH | — | T¹²⁷ | |
| 1466 | H | H | H | H | O | — | T¹²⁷ | |
| 1467 | H | H | H | H | NH | — | T¹²⁸ | |
| 1468 | H | H | H | H | O | — | T¹²⁸ | |
| 1469 | H | H | H | H | NH | — | T¹²⁹ | |
| 1470 | H | H | H | H | O | — | T¹²⁹ | |
| 1471 | H | H | H | H | NH | — | T¹³⁰ | |
| 1472 | H | H | H | H | O | — | T¹³⁰ | |
| 1473 | H | H | H | H | NH | — | T¹³¹ | |
| 1474 | H | H | H | H | O | — | T¹³¹ | |
| 1475 | H | H | H | H | NH | — | T¹³² | |
| 1476 | H | H | H | H | O | — | T¹³² | |
| 1477 | H | H | H | H | NH | — | T¹³³ | |
| 1478 | H | H | H | H | O | — | T¹³³ | |
| 1479 | H | H | H | H | NH | — | T¹³⁴ | |
| 1480 | H | H | H | H | O | — | T¹³⁴ | |
| 1481 | H | H | H | H | NH | — | T¹³⁵ | |
| 1482 | H | H | H | H | O | — | T¹³⁵ | |
| 1483 | H | H | H | H | NH | — | T¹³⁶ | |
| 1484 | H | H | H | H | O | — | T¹³⁶ | |
| 1485 | H | H | H | H | NH | — | T¹³⁷ | |
| 1486 | H | H | H | H | O | — | T¹³⁷ | |
| 1487 | H | H | H | H | NH | — | T¹³⁸ | |
| 1488 | H | H | H | H | O | — | T¹³⁸ | |
| 1489 | H | H | H | H | NH | — | T¹³⁹ | |
| 1490 | H | H | H | H | O | — | T¹³⁹ | |
| 1491 | H | H | H | H | NH | — | T¹⁴⁰ | |

TABLE II-continued

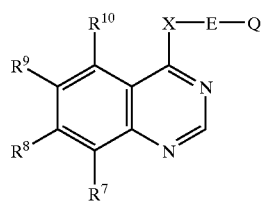

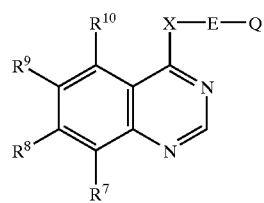

| Example No. | R⁷ | R⁸ | R⁹ | R¹⁰ | X | E | Q | M.p. [° C.] |
|---|---|---|---|---|---|---|---|---|
| 1492 | H | H | H | H | O | — | T¹⁴⁰ | |
| 1493 | H | H | H | H | NH | — | T¹⁴¹ | |
| 1494 | H | H | H | H | O | — | T¹⁴¹ | |
| 1495 | H | H | H | H | NH | — | T¹⁴² | |
| 1496 | H | H | H | H | O | — | T¹⁴² | |
| 1497 | H | H | H | H | NH | — | T¹⁴³ | |
| 1498 | H | H | H | H | O | — | T¹⁴³ | |
| 1499 | H | H | H | H | NH | — | T¹⁴⁴ | |
| 1500 | H | H | H | H | O | — | T¹⁴⁴ | |
| 1501 | H | H | H | H | NH | — | T¹⁴⁵ | |
| 1502 | H | H | H | H | O | — | T¹⁴⁵ | |
| 1503 | H | H | H | H | NH | — | T¹⁴⁶ | |
| 1504 | H | H | H | H | O | — | T¹⁴⁶ | |
| 1505 | H | H | H | H | NH | — | T¹⁴⁷ | |
| 1506 | H | H | H | H | O | — | T¹⁴⁷ | |
| 1507 | H | H | H | H | NH | — | T¹⁴⁸ | |
| 1508 | H | H | H | H | O | — | T¹⁴⁸ | |
| 1509 | H | H | H | H | NH | — | T¹⁴⁹ | |
| 1510 | H | H | H | H | O | — | T¹⁴⁹ | |
| 1511 | H | H | H | H | NH | — | T¹⁵⁰ | |
| 1512 | H | H | H | H | O | — | T¹⁵⁰ | |
| 1513 | H | H | H | H | NH | — | T¹⁵¹ | 188–189 |
| 1514 | H | H | H | H | O | — | T¹⁵¹ | 118 |
| 1515 | H | H | H | H | NH | — | T¹⁵² | |
| 1516 | H | H | H | H | O | — | T¹⁵² | |
| 1517 | H | H | H | H | NH | — | T¹⁵³ | |
| 1518 | H | H | H | H | O | — | T¹⁵³ | |
| 1519 | H | H | H | H | NH | — | T¹⁵⁴ | |
| 1520 | H | H | H | H | O | — | T¹⁵⁴ | |
| 1521 | H | H | H | H | NH | — | T¹⁵⁵ | |
| 1522 | H | H | H | H | O | — | T¹⁵⁵ | |
| 1523 | H | H | H | H | NH | — | T¹⁵⁶ | |
| 1524 | H | H | H | H | O | — | T¹⁵⁶ | |
| 1525 | H | H | H | H | NH | — | T¹⁵⁷ | |
| 1526 | H | H | H | H | O | — | T¹⁵⁷ | |
| 1527 | H | H | H | H | NH | — | T¹⁵⁸ | |
| 1528 | H | H | H | H | O | — | T¹⁵⁸ | |
| 1529 | H | H | H | H | NH | — | T¹⁵⁹ | |
| 1530 | H | H | H | H | O | — | T¹⁵⁹ | |
| 1531 | H | H | H | H | NH | — | T¹⁶⁰ | 78–80 |
| 1532 | H | H | H | H | O | — | T¹⁶⁰ | |
| 1533 | H | H | H | H | NH | — | T¹⁶¹ | 92–94 |
| 1534 | H | H | H | H | O | — | T¹⁶¹ | |
| 1535 | H | H | H | H | NH | — | T¹⁶² | |
| 1536 | H | H | H | H | O | — | T¹⁶² | |
| 1537 | H | H | H | H | NH | — | T¹⁶³ | |
| 1538 | H | H | H | H | O | — | T¹⁶³ | |
| 1539 | H | H | H | H | NH | — | T¹⁶⁴ | |
| 1540 | H | H | H | H | O | — | T¹⁶⁴ | |
| 1541 | H | H | H | H | NH | — | T¹⁶⁵ | |
| 1542 | H | H | H | H | O | — | T¹⁶⁵ | |
| 1543 | H | H | H | H | NH | — | T¹⁶⁶ | |
| 1544 | H | H | H | H | O | — | T¹⁶⁶ | |
| 1545 | H | H | H | H | NH | — | T¹⁶⁷ | |
| 1546 | H | H | H | H | O | — | T¹⁶⁷ | |
| 1547 | H | H | H | H | NH | — | T¹⁶⁸ | |
| 1548 | H | H | H | H | O | — | T¹⁶⁸ | |
| 1549 | H | H | H | H | NH | — | T¹⁶⁹ | |
| 1550 | H | H | H | H | O | — | T¹⁶⁹ | |
| 1551 | H | H | H | H | NH | — | T¹⁷⁰ | |
| 1552 | H | H | H | H | O | — | T¹⁷⁰ | |
| 1553 | H | H | H | H | NH | — | T¹⁷¹ | |
| 1554 | H | H | H | H | O | — | T¹⁷¹ | |
| 1555 | H | H | H | H | NH | — | T¹⁷² | |
| 1556 | H | H | H | H | O | — | T¹⁷² | |
| 1557 | H | H | H | H | NH | — | T¹⁷³ | |
| 1558 | H | H | H | H | O | — | T¹⁷³ | |
| 1559 | H | H | H | H | NH | — | T¹⁷⁴ | |
| 1560 | H | H | H | H | O | — | T¹⁷⁴ | |
| 1561 | H | H | H | H | NH | — | T¹⁷⁵ | |
| 1562 | H | H | H | H | O | — | T¹⁷⁵ | |
| 1563 | H | H | H | H | NH | — | T¹⁷⁶ | |
| 1564 | H | H | H | H | O | — | T¹⁷⁶ | |
| 1565 | H | H | H | H | NH | — | T¹⁷⁷ | |
| 1566 | H | H | H | H | O | — | T¹⁷⁷ | |
| 1567 | H | H | H | H | NH | — | T¹⁷⁸ | |
| 1568 | H | H | H | H | O | — | T¹⁷⁸ | |
| 1569 | H | H | H | H | NH | — | T¹⁷⁹ | |
| 1570 | H | H | H | H | O | — | T¹⁷⁹ | |
| 1571 | H | H | H | H | NH | — | T¹⁸⁰ | |
| 1572 | H | H | H | H | O | — | T¹⁸⁰ | |
| 1573 | H | H | H | H | NH | — | T¹⁸¹ | |
| 1574 | H | H | H | H | O | — | T¹⁸¹ | |
| 1575 | H | H | H | H | NH | — | T¹⁸² | |
| 1576 | H | H | H | H | O | — | T¹⁸² | |
| 1577 | H | H | H | H | NH | — | T¹⁸³ | |
| 1578 | H | H | H | H | O | — | T¹⁸³ | |
| 1579 | H | H | H | H | NH | — | T¹⁸⁴ | |
| 1580 | H | H | H | H | O | — | T¹⁸⁴ | |
| 1581 | H | H | H | H | NH | — | T¹⁸⁵ | |
| 1582 | H | H | H | H | O | — | T¹⁸⁵ | |
| 1583 | H | H | H | H | NH | — | T¹⁸⁶ | |
| 1584 | H | H | H | H | O | — | T¹⁸⁶ | |
| 1585 | H | H | H | H | NH | — | T¹⁸⁷ | |
| 1586 | H | H | H | H | O | — | T¹⁸⁷ | |
| 1587 | H | H | H | H | NH | — | T¹⁸⁸ | |
| 1588 | H | H | H | H | O | — | T¹⁸⁸ | |
| 1589 | H | H | H | H | NH | — | T¹⁸⁹ | |
| 1590 | H | H | H | H | O | — | T¹⁸⁹ | |
| 1591 | H | H | H | H | NH | — | T¹⁹⁰ | |
| 1592 | H | H | H | H | O | — | T¹⁹⁰ | |
| 1593 | H | H | H | H | NH | — | T¹⁹¹ | |
| 1594 | H | H | H | H | O | — | T¹⁹¹ | |
| 1595 | H | H | H | H | NH | — | T¹⁹² | |
| 1596 | H | H | H | H | O | — | T¹⁹² | |
| 1597 | H | H | H | H | NH | — | T¹⁹³ | |
| 1598 | H | H | H | H | O | — | T¹⁹³ | |
| 1599 | H | H | H | H | NH | — | T¹⁹⁴ | |
| 1600 | H | H | H | H | O | — | T¹⁹⁴ | |
| 1601 | H | H | H | H | NH | — | T¹⁹⁵ | |
| 1602 | H | H | H | H | O | — | T¹⁹⁵ | |
| 1603 | H | H | H | H | NH | — | T¹⁹⁶ | |
| 1604 | H | H | H | H | O | — | T¹⁹⁶ | |
| 1605 | H | H | H | H | NH | — | T¹⁹⁷ | |
| 1606 | H | H | H | H | O | — | T¹⁹⁷ | |
| 1607 | H | H | H | H | NH | — | T¹⁹⁸ | |
| 1608 | H | H | H | H | O | — | T¹⁹⁸ | |
| 1609 | H | H | H | H | NH | — | T¹⁹⁹ | |
| 1610 | H | H | H | H | O | — | T¹⁹⁹ | |
| 1611 | H | H | H | H | NH | — | T²⁰⁰ | |
| 1612 | H | H | H | H | O | — | T²⁰⁰ | |
| 1613 | H | H | H | H | NH | — | T²⁰¹ | |
| 1614 | H | H | H | H | O | — | T²⁰¹ | |
| 1615 | H | H | H | H | NH | — | T²⁰² | |
| 1616 | H | H | H | H | O | — | T²⁰² | |
| 1617 | H | H | H | H | NH | — | T²⁰³ | |
| 1618 | H | H | H | H | O | — | T²⁰³ | |
| 1619 | H | H | H | H | NH | — | T²⁰⁴ | |
| 1620 | H | H | H | H | O | — | T²⁰⁴ | |
| 1621 | H | H | H | H | NH | — | T²⁰⁵ | |

TABLE II-continued

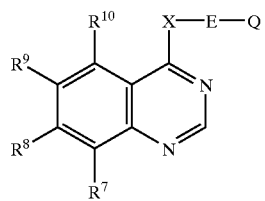

| Example No. | R⁷ | R⁸ | R⁹ | R¹⁰ | X | E | Q | M.p. [° C.] |
|---|---|---|---|---|---|---|---|---|
| 1622 | H | H | H | H | O | — | T²⁰⁵ | |
| 1623 | H | H | H | H | NH | — | T²⁰⁶ | |
| 1624 | H | H | H | H | O | — | T²⁰⁶ | |
| 1625 | H | H | H | H | NH | — | T²⁰⁷ | |
| 1626 | H | H | H | H | O | — | T²⁰⁷ | |
| 1627 | H | H | H | H | NH | — | T²⁰⁸ | |
| 1628 | H | H | H | H | O | — | T²⁰⁸ | |
| 1629 | H | H | H | H | NH | — | T²⁰⁹ | |
| 1630 | H | H | H | H | O | — | T²⁰⁹ | |
| 1631 | H | H | H | H | NH | — | T²¹⁰ | |
| 1632 | H | H | H | H | O | — | T²¹⁰ | |
| 1633 | H | H | H | H | NH | — | T²¹¹ | |
| 1634 | H | H | H | H | O | — | T²¹¹ | |
| 1635 | H | H | H | H | NH | — | T²¹² | |
| 1636 | H | H | H | H | O | — | T²¹² | |
| 1637 | H | H | H | H | NH | — | T²¹³ | |
| 1638 | H | H | H | H | O | — | T²¹³ | |
| 1639 | H | H | H | H | NH | — | T²¹⁴ | |
| 1640 | H | H | H | H | O | — | T²¹⁴ | |
| 1641 | H | H | H | H | NH | — | T²¹⁵ | |
| 1642 | H | H | H | H | O | — | T²¹⁵ | |
| 1643 | H | H | H | H | NH | — | T²¹⁶ | |
| 1644 | H | H | H | H | O | — | T²¹⁶ | |
| 1645 | H | H | H | H | NH | — | T²¹⁷ | |
| 1646 | H | H | H | H | O | — | T²¹⁷ | |
| 1647 | H | H | H | H | NH | — | T²¹⁸ | |
| 1648 | H | H | H | H | O | — | T²¹⁸ | |
| 1649 | H | H | H | H | NH | — | T²¹⁹ | |
| 1650 | H | H | H | H | O | — | T²¹⁹ | |
| 1651 | H | H | H | H | NH | — | T²²⁰ | |
| 1652 | H | H | H | H | O | — | T²²⁰ | |
| 1653 | H | H | H | H | NH | — | T²²¹ | |
| 1654 | H | H | H | H | O | — | T²²¹ | |
| 1655 | H | H | H | H | NH | — | T²²² | |
| 1656 | H | H | H | H | O | — | T²²² | |
| 1657 | H | H | H | H | NH | — | T²²³ | |
| 1658 | H | H | H | H | O | — | T²²³ | |
| 1659 | H | H | H | H | NH | — | T²²⁴ | |
| 1660 | H | H | H | H | O | — | T²²⁴ | |
| 1661 | H | H | H | H | NH | — | T²²⁵ | |
| 1662 | H | H | H | H | O | — | T²²⁵ | |
| 1663 | H | H | H | H | NH | — | T²²⁶ | |
| 1664 | H | H | H | H | O | — | T²²⁶ | |
| 1665 | H | H | H | H | NH | — | T²²⁷ | |
| 1666 | H | H | H | H | O | — | T²²⁷ | |
| 1667 | H | H | H | H | NH | — | T²²⁸ | |
| 1668 | H | H | H | H | O | — | T²²⁸ | |
| 1669 | H | H | H | H | NH | — | T²²⁹ | |
| 1670 | H | H | H | H | O | — | T²²⁹ | |
| 1671 | H | H | H | H | NH | — | T²³⁰ | |
| 1672 | H | H | H | H | O | — | T²³⁰ | |
| 1673 | H | H | H | H | NH | — | T²³¹ | |
| 1674 | H | H | H | H | O | — | T²³¹ | |
| 1675 | H | H | H | H | NH | — | T²³² | |
| 1676 | H | H | H | H | O | — | T²³² | |
| 1677 | H | H | H | H | NH | — | T²³³ | |
| 1678 | H | H | H | H | O | — | T²³³ | |
| 1679 | H | H | H | H | NH | — | T²³⁴ | |
| 1680 | H | H | H | H | O | — | T²³⁴ | |
| 1681 | H | H | H | H | NH | — | T²³⁵ | |
| 1682 | H | H | H | H | O | — | T²³⁵ | |
| 1683 | H | H | H | H | NH | — | T²³⁶ | |
| 1684 | H | H | H | H | O | — | T²³⁶ | |
| 1685 | H | H | H | H | NH | — | T²³⁷ | |
| 1686 | H | H | H | H | O | — | T²³⁷ | |

TABLE II-continued

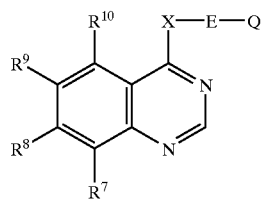

| Example No. | R⁷ | R⁸ | R⁹ | R¹⁰ | X | E | Q | M.p. [° C.] |
|---|---|---|---|---|---|---|---|---|
| 1687 | H | H | H | H | NH | — | T²³⁸ | |
| 1688 | H | H | H | H | O | — | T²³⁸ | |
| 1689 | H | H | H | H | NH | — | T²³⁹ | |
| 1690 | H | H | H | H | O | — | T²³⁹ | |
| 1691 | H | H | H | H | NH | — | T²⁴⁰ | |
| 1692 | H | H | H | H | O | — | T²⁴⁰ | |
| 1693 | H | H | H | H | NH | — | T²⁴¹ | |
| 1694 | H | H | H | H | O | — | T²⁴¹ | |
| 1695 | H | H | H | H | NH | — | T²⁴² | |
| 1696 | H | H | H | H | O | — | T²⁴² | |
| 1697 | H | H | H | H | NH | — | T²⁴³ | |
| 1698 | H | H | H | H | O | — | T²⁴³ | |
| 1699 | H | H | H | H | NH | — | T²⁴⁴ | |
| 1700 | H | H | H | H | O | — | T²⁴⁴ | |
| 1701 | H | H | H | H | NH | — | T²⁴⁵ | |
| 1702 | H | H | H | H | O | — | T²⁴⁵ | |
| 1703 | H | H | H | H | NH | — | T²⁴⁶ | |
| 1704 | H | H | H | H | O | — | T²⁴⁶ | |
| 1705 | H | H | H | H | NH | — | T²⁴⁷ | |
| 1706 | H | H | H | H | O | — | T²⁴⁷ | |
| 1707 | H | H | H | H | NH | — | T²⁴⁸ | |
| 1708 | H | H | H | H | O | — | T²⁴⁸ | |

TABLE III

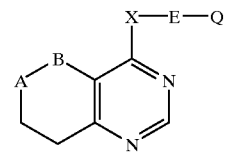

| Example No. | A | B | X | E | Q | M.p. [° C.] |
|---|---|---|---|---|---|---|
| 1709 | CH | S | NH | — | T⁷ | |
| 1710 | " | " | O | — | T⁷ | |
| 1711 | S | CH | NH | — | T⁷ | |
| 1712 | " | " | O | — | T⁷ | |
| 1713 | CH | S | NH | — | T⁹ | |
| 1714 | S | CH | O | — | T⁹ | |
| 1715 | S | CH | NH | — | T⁹ | |
| 1716 | " | " | O | — | T⁹ | |
| 1717 | CH | S | NH | — | T⁸ | |
| 1718 | " | " | O | — | T⁸ | |
| 1719 | S | CH | NH | — | T⁸ | |
| 1720 | " | " | O | — | T⁸ | |
| 1721 | CH | S | NH | — | T⁴ | |
| 1722 | " | " | O | — | T⁴ | |
| 1723 | S | CH | NH | — | T⁴ | |
| 1724 | " | " | O | — | T⁴ | |
| 1725 | CH | S | NH | — | T¹⁰ | |
| 1726 | " | " | O | — | T¹⁰ | |
| 1727 | S | CH | NH | — | T¹⁰ | |
| 1728 | S | CH | O | — | T¹⁰ | |
| 1729 | CH | S | NH | — | T¹¹ | |
| 1730 | " | " | O | — | T¹¹ | |
| 1731 | S | CH | NH | — | T¹¹ | |
| 1732 | " | " | O | — | T¹¹ | |
| 1733 | CH | S | NH | — | T¹² | |
| 1734 | " | " | O | — | T¹² | |
| 1735 | S | CH | NH | — | T¹² | |

TABLE III-continued

Structure: A-B fused ring with X—E—Q substituent on pyrimidine

| Example No. | A | B | X | E | Q | M.p. [° C.] |
|---|---|---|---|---|---|---|
| 1736 | " | " | O | — | T$^{12}$ | |
| 1737 | CH | S | NH | — | T$^{14}$ | |
| 1738 | " | " | O | — | T$^{14}$ | |
| 1739 | S | CH | NH | — | T$^{14}$ | |
| 1740 | " | " | " | — | T$^{14}$ | |
| 1741 | CH | S | NH | | T$^{23}$ | 118–120 |
| 1742 | " | " | O | — | T$^{23}$ | |
| 1743 | S | CH | NH | — | T$^{23}$ | |
| 1744 | " | " | O | — | T$^{23}$ | |
| 1745 | CH | S | NH | | T$^{58}$ | |
| 1746 | " | " | O | | T$^{58}$ | |
| 1747 | S | CH | NH | | T$^{58}$ | |
| 1748 | " | " | O | | T$^{58}$ | |

TABLE IV

| Example No. | X | R | M.p. [° C.] |
|---|---|---|---|
| 1749 | NH | ----C(CH$_3$)$_3$ | 238–240 |
| 1750 | NH | ◀C(CH$_3$)$_3$ | 152–154 |

TABLE V

| Example No. | X | Q | M.p. [° C.] |
|---|---|---|---|
| 1751 | NH | T$^4$ | |
| 1752 | NH | T$^7$ | |
| 1753 | NH | T$^8$ | |
| 1754 | NH | T$^9$ | |
| 1755 | O | T$^9$ | |
| 1756 | NH | T$^{10}$ | |
| 1757 | NH | T$^{12}$ | |
| 1758 | NH | T$^{14}$ | |
| 1759 | NH | T$^{23}$ | |
| 1760 | O | T$^{23}$ | |
| 1761 | NH | T$^{66}$ | |
| 1762 | NH | T$^{68}$ | |
| 1763 | NH | T$^{70}$ | |
| 1764 | O | T$^{70}$ | |

TABLE V-continued

| Example No. | X | Q | M.p. [° C.] |
|---|---|---|---|
| 1765 | NH | T$^{76}$ | |
| 1766 | O | T$^{76}$ | |

TABLE VI

| Example No. | X | Q | M.p. [° C.] |
|---|---|---|---|
| 1767 | NH | T$^4$ | |
| 1768 | NH | T$^7$ | |
| 1769 | NH | T$^8$ | |
| 1770 | NH | T$^9$ | |
| 1771 | O | T$^9$ | |
| 1772 | NH | T$^{10}$ | |
| 1773 | NH | T$^{12}$ | |
| 1774 | NH | T$^{14}$ | |
| 1775 | NH | T$^{23}$ | |
| 1776 | O | T$^{23}$ | |
| 1777 | NH | T$^{66}$ | |
| 1778 | NH | T$^{68}$ | |
| 1779 | NH | T$^{20}$ | |
| 1780 | O | T$^{20}$ | |
| 1781 | NH | T$^{76}$ | |
| 1782 | O | T$^{76}$ | |

TABLE VII

| Example No. | X | Q | M.p. [° C.] |
|---|---|---|---|
| 1783 | NH | T$^4$ | |
| 1784 | NH | T$^7$ | |
| 1785 | NH | T$^8$ | |
| 1786 | NH | T$^9$ | |
| 1787 | O | T$^9$ | |
| 1788 | NH | T$^{10}$ | |
| 1789 | NH | T$^{12}$ | |
| 1790 | NH | T$^{14}$ | |
| 1791 | NH | T$^{23}$ | |
| 1792 | O | T$^{23}$ | |
| 1793 | NH | T$^{66}$ | |
| 1794 | NH | T$^{68}$ | |
| 1795 | NH | T$^{70}$ | |
| 1796 | O | T$^{70}$ | |

TABLE VII-continued

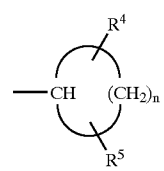

| Example No. | X | M.p. [° C.] |
|---|---|---|
| 1797 | NH | $T^{76}$ |
| 1798 | O | $T^{76}$ |

TABLE VIII

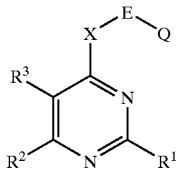

| Example No. | X | M.p. [°C.] |
|---|---|---|
| 1799 | NH | $T^4$ |
| 1800 | NH | $T^7$ |
| 1801 | NH | $T^8$ |
| 1802 | NH | $T^9$ |
| 1803 | O | $T^9$ |
| 1804 | NH | $T^{10}$ |
| 1805 | NH | $T^{12}$ |
| 1806 | NH | $T^{14}$ |
| 1807 | NH | $T^{23}$ |
| 1808 | O | $T^{23}$ |
| 1809 | NH | $T^{66}$ |
| 1810 | NH | $T^{68}$ |
| 1811 | NH | $T^{70}$ |
| 1812 | O | $T^{70}$ |
| 1813 | NH | $T^{76}$ |
| 1814 | O | $T^{76}$ |

What is claimed is:

1. A compound of the formula I $$(I)$$

in which $R^1$ is hydrogen, halogen, $(C_1-C_4)$-alkyl or $(C_3-C_6)$-cycloalkyl, $R^2$ is hydrogen, $(C_1-C_4)$-alkyl, halogen, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-alkylthio, $(C_1-C_4)$-alkylthio-$(_1-C_4)$-alkyl, $(C_1-C_4)$-alkyl-amino or di-$(C_1-C_4)$-alkylamino, $R^3$ is hydrogen, $(C_1-C_4)$-alkyl, $(C_1-C_4)$-alkoxy, $(C_1-C_4)$-haloalkoxy, halogen, $(C_1-C_4)$-alkylthio, amino, $(C_1-C_4)$-alkylamino or di-$(C_1-C_4)$-alkyl-amino or $R^2$ and $R^3$ together with the carbon atoms to which they are bonded form an unsaturated 5- or 6-membered carbocyclic ring which, if it is a 5-membered ring, can contain an oxygen or sulfur atom in place of $CH_2$ and which is optionally substituted by 1, 2 or 3 identical or different radicals, these radicals being $(C_1-C_4)$-alkyl, $(C_1-C_4)$-alkoxy, $(C_1-C_4)$-haloalkyl, $(C_1-C_4)$-haloalkoxy or halogen, or $R^2$ and $R^3$ together with the carbon atoms to which they are bonded form a saturated 5- 6- or 7-membered carbocyclic ring which can contain an oxygen or sulfur atom in place of $CH_2$ and which is optionally substituted by 1, 2 or 3 $(CH_1-C_4)$-alkyl groups, X is NH or oxygen, E is a direct bond or a straight-chain or branched $(C_1-C_4)$-alkanediyl group, Q has the meaning $Q^1$ and $Q^1$ is a cycloalkyl group of the formula II $$(II)$$

in which n is an integer from 2 to 7, $R^4$ and $R^5$ are identical or different and are in each case hydrogen, $(C_1-C_{12})$-alkyl, $(C_3-C_8)$-cycloalkyl, $(C_3-C_8)$-cycloalkyl-$(C_1-C_4)$-alkyl, $(C_1-C_8)$-alkoxy, $(C_3-C_8)$-cycloalkoxy, $(C_1-C_4)$-alkoxy-$(C_1-C_4)$-alkyl, $(C_3-C_8)$-cycloalkyl-$(C_1-C_4)$-alkoxy, tri-$(C_1-C_8)$-alkylsilyl, di-$(C_1-C_8)$-alkyl-$(C_3-C_8)$-cycloalkyl-silyl, di-$(C_1-C_8)$-alkyl-(phenyl-$(C_1-C_4)$-alkyl)-silyl, di-$(C_1-C_8)$-alkyl-$(C_1-C_4)$-haloalkylsilyl, dimethylphenyl silyl, $(C_1-C_4)$-haloalkyl, halogen, $(C_1-C_4)$-haloalkoxy, heteroaryl, phenyl, phenyl-$(C_1-C_4)$-alkyl, benzyloxy, benzyloxy-$(C_1-C_4)$-alkyl, benzylthio, phenylthio or phenoxy, it being possible for the phenyl rings in the seven last-mentioned radicals to be unsubstituted or provided with one or two substituents and these substituents are identical or different and can be in each case $(C_1-C_8)$-alkyl, $(C_3-C_8)$-cycloalkyl, $(C_1-C_4)$-haloalkyl, halogen, $(C_1-C_4)$-dialkylamino, $(C_1-C_4)$-alkylthio, $(C_1-C_8)$-alkoxy, $(C_1-C_4)$-haloalkoxy, $(C_1-C_4)$-alkoxy-$(C_1-C_4)$-alkoxy, $H_5C_2$—O—$[CH_2$-$CH_2$-$O]_y$,2-(tetrahydro-2H-pyran-2-yloxy)-ethoxy, $(C_2-C_8)$-alkenyl, $(C_2-C_8)$-alkynyl, benzyloxy which in the phenyl radical optionally carries one or two identical or different substituents selected from the group comprising $(C_1-C_4)$-alkyl, $(C_1-C_4)$-haloalkyl, $(C_1-C_4)$-alkoxy, $(C_1-C_4)$-haloalkoxy and halogen, or tri-$(C_1-C_4)$-alkylsilylmethoxy, $(C_3-C_8)$-cycloalkyl-$(C_1-C_4)$-alkoxy, 1,3-dioxolan-2-ylmethoxy, tetrahydrofuran-2-ylmethoxy or tetrahydro-2H-pyran-2-ylmethoxy, and at least one of $R^4$ and $R^5$ is heteroaryl, wherein the term heteroaryl is aryl in which at least one CH group is replace by N and/or at least two adjacent CH groups are replaced by S, NH or O, and wherein aryl is phenyl, naphtyl or biphenyl, y is 2, 3 or 4, or Q has the meaning $Q^2$ and $Q^2$ is a group of the formula III

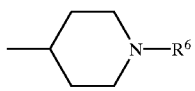
(III)

in which $R^6$ is a group of the formula Z-W and Z is a direct bond or carbonyl or sulfonyl and W is optionally substituted heteroaryl, which heteroaryl is as defined above for $R^4$ and $R^5$ with the exception of heteroaryl selected from the group consisting 2-pyridyl, 2-quinoxalinyl and 2-pyrimidinyl, and which heteroaryl can be unsubstituted or provided with one or two substituents and these substituents are identical or different and are in each case $(C_1–C_8)$-alkyl, $(C_3–C_8)$-cycloalkyl, trifluoromethyl, halogen, $(C_1–C_4)$-alkoxy, $(C_1–C_8)$-dialkylamino or $(C_1–C_4)$-alkythio, or acid addition salts thereof.

2. A compound of the formula I as claimed in claim 1, in which $R^1$ is hydrogen, methyl or cyclopropyl, $R^2$ is $(C_1–C_4)$-alkyl, chlorine, methoxy, ethoxy or methoxymethyl, $R^3$ is hydrogen, $(C_1–C_3)$-alkyl, methoxy, ethoxy or halogen or $R^2$ and $R^3$ together with the carbon atoms to which they are bonded form an unsaturated 5- or 6-membered ring which can contain an oxygen or sulfur atom, or $R^2$ and $R^3$ together with the carbon atoms to which they are bonded form a saturated 5- or 6-membered ring which can contain a sulfur atom, Q has the meaning $Q^1$ or $Q^2$, or acid addition salts thereof.

3. A compound of the formula I as claimed in claim 1, in which $R^1$ is hydrogen or methyl, $R^2$ is methyl, ethyl, methoxy, ethoxy, or methoxy-methyl, $R^3$ is methyl, ethyl, methoxy, chlorine or bromine, or $R^2$ and $R^3$ together with the carbon atoms to which they are bonded form the quinazoline system, which can be mono-, di- or trisubstituted by fluorine, chlorine, bromine, methyl and/or methoxy, or $R^2$ and $R^3$ together with the carbon atoms to which they are bonded form a saturated 6-membered ring which can contain a sulfur atom and Q has the meaning $Q^1$ and $Q^2$, or acid addition salts thereof.

4. A compound of the formula I as claimed in claim 1, in which

E is a direct bond, $R^1$ is hydrogen, $R^2$ is methyl, ethyl or methoxymethyl, $R^3$ is chlorine, bromine, or methoxy or $R^2$ and $R^3$ together with the carbon atoms to which they are bonded form the quinazoline system which can be substituted by fluorine, chlorine, bromine or methyl, or $R^2$ and $R^3$ together with the pyridimidine ring form the 5,6,7,8-tetrahydroquinazoline system or the 5,6-dihydro-7H-thiopyrano[2,3-d] pyrimidine or the 5,6-dihydro-8H-thiopyrano[3,4-d] pyrimidine system and Q has the meaning $Q^1$ or $Q_2$, or acid addition salts thereof.

5. A compound of the formula I as claimed in claim 1, in which $R^1$ is hydrogen, $R^2$ is methoxymethyl and $R^3$ is methoxy or $R^2$ is methyl or ethyl and $R^3$ is chlorine or bromine or $R^2$ and $R^3$ together with the carbon atom to which they are bonded form a quinazoline system which is substituted by fluorine, chlorine, or methyl, or form a 5,6,7,8-tetrahydro-quinazolin system and Q has the meaning $Q^1$, or acid addition salts thereof.

6. A compound of the formula I as claimed in claim 1, in which

E is a direct bond, $R^1$ is hydrogen, $R^2$ is methoxymethyl and $R^3$ is methoxy or $R^2$ is ethyl and $R^3$ is chlorine or $R^2$ and $R^3$ together with the carbon atoms to which they are bonded form a quinazoline or a 5,6,7,8-tetrahydroquinazoline system and $Q^1$ is a cycloalkyl group of the formula II which is substituted in the 3- or 4-position and in which n is 4 or 5, $R^4$ is $(C_3–C_8)$-alkyl, cyclopentyl, cyclohexyl, phenyl or phenoxy, it being possible for the two last-mentioned radicals to be unsubstituted or provided with one or two substituents which can be identical or different and which are fluorine, chlorine, bromine, $(C_1–C_4)$-alkyl, $(C_1–C_4)$-alkoxy, trifluoromethyl, $(C_1–C_2)$-haloalkoxy, cyclohexyl, 2-ethoxyethoxy, methylthio or dimethylamino, or acid addition salts thereof.

7. A compound of the formula I as claimed in claim 1, in which

E is a direct bond, $R^1$ is hydrogen, $R^2$ is methoxymethyl and $R^3$ is methoxy or $R^2$ is ethyl and $R^3$ is chlorine, or $R^2$ and $R^3$ together with the carbon atoms to which they are bonded form a quinazoline or a 5,6,7,8-tetrahydroquinazoline system, Q has the meaning $Q^1$ and $Q^1$ is cyclohexyl which is substituted in the 4-position, and E and the substituent in the 4-position of the cyclohexyl are in the cis-position relative to each other, or acid addition salts thereof.

8. An insecticidal or acaricidal composition which comprises an effective amount of a compound of the formula I as claimed in claim 1 and suitable formulation auxiliaries.

9. A method of controlling insect pests and acarids, which comprises applying an effective amount of a compound of the formula I as claimed in claim 1 to these insect pests or acarids or to the plants, areas or substrates which are infested with them.

* * * * *